United States Patent
Vehring et al.

(10) Patent No.: US 10,716,753 B2
(45) Date of Patent: *Jul. 21, 2020

(54) COMPOSITIONS FOR PULMONARY DELIVERY OF LONG-ACTING MUSCARINIC ANTAGONISTS OR LONG-ACTING B2 ADRENERGIC RECEPTOR AGONISTS AND ASSOCIATED METHODS AND SYSTEMS

(71) Applicant: Pearl Therapeutics, Inc., Redwood City, CA (US)

(72) Inventors: Reinhard Vehring, Edmonton (CA); Michael Steven Hartman, Millbrae, CA (US); Adrian Edward Smith, Emerald Hills, CA (US); Vidya B. Joshi, Redwood City, CA (US); Sarvajna Kumar Dwivedi, Redwood City, CA (US)

(73) Assignee: Pearl Therapeutics, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/179,712

(22) Filed: Nov. 2, 2018

(65) Prior Publication Data

US 2019/0307676 A1 Oct. 10, 2019

Related U.S. Application Data

(63) Continuation of application No. 15/252,001, filed on Aug. 30, 2016, now abandoned, which is a continuation of application No. 12/790,448, filed on May 28, 2010, now Pat. No. 9,463,161.

(60) Provisional application No. 61/182,565, filed on May 29, 2009, provisional application No. 61/258,172, filed on Nov. 4, 2009, provisional application No. 61/309,365, filed on Mar. 1, 2010, provisional application No. 61/345,536, filed on May 17, 2010.

(51) Int. Cl.
| | |
|---|---|
| *A61K 9/12* | (2006.01) |
| *A61K 9/14* | (2006.01) |
| *A61K 31/58* | (2006.01) |
| *A61K 31/137* | (2006.01) |
| *A61K 9/00* | (2006.01) |
| *A61K 31/167* | (2006.01) |
| *A61K 31/40* | (2006.01) |
| *A61K 31/46* | (2006.01) |
| *A61K 31/56* | (2006.01) |
| *A61K 31/135* | (2006.01) |
| *A61K 31/16* | (2006.01) |
| *A61K 31/192* | (2006.01) |
| *A61K 31/194* | (2006.01) |
| *A61K 31/573* | (2006.01) |
| *A61M 15/00* | (2006.01) |
| *A61K 9/16* | (2006.01) |

(52) U.S. Cl.
CPC .......... *A61K 9/008* (2013.01); *A61K 9/1611* (2013.01); *A61K 9/1617* (2013.01); *A61K 31/135* (2013.01); *A61K 31/137* (2013.01); *A61K 31/16* (2013.01); *A61K 31/167* (2013.01); *A61K 31/192* (2013.01); *A61K 31/194* (2013.01); *A61K 31/40* (2013.01); *A61K 31/46* (2013.01); *A61K 31/56* (2013.01); *A61K 31/573* (2013.01); *A61K 31/58* (2013.01); *A61M 15/0065* (2013.01)

(58) Field of Classification Search
CPC ........ A61K 9/008; A61K 9/12; A61K 31/135; A61K 31/137; A61K 31/167; A61K 31/40; A61K 31/46
See application file for complete search history.

(56) References Cited

U.S. PATENT DOCUMENTS

| | | | |
|---|---|---|---|
| 2,956,062 | A | 10/1960 | Lunsford |
| 3,929,768 | A | 12/1975 | Brattsand et al. |
| 3,994,974 | A | 11/1976 | Murakami et al. |
| 4,187,301 | A | 2/1980 | Edwards |
| 4,335,121 | A | 6/1982 | Phillipps et al. |
| 4,472,393 | A | 9/1984 | Shapiro |
| 4,992,474 | A | 2/1991 | Skidmore et al. |
| 5,126,375 | A | 6/1992 | Skidmore et al. |
| 5,225,445 | A | 7/1993 | Skidmore et al. |

(Continued)

FOREIGN PATENT DOCUMENTS

| | | |
|---|---|---|
| AU | 642913 B2 | 4/1991 |
| AU | 775588 B2 | 12/2000 |

(Continued)

OTHER PUBLICATIONS

"Guidance for Industry: Nasal Spray and Inhalation Solution, Suspension, and Spray Drug Products—Chemistry, Manufacturing, and Controls Documentation," retrieved on Feb. 19, 2014 from http://www.fda.gov/downloads/drugs/guidanceComplianceRegulatoryInformation/Guidance/ucm070575.pdf, U.S. Department of Health and Human Services, Food and Drug Administration, Center for Drug Evaluation and Research, pp. 13-14, Jul. 2002, 48 pages.
Advisory Action, dated Feb. 1, 2013, for co-pending U.S. Appl. No. 12/790,448, 2 pages.
Advisory Action, dated Jun. 27, 2012, for U.S. Appl. No. 12/790,671, 3 pages.
Applicant Initiated Interview Summary dated Jan. 30, 2012 in corresponding U.S. Appl. No. 12/790,671.

(Continued)

*Primary Examiner* — Mina Haghighatian
(74) *Attorney, Agent, or Firm* — Seed IP Law Group LLP

(57) ABSTRACT

Compositions, methods and systems are provided for pulmonary delivery of long-acting muscarinic antagonists and long-acting $\beta_2$ adrenergic receptor agonists via a metered dose inhaler. In particular embodiments, the compositions include a suspension medium, active agent particles, and suspending particles, in which the active agent particles and suspending particles form a co-suspension within the suspension medium.

41 Claims, 30 Drawing Sheets

(56) References Cited

U.S. PATENT DOCUMENTS

| | | |
|---|---|---|
| 5,610,163 A | 3/1997 | Banholzer et al. |
| 5,612,053 A | 3/1997 | Baichwal et al. |
| 5,654,314 A | 8/1997 | Banholzer et al. |
| 5,684,199 A | 11/1997 | Francotte |
| 5,707,634 A | 1/1998 | Schmitt |
| 5,709,884 A | 1/1998 | Trofast et al. |
| 5,727,333 A | 3/1998 | Folan |
| 5,833,891 A | 11/1998 | Subramaniam et al. |
| 5,851,453 A | 12/1998 | Hanna et al. |
| 5,858,410 A | 1/1999 | Muller et al. |
| 5,886,200 A | 3/1999 | Kwok et al. |
| 5,889,015 A | 3/1999 | Sequeira et al. |
| 5,928,469 A | 7/1999 | Franks et al. |
| 6,030,604 A | 2/2000 | Trofast |
| 6,040,344 A | 3/2000 | Gao et al. |
| 6,054,488 A | 4/2000 | Oliver et al. |
| 6,057,307 A | 5/2000 | Sequeira et al. |
| 6,057,581 A | 5/2000 | Doan |
| 6,063,138 A | 5/2000 | Hanna et al. |
| 6,068,832 A | 5/2000 | Berry et al. |
| 6,129,905 A | 10/2000 | Cutie |
| 6,177,560 B1 | 1/2001 | Heggie et al. |
| 6,258,341 B1 | 7/2001 | Foster et al. |
| 6,260,549 B1 | 7/2001 | Sosiak |
| 6,309,623 B1 | 10/2001 | Weers et al. |
| 6,309,671 B1 | 10/2001 | Foster et al. |
| 6,358,530 B1 | 3/2002 | Eljamal et al. |
| 6,365,581 B1 | 4/2002 | Sequeira et al. |
| 6,372,258 B1 | 4/2002 | Platz et al. |
| 6,433,027 B1 | 8/2002 | Bozung et al. |
| 6,433,040 B1 | 8/2002 | Dellamary et al. |
| 6,451,285 B2 | 9/2002 | Blondino et al. |
| 6,455,524 B1 | 9/2002 | Bozung et al. |
| RE37,872 E | 10/2002 | Franks et al. |
| 6,475,467 B1 | 11/2002 | Keller et al. |
| 6,518,239 B1 | 2/2003 | Kuo et al. |
| 6,537,524 B1 | 3/2003 | Hassan et al. |
| 6,565,885 B1 | 5/2003 | Tarara et al. |
| 6,585,958 B1 | 7/2003 | Keller et al. |
| 6,630,466 B2 | 10/2003 | Bozung et al. |
| 6,638,495 B2 | 10/2003 | Weers et al. |
| 6,667,344 B2 | 12/2003 | Banerjee et al. |
| 6,677,322 B2 | 1/2004 | Sequeira et al. |
| 6,677,323 B2 | 1/2004 | Sequeira et al. |
| 6,719,994 B2 | 4/2004 | Meoli et al. |
| 6,777,423 B2 | 8/2004 | Banholzer et al. |
| 6,814,953 B2 | 11/2004 | Banerjee et al. |
| 6,908,928 B2 | 6/2005 | Banholzer et al. |
| 6,946,117 B1 | 9/2005 | Schutt et al. |
| 6,964,759 B2 | 11/2005 | Lewis et al. |
| 7,048,908 B2 | 5/2006 | Basu et al. |
| 7,067,502 B2 | 6/2006 | Hassan et al. |
| 7,186,401 B2 | 3/2007 | Keller et al. |
| 7,205,343 B2 | 4/2007 | Dellamary et al. |
| 7,229,607 B2 | 6/2007 | Bannister et al. |
| 7,234,464 B2 | 6/2007 | Goede et al. |
| 7,244,742 B2 | 7/2007 | Pieper et al. |
| RE39,820 E | 9/2007 | Banholzer et al. |
| 7,273,604 B2 | 9/2007 | Hills et al. |
| 7,306,787 B2 | 12/2007 | Tarara et al. |
| 7,393,544 B2 | 7/2008 | Dellamary et al. |
| 7,442,388 B2 | 10/2008 | Weers et al. |
| 7,566,705 B2 | 7/2009 | Hassan et al. |
| 7,628,978 B2 | 12/2009 | Weers et al. |
| 7,736,670 B2 | 6/2010 | Staniforth et al. |
| 7,790,145 B2 | 9/2010 | Weers et al. |
| 7,915,303 B2 | 3/2011 | Baxter |
| 7,985,766 B2 | 7/2011 | Goede et al. |
| 8,048,451 B2 | 11/2011 | Staniforth et al. |
| 8,048,910 B2 | 11/2011 | Maus et al. |
| 8,080,263 B2 | 12/2011 | Dellamary et al. |
| 8,168,223 B1 | 5/2012 | Tarara et al. |
| 8,246,934 B2 | 8/2012 | Weers et al. |
| 8,252,268 B2 | 8/2012 | Slowey et al. |
| 8,303,991 B2 | 11/2012 | Staniforth et al. |
| 8,324,266 B2 | 12/2012 | Vehring et al. |
| 8,435,567 B2 | 5/2013 | Staniforth et al. |
| 8,703,806 B2 | 4/2014 | Vehring et al. |
| 8,808,713 B2 | 8/2014 | Vehring et al. |
| 8,815,258 B2 | 8/2014 | Vehring et al. |
| 9,415,009 B2 | 8/2016 | Vehring et al. |
| 9,463,161 B2 | 10/2016 | Vehring et al. |
| 2001/0049396 A1 | 12/2001 | Ekstrom |
| 2002/0017295 A1 | 2/2002 | Weers et al. |
| 2002/0188281 A1 | 12/2002 | Dellamary et al. |
| 2003/0018019 A1 | 1/2003 | Meade et al. |
| 2003/0026766 A1 | 2/2003 | Sanders |
| 2003/0068280 A1 | 4/2003 | Bannister et al. |
| 2003/0114428 A1 | 6/2003 | Sequeira et al. |
| 2003/0185766 A1 | 10/2003 | Schmelzer |
| 2004/0081584 A1 | 4/2004 | Dayrit et al. |
| 2004/0081627 A1 | 4/2004 | Jinks et al. |
| 2004/0101483 A1 | 5/2004 | Muller-Walz et al. |
| 2004/0105821 A1 | 6/2004 | Bernstein et al. |
| 2004/0170568 A1 | 9/2004 | Weers et al. |
| 2004/0202616 A1 | 10/2004 | Keller et al. |
| 2005/0009795 A1 | 1/2005 | Cuenoud et al. |
| 2005/0042174 A1 | 2/2005 | Nilsson et al. |
| 2005/0080052 A1 | 4/2005 | Hills et al. |
| 2005/0121026 A1 | 6/2005 | Nilsson et al. |
| 2005/0175548 A1 | 8/2005 | Goede et al. |
| 2005/0175549 A1 | 8/2005 | Goede et al. |
| 2005/0207986 A1 | 9/2005 | Schutt et al. |
| 2005/0255049 A1 | 11/2005 | Slowey et al. |
| 2005/0287077 A1 | 12/2005 | Creazzo et al. |
| 2006/0140873 A1 | 6/2006 | Chang |
| 2006/0148693 A1 | 7/2006 | Wollin |
| 2006/0159629 A1 | 7/2006 | Tarara et al. |
| 2006/0165606 A1 | 7/2006 | Tarara et al. |
| 2006/0252815 A1 | 11/2006 | Goede et al. |
| 2006/0257324 A1 | 11/2006 | Lewis et al. |
| 2006/0269484 A1 | 11/2006 | Knopeck et al. |
| 2006/0286041 A1 | 12/2006 | Goeggel et al. |
| 2007/0020190 A1 | 1/2007 | Razzetti et al. |
| 2007/0104658 A1 | 5/2007 | Batycky et al. |
| 2007/0122351 A1 | 5/2007 | Kunka et al. |
| 2007/0193577 A1 | 8/2007 | Keller |
| 2007/0196285 A1 | 8/2007 | Maus et al. |
| 2007/0212405 A1 | 9/2007 | Dellamary et al. |
| 2007/0270481 A1 | 11/2007 | Goede et al. |
| 2008/0125407 A1 | 5/2008 | Chu et al. |
| 2008/0220073 A1 | 9/2008 | Bannister et al. |
| 2008/0226564 A1 | 9/2008 | Weers et al. |
| 2008/0227690 A1 | 9/2008 | Schmitke et al. |
| 2008/0233194 A1 | 9/2008 | Dellamary et al. |
| 2008/0254127 A1 | 10/2008 | Watanabe et al. |
| 2008/0267886 A1 | 10/2008 | Collingwood |
| 2008/0274189 A1 | 11/2008 | Collingwood et al. |
| 2008/0279948 A1 | 11/2008 | Collingwood et al. |
| 2008/0286363 A1 | 11/2008 | Collingwood et al. |
| 2008/0300226 A1 | 12/2008 | Goede et al. |
| 2008/0317862 A1 | 12/2008 | Collingwood et al. |
| 2009/0011030 A1 | 1/2009 | Jouhikainen et al. |
| 2009/0088408 A1 | 4/2009 | Meade et al. |
| 2009/0130026 A1 | 5/2009 | Lewis et al. |
| 2009/0298802 A1 | 12/2009 | Sequeira et al. |
| 2010/0034890 A1 | 2/2010 | Clarke et al. |
| 2010/0197719 A1 | 8/2010 | Bozung et al. |
| 2010/0329984 A1 | 12/2010 | Weers et al. |
| 2011/0023876 A1 | 2/2011 | Vehring et al. |
| 2011/0132356 A1 | 6/2011 | Vehring et al. |
| 2011/0132357 A1 | 6/2011 | Vehring et al. |
| 2011/0135737 A1 | 6/2011 | Vehring et al. |
| 2012/0024554 A1 | 2/2012 | Boehm et al. |
| 2012/0039817 A1 | 2/2012 | Vehring et al. |
| 2012/0039952 A1 | 2/2012 | Vehring et al. |
| 2013/0092160 A1 | 4/2013 | Vehring et al. |
| 2014/0377190 A1 | 12/2014 | Vehring et al. |
| 2015/0017104 A1 | 1/2015 | Vehring et al. |
| 2015/0017247 A1 | 1/2015 | Vehring et al. |
| 2015/0150787 A1 | 6/2015 | Lechuga-Ballesteros et al. |
| 2017/0000725 A1 | 1/2017 | Vehring et al. |
| 2017/0071850 A1 | 3/2017 | Vehring et al. |

(56) References Cited

U.S. PATENT DOCUMENTS

| | | | |
|---|---|---|---|
| 2017/0112759 A1 | 4/2017 | Vehring et al. | |
| 2018/0125776 A1 | 5/2018 | Vehring et al. | |
| 2019/0038548 A1 | 2/2019 | Vehring et al. | |

FOREIGN PATENT DOCUMENTS

| | | |
|---|---|---|
| CA | 2 442 415 A1 | 10/2002 |
| CA | 2 479 638 A1 | 10/2003 |
| CA | 2 495 454 A1 | 3/2004 |
| CA | 2 527 178 A1 | 12/2004 |
| CA | 2 607 391 A1 | 11/2006 |
| CN | 1170356 A | 1/1998 |
| CN | 1882556 A | 12/2006 |
| CN | 101317821 A | 12/2008 |
| DE | 10214264 A1 | 10/2003 |
| EP | 0 416 950 A1 | 3/1991 |
| EP | 0 416 951 A1 | 3/1991 |
| EP | 0 418 716 A1 | 3/1991 |
| EP | 1 504 760 B1 | 10/1996 |
| EP | 1 621 197 A2 | 4/2003 |
| EP | 1 408 967 B1 | 4/2004 |
| EP | 1 530 471 B1 | 5/2005 |
| EP | 1 570 861 A2 | 9/2005 |
| EP | 1 651 270 B1 | 3/2007 |
| EP | 1 894 568 A1 | 3/2008 |
| EP | 1 925 293 A2 | 5/2008 |
| EP | 1 718 336 B1 | 6/2008 |
| EP | 1 651 221 B1 | 1/2009 |
| EP | 2 036 572 A1 | 3/2009 |
| EP | 1 917 369 B1 | 8/2009 |
| EP | 2 098 248 A1 | 9/2009 |
| EP | 1 007 017 B2 | 12/2010 |
| EP | 1 755 590 B1 | 8/2011 |
| EP | 1 651 224 B1 | 10/2011 |
| EP | 1 019 021 B2 | 12/2012 |
| EP | 2 037 879 B1 | 5/2013 |
| JP | 2000-513340 A | 10/2000 |
| JP | 2003-525842 A | 9/2003 |
| JP | 2004-514504 A | 5/2004 |
| JP | 2007-520506 A | 7/2007 |
| JP | 2007-520508 A | 7/2007 |
| JP | 2008-503500 A | 2/2008 |
| JP | 2008-521788 A | 6/2008 |
| JP | 2008-534611 A | 8/2008 |
| JP | 2012-513311 A | 6/2012 |
| RU | 2 319 512 C2 | 3/2008 |
| WO | 1986/003750 A1 | 7/1986 |
| WO | 1991/014468 A1 | 10/1991 |
| WO | 1992/004365 A1 | 3/1992 |
| WO | 1992/016528 A1 | 10/1992 |
| WO | 1993/011773 A1 | 6/1993 |
| WO | 1995/005805 A1 | 3/1995 |
| WO | 1995/015151 A1 | 6/1995 |
| WO | 1996/019198 A1 | 6/1996 |
| WO | 1996/032149 A1 | 10/1996 |
| WO | 1996/032344 A1 | 10/1996 |
| WO | 1997/038741 A1 | 10/1997 |
| WO | 1997/039758 A1 | 10/1997 |
| WO | 1997/044080 A1 | 11/1997 |
| WO | 1998/015280 A1 | 4/1998 |
| WO | 1998/041193 A1 | 9/1998 |
| WO | 1999/015182 A1 | 4/1999 |
| WO | 1999/016422 A1 | 4/1999 |
| WO | 2000/032165 A1 | 6/2000 |
| WO | 2000/035441 A2 | 6/2000 |
| WO | 2000/036915 A1 | 6/2000 |
| WO | 2000/053157 A1 | 9/2000 |
| WO | 2000/053187 A1 | 9/2000 |
| WO | 2000/061108 A1 | 10/2000 |
| WO | 2000/069468 A1 | 11/2000 |
| WO | 2001/00312 A1 | 1/2001 |
| WO | 2001/004118 A2 | 1/2001 |
| WO | 2001/054664 A1 | 8/2001 |
| WO | 2001/076575 A2 | 10/2001 |
| WO | 2002/014293 A1 | 2/2002 |
| WO | 2002/078671 A1 | 10/2002 |
| WO | 2002/85326 A2 | 10/2002 |
| WO | 2004/014293 A2 | 2/2004 |
| WO | 2004/018025 A1 | 3/2004 |
| WO | 2004/105759 A2 | 12/2004 |
| WO | 2005/000267 A2 | 1/2005 |
| WO | 2005/013994 A1 | 2/2005 |
| WO | 2005/014005 A1 | 2/2005 |
| WO | 2005/065435 A2 | 7/2005 |
| WO | 2005/074900 A1 | 8/2005 |
| WO | 2005/110402 A1 | 11/2005 |
| WO | 2006/114379 A1 | 11/2006 |
| WO | 2006/128847 A2 | 12/2006 |
| WO | 2007/009164 A1 | 1/2007 |
| WO | 2007/011989 A2 | 1/2007 |
| WO | 2007/057219 A1 | 5/2007 |
| WO | 2007/057221 A1 | 5/2007 |
| WO | 2007/057222 A1 | 5/2007 |
| WO | 2007/057223 A1 | 5/2007 |
| WO | 2007/095041 A1 | 8/2007 |
| WO | 2007/134964 A1 | 11/2007 |
| WO | 2008/000482 A1 | 1/2008 |
| WO | 2008/014161 A2 | 1/2008 |
| WO | 2008/025787 A2 | 3/2008 |
| WO | 2008/102128 A2 | 8/2008 |
| WO | 2009/074662 A2 | 6/2009 |
| WO | 2009/095681 A2 | 8/2009 |
| WO | 2010/097188 A1 | 9/2010 |
| WO | 2010/138862 A2 | 12/2010 |
| WO | 2010/138868 A2 | 12/2010 |
| WO | 2010/138884 A2 | 12/2010 |
| WO | 2011/120779 A1 | 10/2011 |
| WO | 2012/051426 A2 | 4/2012 |
| WO | 2012/110770 A2 | 8/2012 |
| WO | 2012/0120284 A1 | 9/2012 |
| WO | 2012/158166 A1 | 11/2012 |

OTHER PUBLICATIONS

Applicant Initiated Interview Summary, dated Aug. 2, 2012, for U.S. Appl. No. 13/281,726, 6 pages.
Applicant Initiated Interview Summary, dated Dec. 12, 2012, for U.S. Appl. No. 12/790,448, 3 pages.
Applicant Initiated Interview Summary, dated Dec. 20, 2012, for U.S. Appl. No. 12/790,605, 3 pages.
Applicant Initiated Interview Summary, dated Feb. 22, 2013, for co-pending U.S. Appl. No. 12/790,448, 3 pages.
Applicant Initiated Interview Summary, dated Oct. 28, 2013, for U.S. Appl. No. 13/692,904, 3 pages.
Applicant Initiated Interview Summary, dated Sep. 27, 2012, for U.S. Appl. No. 13/281,726, 3 pages.
Applicant Initiated Interview Summary, dated May 22, 2012 in corresponding U.S. Appl. No. 12/790,671, 3 pages.
Applicant Initiated Interview Summary, dated May 23, 2012, for corresponding U.S. Appl. No. 12/790,605, 3 pages.
Argentinian Preliminary Office Action, dated Aug. 17, 2018, for Argentinian Application No. 20100101882, 6 pages.
Argentinian Preliminary Office Action, dated Aug. 17, 2018, for Argentinian Application No. 20100101884, 7 pages.
Argentinian Preliminary Office Action, dated Aug. 17, 2018, for Argentinian Application No. 20100101885, 7 pages.
Australian Examination Report dated Dec. 17, 2015, for corresponding Australian Patent Application No. 2015201037, 4 pages.
Australian Examination Report dated Jan. 15, 2018, for corresponding Australian Patent Application No. 2017201626, 7 pages.
Australian Examination Report dated Jan. 4, 2018, for corresponding Australian Patent Application No. 2017201709, 4 pages.
Australian Examination Report dated Jun. 29, 2015 for corresponding Australian Patent Application No. 2011368334, 3 pages.
Australian Examination Report dated Mar. 10, 2016, for corresponding Australian Patent Application No. 2015201864, 5 pages.
Australian Examination Report dated May 12, 2016, for corresponding Australian Patent Application No. 2015201221, 4 pages.
Australian Notification of Allowance dated Sep. 8, 2015 for corresponding Australian Patent Application No. 2010253950, 1 page.

(56) References Cited

OTHER PUBLICATIONS

Baculard, "Place du Bronchodual® dans le traitement de fond de l'asthme de l'enfant," *Arch Péditar* 2(Suppl 2):149s-153s, 1995.
Barnes, "Chronic obstructive pulmonary disease: new opportunities for drug development," *Trends in Pharmacological Sciences* 19:415-423, 1998.
Barnes, "Efficacy of Inhaled Corticosteroids in Asthma," *Allergy Clin Immunol* 102:531-538 1998.
Beck, "Utilisation du bromure d'ipratropium par voie inhalée pour de traitment de l'asthme aigu chez l'enfant Expérience Clinique,"*Arch Pédiatar* 2(Suppl 2):145s-148s, 1995.
Blondino et al., "Surfactant Dissolution and Water Solubilization in Chlorine-Free Liquified Gas Propellants," Drug Development and Industrial Pharmacy, pp. 935-945, 1998.
Braga et al., "Making crystals from crystals: a green route to crystal engineering and polymorphism," *Chem Comm*, pp. 3635-3645, 2005.
Brambilla et al., "Modulation of aerosol clouds produced by pressurised inhalation aerosols," *International Journal of Pharmaceutics* 186:53-61, 1999.
Canadian Notice of Allowance, dated Feb. 15, 2017, for corresponding Canadian Patent Application No. 2,763,936, 1 page.
Canadian Office Action, dated Apr. 14, 2016, for corresponding Canadian Patent Application No. 2,763,936, 4 pages.
Canadian Office Action, dated Aug. 12, 2015, for corresponding Canadian Patent Application No. 2,763,939, 3 pages.
Canadian Office Action, dated May 11, 2016, for corresponding Canadian Patent Application No. 2,763,941, 7 pages.
Canadian Office Action, dated Nov. 3, 2016, for corresponding Canadian Patent Application No. 2,763,936, 5 pages.
Capraz et al., "The Effect of Inhaled Budesonide and Formoterol on Bronchial Remodeling and HRCT Features in Young Asthmatics," *Lung* 185:89-96, 2007.
Cazzola et al., "Incremental Benefit of Adding Oxitropium Bromide to Formoterol in Patients with Stable COPD," *Pulmonary Pharmacology & Therapeutics* 12:267-271, 1999.
Chinese Office Action, dated Jan. 17, 2018, for corresponding Chinese Patent Application No. 201510450391.1, 39 pages (with English translation).
Chinese Office Action, dated Jul. 19, 2017, for corresponding Chinese Patent Application No. 201510450391.1, 17 pages (with English translation).
Chinese Office Action, dated Aug. 12, 2016, for corresponding Chinese Patent Application No. 201080033310.3, 20 pages. (with English Translation).
Chinese Office Action, dated Dec. 28, 2015, for corresponding Chinese Patent Application No. 201080033118, 8 pages. (with English Translation).
Chinese Office Action, dated Feb. 13, 2017, for corresponding Chinese Patent Application No. 201080033310.3, 8 pages (with English Translation).
Chinese Office Action, dated Jan. 16, 2015, for corresponding Chinese Patent Application No. 201080033310.3, 9 pages. (with English Translation).
Chinese Office Action, dated Jun. 27, 2014, for corresponding Chinese Patent Application No. 201080033310.3, 17 pages. (with English Translation).
Chinese Office Action, dated Jun. 30, 2015, for corresponding Chinese Patent Application No. 201080033311.8, 7 pages. (with English Translation).
Columbian Office Action dated Jan. 21, 2016, for corresponding Columbian Application No. 15.302538, 2 pages. (translation only).
Cummings et al., "Performance Advantages of Co-Suspension Formulation Technology for Manufacturing of Metered Dose Inhalers" *RDD Europe 2011—Respiratory Drug Delivery vol. 2*, pp. 387-390, published by Virginia Commonwealth University 2011. (from client—added Jun. 9,2016—presented at RDD Conference 2011).

Cydulka et al., "Effects of Combined Treatment with Glycopyrrolate and Albuterol in Acute Exacerbation of Chronic Obstructive Pulmonary Disease," *Annals of Emergency Medicine* 25:470-473, 1995.
Da Rocha et al., "Science and Technology of Pressurized Metered-Dose Inhalers," *Controlled Pulmonary Drug Delivery*, Chapter 8, pp. 165-201, 2011.
Dellamary et al., "Hollow Porous Particles in Metered Dose Inhalers," *Pharmaceutical Research* 17(2):168-174, 2000.
Drugs Information Online, "FDA Approves Symbicort: Astrazeneca's Symbicort (budesonide/formoterol) Treatment For Asthma Approved by The FDA," retrieved on Oct. 28, 2013, from www.Drugs.com, Jul. 22, 2006, 2 pages.
Duddu et al., "Improved Lung Delivery from a Passive Dry Powder Inhaler Using an Engineered PulmoSphere Powder," *Pharmaceutical Research* 19(5):689-695 2002.
Ecuador Opposition filed by Asociacion De Laboratorios Farmaceuticos (ALAFAR) on May 21, 2015 against Ecuadorean Patent Application No. SP-2013-13082, 16 pages. (with translation) (Assoc. notified Nov. 17, 2015).
Ecuador Opposition filed by Roddome Pharmaceutical S.A. on May 7, 2015 against Ecuadorean Patent Application No. SP-2013-13082, 18 pages. (with translation).
Edwards et al., "Large Porous Particles for Pulmonary Drug Delivery", Science 276, 1868-1871 (1997), 5 pages. (from BLS).
Encyclopedia of Medicaments, M., RLS, p. 952, article Formoterol, pp. 642-643. (without English Abstract).
Eurasian Office Action dated Dec. 9, 2015, for corresponding Eurasian Patent Application No. 210490991, 4 pages. (with translation).
European Communication under Rule 71(3) EPC, for Application No. 10 721 258.1-1453, dated Jul. 17, 2015, 5 pages.
European Communication under Rule 71(3) EPC, for Application No. 10 727 551.3-1453, dated Jul. 14, 2015, 7 pages.
European Communication under Rule 71(3) EPC, for Application No. 10 727 553.9-1453, dated Jul. 14, 2015, 5 pages.
European Intention to Grant dated Dec. 11, 2015, for corresponding European Application No. 10 721 258.1, 7 pages.
European Intention to Grant dated Dec. 11, 2015, for corresponding European Application No. 10 727 551.3, 5 pages.
European Intention to Grant dated Dec. 11, 2015, for corresponding European Application No. 10 727 553.9, 7 pages.
European Search Report, dated Nov. 21, 2016, for corresponding European Patent Application No. 16164845.6, 9 pages.
European Search Report, dated Nov. 21, 2016, for corresponding European Patent Application No. 16164849.8, 10 pages.
European Search Report, dated Nov. 23, 2016, for corresponding European Patent Application No. 16164844.9, 7 pages.
Final Office Action dated Sep. 1, 2015 for corresponding U.S. Appl. No. 14/334,503, 6 pages.
Final Office Action, dated Oct. 21, 2016 for U.S. Appl. No. 14/285,435, 10 pages.
Final Office Action, dated Apr. 11, 2012, for U.S. Appl. No. 12/790,671, 17 pages.
Final Office Action, dated Dec. 20, 2016, for U.S. Appl. No. 14/327,425, 19 pages.
Final Office Action, dated Jan. 27, 2016, for U.S. Appl. No. 14/327,425, 15 pages.
Final Office Action, dated Mar. 13, 2015, for U.S. Appl. No. 12/790,710, 23 pages.
Final Office Action, dated May 3, 2017, for co-pending U.S. Appl. No. 12/790,710, 16 pages.
Final Office Action, dated Nov. 24, 2014, for U.S. Appl. No. 12/790,448, 21 pages.
Final Office Action, dated Oct. 22, 2015, for U.S. Appl. No. 12/790,671, 23 pages.
Geller et al., "Development of an Inhaled Dry-Powder Formulation of Tobramycin Using PulmoSphere™ Technology", Journal of Aerosol Medicine and Pulmonary Drug Delivery, vol. 24, No. 4, 2011, pp. 175-182, 8 pages. (from BLS).
Hansel et al., "Glycopyrrolate Causes Prolonged Bronchoprotection and Bronchodilatation in Patients with Asthma," *Chest* 128:1974-1979, 2005.

(56) References Cited

OTHER PUBLICATIONS

Hartman et al., "The Efficiency and Stability of a Novel Lipid-based Budesonide Metered Dose Inhaler Formulation Utilizing HFA," AAPS Annual Meeting and Exposition, Salt Lake City, UT, Oct. 26-30, 2003, 1 page.
Hirst et al., "In Vivo Lung Deposition of Hollow Porous Particles from a Pressurized Metered Dose Inhaler," *Pharmaceutical Research* 19(3):258-264, 2002.
Hoye et al., "Measurement and Correlation of Solute Solubility in HFA-134a/Ethanol Systems," *International Journal of Pharmaceutics* 362:184-188, 2008.
Indian Examination Report dated May 14, 2018, for corresponding Indian Application No. 9296/DELNP/2011, 7 pages (with English translation).
Indian Examination Report dated Sep. 19, 2018, for corresponding Indian Application No. 9299/DELNP/2011, 6 pages (with English translation).
Indian First Examination Report dated Oct. 10, 2017, for corresponding Indian Application No. 9301/DELNP/2011, 6 pages (with English translation).
Indonesian Notice of Allowance dated Oct. 23, 2017 for corresponding Indonesian Patent Application No. W-00201104346, 4 pages (with English translation).
International Preliminary Report on Patentability dated Nov. 24, 2015, for corresponding Patent Application No. PCT/US2014/039234, 8 pages.
International Preliminary Report on Patentability, dated Nov. 19, 2013, for International Application No. PCT/US2011/036868, 8 pages.
International Preliminary Report on Patentability, dated Nov. 29, 2011, for International Application No. PCT/US2010/036650, 10 pages.
International Preliminary Report on Patentability, dated Nov. 29, 2011, for International Application No. PCT/US2010/036676, 9 pages.
International Preliminary Report on Patentability, dated Dec. 8, 2011, for International Application No. PCT/US2010/036659, 11 pages.
International Search Report, dated Aug. 12, 2011, for International Application No. PCT/US2011/036868, 8 pages.
International Search Report, dated Feb. 25, 2011, for International Application No. PCT/US2010/036650, 5 pages.
International Search Report, dated Feb. 25, 2011, for International Application No. PCT/US2010/036659, 5 pages.
International Search Report, dated Feb. 25, 2011, for International Application No. PCT/US2010/036676, 5 pages.
International Search Report, dated Sep. 2, 2014, for corresponding International Application No. PCT/US2014/039234, 12 pages.
Israeli Examination Report dated Jan. 5, 2017, for corresponding Israeli Application No. 216466, 3 pages (English translation only).
Israeli Examination Report dated Jul. 17, 2017, for corresponding Israeli Application No. 216466, 4 pages (with English translation).
Israeli Examination Report dated Jul. 17, 2017, for corresponding Israeli Application No. 216467, 6 pages (English translation only).
Israeli Examination Report dated Jul. 23, 2017, for corresponding Israeli Application No. 216468, 6 pages (with English translation).
Israeli Notification of Defects dated Dec. 13, 2015, for corresponding Israeli Patent Application No. 216467, 2 pages (English translation only).
Israeli Notification of Defects dated Dec. 13, 2015, for corresponding Israeli Patent Application No. 216468, 3 pages (English translation only).
Israeli Notification of Defects dated Dec. 16, 2015, for corresponding Israeli Patent Application No. 216466, 3 pages (English translation only).
Israeli Notification of Defects dated Feb. 8, 2016, for corresponding Israeli Application No. 229260, 3 pages (English translation only).
James et al., "The surface characterization and comparison of two potential sub-micron, sugar bulking excipients for use in low-dose, suspension formulations in metered dose inhalers," *International Journal of Pharmaceutics* 361(1-2):209-221, 2008.
Japanese Notice of Allowance dated Dec. 17, 2015, for corresponding Japanese Patent Application No. 2012-513311, 4 pages. (with translation).
Japanese Notice of Allowance dated Dec. 17, 2015, for corresponding Japanese Patent Application No. 2012-513319, 5 pages. (with translation).
Japanese Notice of Allowance dated Sep. 2, 2015 for corresponding Japanese Patent Application No. 2012-513314, 4 pages. (with English translation).
Japanese Office Action dated Mar. 22, 2016 for corresponding Japanese Application No. 2015-084226, 7 pages, (with English translation).
Japanese Office Action dated Mar. 22, 2016 for corresponding Japanese Application No. 2015-084240, 6 pages, (with English translation).
Japanese Office Action, dated Apr. 28, 2015, for corresponding Japanese Application No. 2012-513314, 8 pages. (with English translation).
Japanese Office Action, dated Dec. 16, 2014, for corresponding Japanese Patent Application No. 2012-513319, 4 pages. (English translation only).
Japanese Office Action, dated Jan. 27, 2015, for corresponding Japanese Patent Application No. 2014-511329, 5 pages. (with English translation).
Japanese Office Action, dated Jul. 1, 2014, for corresponding Japanese Patent Application No. 2012-513319, 8 pages. (with English Translation).
Japanese Office Action, dated Oct. 30, 2018, for Japanese Application No. 2017-125969, 5 pages. (with English Translation).
Japanese Office Action, dated Aug. 9, 2016, for corresponding Japanese Patent Application No. 2015-199079, 9 pages. (with English translation).
Japanese Office Action, dated Jan. 17, 2017, for corresponding Japanese Application No. 2015-084240, 7 pages (with English translation).
Japanese Office Action, dated Mar. 26, 2019, for corresponding Japanese Patent Application No. 2017-188628, 4 pages.
Japanese Office Action, dated May 30, 2017, for corresponding Japanese Patent Application No. 2015-199079, 8 pages (with English Translation).
Japanese Office Action, dated Nov. 8, 2016, for corresponding Japanese Patent Application No. 2015-084226, 6 pages. (with English translation).
Johnson et al., "Effect of Inhaled glycopyrrolate and atropine in asthma. Precipitated by exercise and cold air inhalation," *Chest* 85(3):325-328, 1984.
Joshi et al., "Development of Mono, Dual, and Triple Combination pMDIs without Co-formulation Effect" RDD Europe 2011—Respiratory Drug Delivery vol. 2, pp. 383-386, published by Virginia Commonwealth University 2011. (from client added Jun. 9, 2016, presented at RDD Conference 2011).
Korean Notice of Allowance, dated Aug. 30, 2018, for Korean Application No. 10-2017-7024590, 7 pages.
Korean Notice of Grounds for Rejection dated Apr. 27, 2018 for corresponding Korean Application No. 10-2011-7028583, 6 pages (with English translation).
Korean Office Action dated Jul. 31, 2017 for corresponding Korean Application No. 10-2011-7028582, 6 pages (with English translation).
Korean Office Action dated Nov. 17, 2017 for corresponding Korean Application No. 10-2017-7024590, 8 pages (with English translation).
Korean Office Action, dated Aug. 29, 2016, for corresponding Korean Patent Application 2011-7028551, 15 pages. (with English translation).
Korean Office Action, dated Jun. 15, 2017, for corresponding Korean Application No. 10-2011-7028583, 25 pages (with English translation).
Korean Office Action, dated Sep. 13, 2016, for corresponding Korean Patent Application 2011-7028582, 13 pages. (with English translation).

(56) References Cited

OTHER PUBLICATIONS

Korean Office Action, dated Sep. 4, 2017, for corresponding Korean Patent Application No. 10-2017-7016074, 6 pages (with English translation).
Lechuga-Ballessteros et al., "Residual Water in Amorphous Solids, Measurement and Effects on Stability," In Progress in Amorphous Food and Pharmaceutical Systems, Levine, H., Ed. The Royal Society of Chemistry; London, pp. 275-316, 2002.
Lechuga-Ballesteros, et al., "A New Co-Suspension MDI Platform: Scientific Foundations of Mono, Dual and Triple Combination Products" RDD Europe 2011—Respiratory Drug Delivery vol. 1, pp. 101-112, published by Virginia Commonwealth University 2011. (from client added Jun. 9, 2016, presented at RDD Europe 2011 Conference).
Lechuga-Ballesteros, et al., "Dose Proportionality in a Triple Therapy Cosuspension pMDI with Multiple Strengths of an Inhaled Corticosteroid" RDD Europe 2013—Respiratory Drug Delivery vol. 2, pp. 339-342, published by Virginia Commonwealth University 2013. (from client added Jun. 9, 2016, presented at RDD Europe 2013 Conference).
Lechuga-Ballesteros, et al., "Novel cosuspension metered-dose inhalers for the combination therapy of chronic obstructive pulmonary disease and asthma," Future Med. Chem. 3(13):1703-1718, 2011.
Leckie et al., "Novel Therapy for COPD," *Exp. Opin. Invest. Drugs* 9(1):3-23, 2000.
Liao Yonghong et al., "Advances in Studies of Pressurized Metered-dose Formulations Containing Hydrofluoroalkane Propellants", *Acta Pharmaceutica Sinica* 41(3), 197-202, Dec. 31, 2006, 10 pages. (Translation only).
Mahler et al., "Effectiveness of Fluticasone Propionate and Salmeterol Combination Delivered via the Diskus Device in the Treatment of Chronic Obstructive Pulmonary Disease," *Am J Respir Crit Care Med* 166:1084-1091, 2002.
Mexican Office Action, dated Apr. 19, 2017, for corresponding Mexican Application No. MX/a/2011/012684, 7 pages (with English translation).
Mexican Office Action, dated Apr. 21, 2017, for corresponding Mexican Application No. MX/a/2011/012685, 7 pages (with English translation).
Miller, "The Effects of Water on Suspension Aerosol Formulations," *Respiratory Drug Delivery*, CRC Press, p. 250, 1990, 3 pages.
New Zealand Examination Report dated Nov. 25, 2015, for corresponding New Zealand Patent Application No. 617714, 1 page.
New Zealand First Examination Report dated Mar. 3, 2016, for corresponding New Zealand Application No. 716787, 2 pages.
New Zealand Further Examination Report dated Mar. 3, 2016, for corresponding New Zealand Application No. 617714, 2 pages.
Newhouse et al., "Inhalation of a Dry Powder Tobramycin PulmoSphere Formulation in Healthy Volunteers," *Chest* 124:360-366, 2003.
Newman, "Principles of Metered-Dose Inhaler Design", *Respiratory Care*, 2005, 59(9):1177-1190.
Noga et al., "Product Performance, Stability and Dose Proportionality of Glycopyrrolate Metered Dose Inhaler with Sub-Microgram Doses Using cosuspension Technology" RDD 2012 Arizona—Respiratory Drug Delivery vol. 2, pp. 645-648, published by Virginia Commonwealth University 2012. (from client added Jun. 9, 2016, presented at Arizona RDD Conference).
Non-Final Office Action dated Feb. 22, 2018 in co-pending U.S. Appl. No. 15/624,597, 12 pages.
Non-Final Office Action dated Jun. 27, 2018 in co-pending U.S. Appl. No. 15/151,174, 6 pages.
Non-Final Office Action dated Dec. 4, 2017 in co-pending U.S. Appl. No. 15/151,174, 6 pages.
Non-Final Office Action dated Aug. 17, 2017, for corresponding U.S. Appl. No. 15/135,389, 16 pages.
Non-Final Office Action dated Dec. 15, 2017, for corresponding U.S. Appl. No. 15/252,001, 35 pages.
Non-Final Office Action dated Jan. 24, 2017, for corresponding U.S. Appl. No. 15/135,389, 10 pages.
Non-Final Office Action dated May 13, 2019, for U.S. Appl. No. 15/932,249, 35 pages.
Non-Final Office Action, dated Feb. 19, 2014, for U.S. Appl. No. 12/790,671, 22 pages.
Notice of Allowance dated Jun. 27, 2016 for U.S. Appl. No. 12/790,448, 7 pages.
Notice of Allowance dated Jun. 27, 2016 for U.S. Appl. No. 14/334,503, 5 pages.
Notice of Allowance, dated Apr. 9, 2014, U.S. Appl. No. 12/790,605, 11 pages.
Notice of Allowance, dated Aug. 2, 2012, for U.S. Appl. No. 13/281,726, 5 pages.
Notice of Allowance, dated Oct. 28, 2013, for U.S. Appl. No. 13/692,904, 13 pages.
Notification to Grant the Patent Right, dated Jul. 15, 2016, for corresponding Chinese Patent Application No. 201080033311.8, 2 pages. (with English translation).
Office Action, dated Aug. 6, 2015 for U.S. Appl. No. 12/790,448, 29 pages.
Office Action, dated Apr. 21, 2016 for U.S. Appl. No. 14/285,435, 7 pages.
Office Action, dated Dec. 17, 2014, for U.S. Appl. No. 14/334,503, 14 pages.
Office Action, dated Jul. 13, 2016, for U.S. Appl. No. 12/790,710, 23 pages.
Office Action, dated Mar. 28, 2013, for co-pending U.S. Appl. No. 13/692,904, 12 pages.
Office Action, dated May 7, 2012, for co-pending U.S. Appl. No. 12/790,448, 30 pages.
Office Action, dated Nov. 20, 2013, for U.S. Appl. No. 12/790,710, 19 pages.
Office Action, dated Oct. 16, 2012, for co-pending U.S. Appl. No. 12/790,448, 18 pages.
Office Action, dated Oct. 31, 2013, for U.S. Appl. No. 13/109,884, 16 pages.
Office Action, dated Sep. 6, 2013, for corresponding U.S. Appl. No. 12/790,605, 18 pages.
Office Action, dated Apr. 10, 2015, for U.S. Appl. No. 12/790,671, 16 pages.
Office Action, dated Aug. 16, 2012, for corresponding U.S. Appl. No. 12/790,605, 14 pages.
Office Action, dated Feb. 17, 2012, for U.S. Appl. No. 13/281,726, 27 pages.
Office Action, dated Mar. 1, 2012, for corresponding U.S. Appl. No. 12/790,605, 11 pages.
Office Action, dated May 1, 2015, for U.S. Appl. No. 14/327,425, 15 pages.
Office Action, dated Nov. 14, 2011, for U.S. Appl. No. 12/790,671, 14 pages.
Oxis Turbuhaler, *RLS Drug Directory Encyclopedia*, downloaded Nov. 9, 2015, 18 pages, http://www.rlsnet.ru/tn_index_id_12220.htm. (with translation).
Panettieri et al., "Comparison of the efficacy and safety of arformoterol 15 microg twice daily and arformoterol 30 microg once daily in CORD: a single-dose, multicenter, randomized, modified-blind, two crossover study," *Clin. Ther*. 31(8): 1716-1723, Aug. 2009. (Abstract Only).
Philippine Examination Report, dated Jan. 11, 2018, for Philippine Application No. 1/2011/502406, 3 pages.
Philippine Examination Report, dated Nov. 23, 2018, for Philippine Application No. 1/2011/502406, 2 pages.
Ridder et al., "Surfactant solubility and aggregate orientation in hydrofluoroalkanes," *International Journal of Pharmaceutics* 295:57-65, 2005.
Rogueda, "Novel hydrofluoroalkane suspension formulations for respiratory drug delivery," *Expert Opin. Drug Deliv.* 2(4):625-638, 2005.
Russian Decision on Grant dated Jan. 11, 2016, for corresponding Russian Patent Application No. 2011154148/15, 54 pages. (with translation).
Russian Decision on Grant dated Nov. 2, 2015, for corresponding Russian Patent Application No. 2011154083/15, 30 pages. (with translation).

(56) References Cited

OTHER PUBLICATIONS

Russian Decision on Grant dated Aug. 27, 2015 for corresponding Russian Patent Application No. 2011152960, 27 pages. (English Translation Only).
Russian Office Action, dated Feb. 26, 2014, for corresponding Russian Application No. 2011154083/15, 6 pages. (English Translation Only).
Russian Office Action, dated Jul. 11, 2014, for corresponding Russian Application No. 2011152960, 8 pages.
Russian Office Action, dated May 27, 2015, for corresponding Russian Application No. 20111154148/15(081430), 9 pages. (English Translation Only).
Russian Office Action, dated May 7, 2015 for corresponding Russian Application No. 2013155903/15(087185), 12 pages. (with English Translation).
Schroeckenstein et al., "Twelve-hour bronchodilation in asthma with a single aerosol dose of the anticholinergic compound glycopyrrolate," *J Allergy Clin. Immunol.* 82(1):115-119, 1988.
Seddon, "Pseudopolymorph: a Polemic," *Crystal Growth & Design* 4(6):1087, 2004, 2 pages.
Singapore Search and Examination Report, dated Sep. 29, 2016, for corresponding Singapore Patent Application 2013083431, 14 pages.
Singapore Search Report, dated Jul. 3, 2015 for corresponding Singapore Patent Application No. 2013083431, 10 pages.
Singapore Written Opinion, dated Apr. 11, 2016 for corresponding Singapore Patent Application No. 2013083431, 13 pages.
Singapore Written Opinion, dated Jul. 3, 2015 for corresponding Singapore Patent Application No. 2013083431, 12 pages.
Singapore Written Opinion, dated Sep. 9, 2016, for corresponding Singapore Patent Application 11201509543Y, 5 pages.
Singh et al., "NVA237, a once-daily inhaled antimuscarin moderate-to-severe COPD," presented at the American Thoracic Society International Conference, San Diego, California, May 19-24, 2006, poster, 2 pages.
Skorodin, "Pharmacotherapy for Asthma and Chronic Obstructive Pulmonary Disease," *Arch. Intern. Med.* 153:814-828, 1993.
Swarbrick Science Press, Encyclopedia of Pharmaceutical Technology, Jan. 31, 2009, 6 pages. (Translation only).
Taiwan Notice of Allowance dated Jun. 29, 2018, for corresponding Taiwanese Patent Application No. 105116641, 3 pages (with English translation).
Taiwan Office Action dated Apr. 20, 2018, for corresponding Taiwanese Patent Application No. 105111487, 4 pages (with English translation).
Taiwan Office Action dated Aug. 24, 2017, for corresponding Taiwanese Patent Application No. 105111487, 9 pages (with English translation).
Taiwan Office Action dated Aug. 28, 2017, for corresponding Taiwanese Patent Application No. 105116641, 7 pages (with English translation).
Taiwanese Office Action, dated Apr. 25, 2016 for corresponding Taiwanese Patent Application No. 099117221, 8 pages. (with English translation).
Taiwanese Office Action, dated Jul. 17, 2015 for corresponding Taiwanese Patent Application No. 099117219, 16 pages. (with English translation).
Tarara et al., "Characterization of Suspension-Based Metered Dose Inhaler Formulations Composed of Spray-Dried Budesonide Microcrystals Dispersed in HFA-134a," *Pharmaceutical Research* 21(9):1607-1614, 2004.
Telko et al., "Dry Powder Inhaler Formulation", *Respiratory Care*, 2005, 50(9):1209-1227.
Troy (Eds.), "Remington: The Science and Practice of Pharmacy," Table 16-1, $21^{st}$ Edition, *Williams & Wilkins*, p. 212, 2006, 3 pages.
Ukrainian Office Action, dated Jun. 11, 2015, for corresponding Ukrainian Application No. a 2013 13538, 8 pages. (with English Translation).
Vehring et al., "Cosuspensions of Microcrystals and Engineered Microparticles for uniform and Efficient Delivery of Respiratory Therapeutics from Pressurized Metered Dose Inhalers," *Langmuir* 28:15015-15023, 2012.
Vervaet et al., "Drug-surfactant-propellant interactions in HFA-formulations," *International Journal of Pharmaceutics* 186:13-30, 1999.
Vietnamese Office Action dated Apr. 13, 2016 for corresponding Vietnamese Patent Application No. 1-2015-04797, 1 page (English translation only).
Vippagunta et al., "Crystalline solids," *Advanced Drug Delivery Reviews* 48:3-26, 2001.
Walker et al., "Prolonged effect of inhaled glycopyrrolate in asthma," *Chest* 91(1)49-51, 1987.
Wermuth (Ed.), "The Practice of Medicinal Chemistry: Chapter 37, Preparation of Water-Soluble Compounds Through Salt Formulation," Academic Press, Third Edition, p. 758, 2008, 6 pages.
Wesseling et al., "A Comparison of the Effects of Anticholinergic and $\beta_2$-Agonist and Combination Therapy on Respiratory Impedance in COPD," *Chest* 101(1):166-173, 1992.
Young et al., "The influence of micronized particulates on the aerosolization properties of pressurized metered dose inhalers," *Aerosol Science* 40:324-337, 2009.
Zheng (ed.), "Formulation and Analytical Development for Low-Dose Oral Drug Products," John Wiley & Sons, Inc., Hoboken, New Jersey, Table 4.1, p. 65, 2009, 3 pages.
Argentinian Office Action dated Aug. 6, 2019, for corresponding Argentinian Application No. P100101882, 4 pages (English translation).
Argentinian Office Action dated Aug. 6, 2019, for corresponding Argentinian Application No. P100101884, 4 pages. (English translation).
Argentinian Office Action dated Aug. 6, 2019, for corresponding Argentinian Application No. P100101885, 4 pages (English translation).
Australian Examination Report dated Sep. 27, 2019, for corresponding Australian Application No. 2019203814, 3 pages.
Brazilian Office Action filed May 28, 2010, for corresponding Brazilian Application No. P11011220-0, 4 pages (English translation).
Chinese Office Action and Search Report, dated Oct. 31, 2019, for Chinese Application No. 201610862606.5, 26 pages (with English Translation).
Mexican Office Action dated Aug. 6, 2019, for corresponding Mexican Application No. MX/a/2017/011056, 6 pages.
Non-Final Office Action dated Oct. 17, 2019 for U.S. Appl. No. 16/228,397, 14 pages.
Philippine Subsequent Substantive Examination Report dated Sep. 9, 2019, for corresponding Philippine Application No. 1/2011/502405, 4 pages.
Philippine Subsequent Substantive Examination Report dated Sep. 20, 2019, for corresponding Philippine Application No. 1/2011/502282, 8 pages.
Russian Office Action dated Aug. 8, 2019, for corresponding Russian Application No. 2016107464, 3 pages (English translation).
Russian Office Action dated Sep. 27, 2019, for corresponding Russian Application No. 2016117972, 3 pages (English translation).

US 10,716,753 B2

COMPOSITIONS FOR PULMONARY DELIVERY OF LONG-ACTING MUSCARINIC ANTAGONISTS OR LONG-ACTING B2 ADRENERGIC RECEPTOR AGONISTS AND ASSOCIATED METHODS AND SYSTEMS

This application claims the benefit of priority of U.S. Provisional Application No. 61/182,565, filed May 29, 2009; U.S. Provisional Application No. 61/258,172, filed Nov. 4, 2009; U.S. Provisional Application No. 61/309,365, filed Mar. 1, 2010; and U.S. Provisional Application No. 61/345,536 filed May 17, 2010.

TECHNICAL FIELD

The present disclosure relates generally to pharmaceutical formulations and methods for delivery of active agents via the respiratory tract. In certain aspects, the present disclosure relates to compositions, methods, and systems for pulmonary delivery of long-acting muscarinic antagonists and long-acting $\beta_2$ adrenergic receptor agonists via a metered dose inhaler.

BACKGROUND

Methods of targeted drug delivery that deliver an active agent at the site of action are often desirable. For example, targeted delivery of active agents can reduce undesirable side effects, lower dosing requirements and decrease therapeutic costs. In the context of respiratory delivery, inhalers are well known devices for administering an active agent to a subject's respiratory tract, and several different inhaler systems are currently commercially available. Three common inhaler systems include dry powder inhalers, nebulizers and metered dose inhalers (MDIs).

MDIs may be used to deliver medicaments in a solubilized form or as a suspension. Typically, MDIs use a relatively high vapor pressure propellant to expel aerosolized droplets containing an active agent into the respiratory tract when the MDI is activated. Dry powder inhalers generally rely on the patient's inspiratory efforts to introduce a medicament in a dry powder form to the respiratory tract. On the other hand, nebulizers form a medicament aerosol to be inhaled by imparting energy to a liquid solution or suspension.

MDIs are active delivery devices that utilize the pressure generated by a propellant. Conventionally, chlorofluorocarbons (CFCs) have been used as propellants in MDI systems because of their low toxicity, desirable vapor pressure and suitability for formulation of stable suspensions. However, traditional CFC propellants are understood to have a negative environmental impact, which has led to the development of alternative propellants that are believed to be more environmentally-friendly, such as perfluorinated compounds (PFCs) and hydrofluoroalkanes (HFAs).

The active agent to be delivered by a suspension MDI is typically provided as a fine particulate dispersed within a propellant or combination of two or more propellants (i.e., a propellant "system"). In order to form the fine particulates, the active agent is typically micronized. Fine particles of active agent suspended in a propellant or propellant system tend to aggregate or flocculate rapidly. This is particularly true of active agents present in micronized form. In turn, aggregation or flocculation of these fine particles may complicate the delivery of the active agent. For example, aggregation or flocculation can lead to mechanical failures, such as those that might be caused by obstruction of the valve orifice of the aerosol container. Unwanted aggregation or flocculation of drug particles may also lead to rapid sedimentation or creaming of drug particles, and such behavior may result in inconsistent dose delivery, which can be particularly troublesome with highly potent, low dose medicaments. Another problem associated with such suspension MDI formulations relates to crystal growth of the drug during storage, resulting in a decrease over time of aerosol properties and delivered dose uniformity of such MDIs. More recently, solution approaches, such as those disclosed in U.S. Pat. No. 6,964,759, have been proposed for MDI formulations containing anticholinergics.

One approach to improve aerosol performance in dry powder inhalers has been to incorporate fine particle carrier particles, such as lactose. Use of such fine excipients has not been investigated to any great extent for MDIs. A recent report by Young et al., "The influence of micronized particulates on the aerosolization properties of pressurized metered dose inhalers"; Aerosol Science 40, pgs. 324-337 (2009), suggests that the use of such fine particle carriers in MDIs actually result in a decrease in aerosol performance.

In traditional CFC systems, when the active agent present in an MDI formulation is suspended in the propellant or propellant system, surfactants are often used to coat the surfaces of the active agent in order to minimize or prevent the problem of aggregation and maintain a substantially uniform dispersion. The use of surfactants in this manner is sometimes referred to as "stabilizing" the suspension. However, many surfactants that are soluble and thus effective in CFC systems are not effective in HFA and PFC propellant systems because such surfactants exhibit different solubility characteristics in non-CFC propellants.

DETAILED DESCRIPTION

Figure 1:
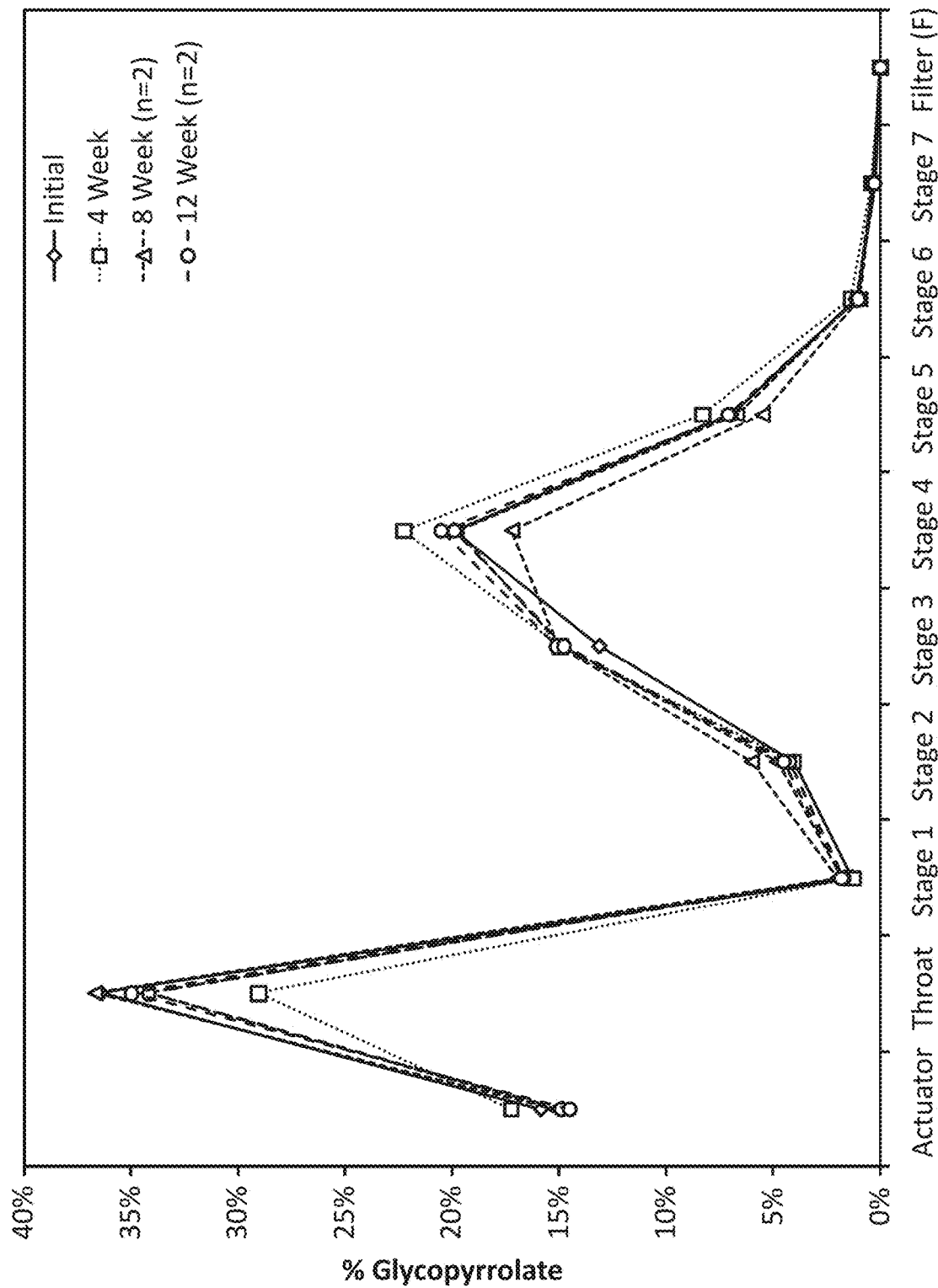
FIG. 1 is a graph, which depicts the particle size distribution exhibited by an exemplary co-suspension composition according to the present description, which included glycopyrrolate, a long-acting muscarinic antagonist, as the active agent. Co-suspension MDIs were subjected to temperature cycling conditions (alternating 6 h hold time at −5 or 40° C.) for 12 weeks.

The present disclosure provides compositions, methods, and systems for respiratory delivery of active agents via an MDI. In particular embodiments, the compositions, methods and systems described herein are adapted for respiratory delivery of active agents selected from a long-acting muscarinic antagonist ("LAMA") and a long-acting $\beta_2$ adrenergic receptor agonist ("LABA"). In certain embodiments, the LAMA or LABA active agent may be potent or highly potent and, therefore, formulated at low concentrations and delivered in low doses. The pharmaceutical compositions described herein may be formulated for pulmonary or nasal delivery via an MDI. The methods described herein include methods of stabilizing formulations including LAMA or LABA active agents for respiratory delivery, as well as methods for pulmonary delivery of LAMA and LABA active agents via an MDI. Also described herein are methods for preparing an MDI for delivery of a LAMA or LABA active agent.

In specific embodiments, the methods described herein include methods for treating a pulmonary disease or disorder amenable to treatment by delivery of a LAMA or LABA active agent through an MDI. For example, and the compositions, methods and systems described herein can be used to treat inflammatory or obstructive pulmonary diseases or conditions. In certain embodiments, the compositions, methods and systems described herein can be used to treat patients suffering from a disease or disorder selected from asthma, chronic obstructive pulmonary disease (COPD), exacerbation of airways hyper reactivity consequent to other drug therapy, allergic rhinitis, sinusitis, pulmonary vasoconstriction, inflammation, allergies, impeded respiration, respiratory distress syndrome, pulmonary hypertension, pulmonary vasoconstriction, and any other respiratory disease, condition, trait, genotype or phenotype that can respond to the administration of a LAMA or LABA, alone or in combination with other therapies. In certain embodiments, the compositions, systems and methods described herein can be used to treat pulmonary inflammation and obstruction associated with cystic fibrosis. As used herein, the terms "COPD" and "chronic obstructive pulmonary disease" encompass chronic obstructive lung disease (COLD), chronic obstructive airway disease (COAD), chronic airflow limitation (CAL) and chronic obstructive respiratory disease (CORD) and include chronic bronchitis, bronchiectasis, and emphysema. As used herein, the term "asthma" refers to asthma of whatever type or genesis, including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Asthma is also to be understood as embracing wheezy-infant syndrome.

It will be readily understood that the embodiments described herein are exemplary. The following more detailed description of various embodiments is not intended to limit the scope of the present disclosure, but is merely representative of various embodiments. Moreover, the order of the steps or actions of the methods described in connection with the embodiments disclosed herein may be changed by those skilled in the art without departing from the scope of the present disclosure. In other words, unless a specific order of steps or actions is required for proper operation of the embodiment, the order or use of specific steps or actions may be modified.

I. Definitions

Unless specifically defined otherwise, the technical terms, as used herein, have their normal meaning as understood in the art. The following terms are specifically defined for the sake of clarity.

The term "active agent" is used herein to include any agent, drug, compound, composition or other substance that may be used on, or administered to a human or animal and is a LAMA or LABA. The term "active agent" may be used interchangeably with the terms, "drug," "pharmaceutical," "medicament," "drug substance," or "therapeutic."

The terms "associate," "associate with" or "association" refers to an interaction or relationship between a chemical entity, composition, or structure in a condition of proximity to a surface, such as the surface of another chemical entity, composition, or structure. The association includes, for example, adsorption, adhesion, covalent bonding, hydrogen bonding, ionic bonding and electrostatic attraction, Lifshitz-van der Waals interactions and polar interactions. The term "adhere" or "adhesion" is a form of association and is used as a generic term for all forces tending to cause a particle or mass to be attracted to a surface. "Adhere" also refers to bringing and keeping particles in contact with each other, such that there is substantially no visible separation between particles due to their different buoyancies in a propellant under normal conditions. In one embodiment, a particle that attaches to or binds to a surface is encompassed by the term "adhere." Normal conditions may include storage at room temperature or under an accelerative force due to gravity. As described herein, active agent particles may associate with suspending particles to form a co-suspension, where there is substantially no visible separation between the suspending particles and the active agent particles or flocculates thereof due to differences in buoyancy within a propellant.

"Suspending particles" refer to a material or combination of materials that is acceptable for respiratory delivery, and acts as a vehicle for active agent particles. Suspending particles interact with the active agent particles to facilitate repeatable dosing, delivery or transport of active agent to the target site of delivery, i.e., the respiratory tract. The suspending particles described herein are dispersed within a suspension medium including a propellant or propellant system, and can be configured according to any shape, size or surface characteristic suited to achieving a desired suspension stability or active agent delivery performance. Exemplary suspending particles include particles that exhibit a particle size that facilitates respiratory delivery of active agent and have physical configurations suited to formulation and delivery of the stabilized suspensions as described herein.

The term "co-suspension" refers to a suspension of two or more types of particles having different compositions within a suspension medium, wherein one type of particle associates at least partially with one or more of the other particle types. The association leads to an observable change in one or more characteristics of at least one of the individual particle types suspended in the suspension medium. Characteristics modified by the association may include, for example, one or more of the rate of aggregation or flocculation, the rate and nature of separation, i.e. sedimentation or creaming, density of a cream or sediment layer, adhesion to container walls, adhesion to valve components, and rate and the level of dispersion upon agitation.

Exemplary methods for assessing whether a co-suspension is present can include the following: If one particle type has a pycnometric density greater than the propellant and another particle type has a pycnometric density lower than the propellant, a visual observation of the creaming or sedimentation behavior can be employed to determine the presence of a co-suspension. The term "pycnometric density" refers to the density of a material that makes up a particle, excluding voids within the particle. In one embodiment, the materials can be formulated or transferred into a transparent vial, typically a glass vial, for visual observation. After initial agitation the vial is left undisturbed for a sufficient time for formation of a sediment or cream layer, typically 24 hours. If the sediment or cream layer is observed to be completely or mostly a uniform single layer, a co-suspension is present. The term "co-suspension" includes partial co-suspensions, where a majority of the at least two particle types associate with each other, however, some separation (i.e., less than a majority) of the at least two particle types may be observed.

The exemplary co-suspension test may be performed at different propellant temperatures to accentuate the sedimentation or creaming behavior of particle types with a density close to the propellant density at room temperature. If the different particle types have the same nature of separation, i.e. all sediment or all cream, the presence of a co-suspension can be determined by measuring other characteristics of the suspension, such as rate of aggregation or flocculation, rate of separation, density of cream or sediment layer, adhesion to container walls, adhesion to valve components, and rate and level of dispersion upon agitation, and comparing them to the respective characteristics of the similarly suspended individual particle types. Various analytical methods generally known to those skilled in the art can be employed to measure these characteristics.

In the context of a composition containing or providing respirable aggregates, particles, drops, etc., such as compositions described herein, the term "fine particle dose" or "FPD" refers to the dose, either in total mass or fraction of the nominal dose or metered dose, that is within a respirable range. The dose that is within the respirable range is measured in vitro to be the dose that deposits beyond the throat stage of a cascade impactor, i.e., the sum of dose delivered at stages 3 through filter in a Next Generation Impactor operated at a flow rate of 30 l/min.

In the context of a composition containing or providing respirable aggregates, particles, drops, etc., such as compositions described herein, the term "fine particle fraction" or "FPF" refers to the proportion of the delivered material relative to the delivered dose (i.e., the amount that exits the actuator of a delivery device, such as an MDI) that is within a respirable range. The amount of delivered material within the respirable range is measured in vitro as the amount of material that deposits beyond the throat stage of a cascade impactor, e.g., the sum of the material delivered at stages 3 through filter in a Next Generation Impactor operated at a flow rate of 30 l/min.

As used herein, the term "inhibit" refers to a measurable lessening of the tendency of a phenomenon, symptom or condition to occur or the degree to which that phenomenon, symptom or condition occurs. The term "inhibit" or any form thereof, is used in its broadest sense and includes minimize, prevent, reduce, repress, suppress, curb, constrain, restrict, slow progress of and the like.

"Mass median aerodynamic diameter" or "MMAD" as used herein refers to the aerodynamic diameter of an aerosol below which 50% of the mass of the aerosol consists of particles with an aerodynamic diameter smaller than the MMAD, with the MMAD being calculated according to monograph 601 of the United States Pharmacopeia ("USP").

When referred to herein, the term "optical diameter" indicates the size of a particle as measured by the Fraunhofer diffraction mode using a laser diffraction particle size analyzer equipped with a dry powder dispenser (e.g., Sympatec GmbH, Clausthal-Zellerfeld, Germany).

The term solution mediated transformation refers to the phenomenon in which a more soluble form of a solid material (i.e. particles with small radius of curvature (a driving force for Ostwald ripening), or amorphous material) dissolves and recrystallizes into the more stable crystal form that can coexist in equilibrium with its saturated propellant solution.

A "patient" refers to an animal in which LAMA or LABA active agents will have a therapeutic effect. In one embodiment, the patient is a human being.

"Perforated microstructures" refer to suspending particles that include a structural matrix that exhibits, defines or comprises voids, pores, defects, hollows, spaces, interstitial spaces, apertures, perforations or holes that allow the surrounding suspension medium to permeate, fill or pervade the microstructure, such as those materials and preparations described in U.S. Pat. No. 6,309,623 to Weers, et al. The primary form of the perforated microstructure is, generally, not essential, and any overall configuration that provides the desired formulation characteristics is contemplated herein. Accordingly, in one embodiment, the perforated microstructures may comprise approximately spherical shapes, such as hollow, suspending, spray-dried microspheres. However, collapsed, corrugated, deformed or fractured particulates of any primary form or aspect ratio may also be compatible.

As is true of suspending particles described herein, perforated microstructures may be formed of any biocompatible material that does not substantially degrade or dissolve in the selected suspension medium. While a wide variety of materials may be used to form the particles, in some embodiments, the structural matrix is associated with, or includes, a surfactant such as, a phospholipid or fluorinated surfactant. Although not required, the incorporation of a compatible surfactant in the perforated microstructure or, more generally, the suspending particles, can improve the stability of the respiratory dispersions, increase pulmonary deposition and facilitate the preparation of the suspension.

The term "suspension medium" as uses herein refers to a substance providing a continuous phase within which active agent particles and suspending particles can be dispersed to provide a co-suspension formulation. The suspension medium used in co-suspension formulations described herein includes propellant. As used herein, the term "propellant" refers to one or more pharmacologically inert substances which exert a sufficiently high vapor pressure at normal room temperature to propel a medicament from the canister of an MDI to a patient on actuation of the MDI's metering valve. Therefore, the term "propellant" refers to both a single propellant and to a combination of two or more different propellants forming a "propellant system."

The term "respirable" generally refers to particles, aggregates, drops, etc. sized such that they can be inhaled and reach the airways of the lung.

When used to refer to co-suspension compositions described herein, the terms "physical stability" and "physically stable" refer to a composition that is resistant to one or more of aggregation, flocculation, and particle size changes due to solution mediated transformations and is capable of substantially maintaining the MMAD of suspending particles and the fine particle dose. In one embodiment, physical stability may be evaluated through subjecting compositions to accelerated degradation conditions, such as by temperature cycling as described herein.

When referring to active agents, the term "potent" indicates active agents that are therapeutically effective at or below doses ranging from about 0.01 mg/kg to about 1 mg/kg. Typical doses of potent active agents generally range from about 100 µg to about 100 mg.

When referring to active agents, the term "highly potent" indicates active agents that are therapeutically effective at or below doses of about 10 µg/kg. Typical doses of highly potent active agents generally range up to about 100 µg.

The terms "suspension stability" and "stable suspension" refer to suspension formulations capable of maintaining the properties of a co-suspension of active agent particles and suspending particles over a period of time. In one embodiment, suspension stability may be measured through delivered dose uniformity achieved by co-suspension compositions described herein.

The term "substantially insoluble" means that a composition is either totally insoluble in a particular solvent or it is poorly soluble in that particular solvent. The term "substantially insoluble" means that a particular solute has a solubility of less than one part per 100 parts solvent. The term "substantially insoluble" includes the definitions of "slightly soluble" (from 100 to 1000 parts solvent per 1 part solute), "very slightly soluble" (from 1000 to 10,000 parts solvent per 1 part solute) and "practically insoluble" (more than 10,000 parts solvent per 1 part solute) as given in Table 16-1 of Remington: The Science and Practice of Pharmacy, 21st ed. Lippincott, Williams & Wilkins, 2006, p. 212.

The term "surfactant," as used herein, refers to any agent which preferentially adsorbs to an interface between two immiscible phases, such as the interface between water and an organic polymer solution, a water/air interface or organic solvent/air interface. Surfactants generally possess a hydrophilic moiety and a lipophilic moiety, such that, upon adsorbing to microparticles, they tend to present moieties to the continuous phase that do not attract similarly-coated particles, thus reducing particle agglomeration. In some embodiments, surfactants may also promote adsorption of a drug and increase bioavailability of the drug.

A "therapeutically effective amount" is the amount of compound which achieves a therapeutic effect by inhibiting a disease or disorder in a patient or by prophylactically inhibiting or preventing the onset of a disease or disorder. A therapeutically effective amount may be an amount which relieves to some extent one or more symptoms of a disease or disorder in a patient; returns to normal either partially or completely one or more physiological or biochemical parameters associated with or causative of the disease or disorder; and/or reduces the likelihood of the onset of the disease of disorder.

The terms "chemically stable" and "chemical stability" refer to co-suspension formulations wherein the individual degradation products of active agent remain below the limits specified by regulatory requirements during the shelf life of the product for human use (e.g., 1% of total chromatographic peak area per ICH guidance Q3B(R2)) and there is acceptable mass balance (e.g., as defined in ICH guidance Q1E) between active agent assay and total degradation products.

II. Pharmaceutical Compositions

The compositions described herein are co-suspensions that include a suspension medium including a propellant, LAMA or LABA active agent particles, and suspending particles. Of course, if desired, the compositions described herein may include one or more additional constituents. Moreover, variations and combinations of components of the compositions described herein may be used. For example, two or more species of suspending particles may be used in compositions for the formulation and delivery of a selected LAMA or LABA active agent. Alternatively, for example, the compositions described herein may include two or more species of active agent particles. In certain such embodiments, the compositions may include LAMA or LABA active agent particles co-suspended with suspending particles, wherein, in addition to the active agent material included in the active agent particles, at least some of the suspending particles incorporate the selected LAMA or LABA active agent. Even further, if desired, the compositions described herein may include two or more different species of particles containing the selected LAMA or LABA active agent in combination with two or more different species of suspending particles.

It has been found that, in formulations according to the present description, active agent particles exhibit an association with the suspending particles such that separation of the active agent particles from the suspending particles is substantially prevented, resulting in co-location of active agent particles and suspending particles within the suspension medium. Generally, due to density differences between distinct species of particles and the medium within which they are suspended (e.g., a propellant or propellant system), buoyancy forces cause creaming of particles with lower density than the propellant and sedimentation of particles with higher density than the propellant. Therefore, in suspensions that include a mixture of particles that vary in their densities, the sedimentation or creaming behavior of each type of particle may vary and may lead to separation of the different particle types within the propellant.

However, the combinations of propellant, active agent particles and suspending particles described herein provide co-suspensions wherein the active agent particles and suspending particles co-locate within the propellant (i.e., the active agent particles associate with the suspending particles such that suspending particles and active agent particles do not exhibit substantial separation relative to each other, such as by differential sedimentation or creaming, even after a time sufficient for the formation of a cream or sediment layer). In particular embodiments, for example, the compositions described herein form co-suspensions wherein the suspending particles remain associated with active agent particles when subjected to buoyancy forces amplified by temperature fluctuations and/or centrifugation at accelerations up to an over, for example, 1 g, 10 g, 35 g, 50 g, and 100 g. However, the co-suspensions described herein need not be defined by or limited to a specific threshold force of association. For example, a co-suspension as contemplated herein may be successfully achieved where the active agent particles associate with the suspending particles such that there is no substantial separation of active agent particles and suspending particles within the continuous phase formed by the suspension medium under typical patient use conditions.

Co-suspension compositions according to the present description provide desirable formulation and delivery characteristics for LAMA and LABA active agents. For example, in certain embodiments, when present within an MDI canister, co-suspensions as described herein can inhibit or reduce one or more of the following: flocculation of active agent material; differential sedimentation or creaming of active agent particles and suspending particles; solution mediated transformation of active agent material; and loss of active agent to the surfaces of the container closure system, in particular the metering valve components. In addition, compositions as described herein provide chemical stability for the active agents contained therein. Such qualities work to achieve and preserve aerosol performance as the co-suspension is delivered from an MDI such that desirable fine particle fraction, fine particle dose and delivered dose uniformity characteristics are achieved and substantially maintained throughout emptying of an MDI canister within which the co-suspension composition is contained. Additionally, as illustrated by embodiments detailed herein, co-suspensions according to the present description can provide a stable formulation that provides consistent dosing and respiratory delivery characteristics for LAMA and LABA active agents, while utilizing a relatively simple HFA suspension medium that does not require modification by the addition of, for example, cosolvents, antisolvents, solubilizing agents or adjuvants.

Providing a co-suspension according to the present description may also simplify formulation, delivery and dosing of LAMA and LABA active agents. Without being bound by a particular theory, it is thought that by achieving a co-suspension of active agent particles and suspending particles, the delivery and dosing of active agent contained within such a dispersion may be substantially controlled through control of the size, composition, morphology and relative amount of the suspending particles, and less dependent upon the size and morphology of the active agent particles.

Accordingly, the pharmaceutical compositions disclosed herein provide for delivery of LAMA and LABA active agents from an MDI. Delivery of the co-suspension compositions described herein provides desirable pharmacokinetic and pharmacodynamic characteristics, and MDI delivery of the pharmaceutical compositions described herein is suitable for treating patients suffering from an inflammatory or obstructive pulmonary disease or condition that responds to the administration of a LAMA or LABA active agent. In particular embodiments, the pharmaceutical compositions described herein may be used in treating a disease or condition selected from asthma, COPD, exacerbation of airways hyper reactivity consequent to other drug therapy, allergic rhinitis, sinusitis, pulmonary vasoconstriction, inflammation, allergies, impeded respiration, respiratory distress syndrome, pulmonary hypertension, pulmonary vasoconstriction, emphysema, and any other respiratory disease, condition, trait, genotype or phenotype that can respond to the administration of a LAMA or LABA, alone or in combination with other therapies. In certain embodiments, the compositions, systems and methods described herein can be used to treat pulmonary inflammation and obstruction associated with cystic fibrosis.

(i) Suspension Medium

The suspension medium included in a composition described herein includes one or more propellants. In general, suitable propellants for use as suspension mediums are those propellant gases that can be liquefied under pressure at room temperature, and upon inhalation or topical use, are safe and toxicologically innocuous. Additionally, it is desirable that the selected propellant be relatively non-reactive with the suspending particles or active agent particles. Exemplary compatible propellants include hydrofluoroalkanes (HFAs), perfluorinated compounds (PFCs), and chlorofluorocarbons (CFCs).

Specific examples of propellants that may be used to form the suspension medium of the co-suspensions disclosed herein include 1,1,1,2-tetrafluoroethane ($CF_3CH_2F$) (HFA-134a), 1,1,1,2,3,3,3-heptafluoro-n-propane ($CF_3CHFCF_3$) (HFA-227), perfluoroethane, monochloro-fluoromethane, 1,1 difluoroethane, and combinations thereof. Even further, suitable propellants include, for example: short chain hydrocarbons; $C_{1-4}$ hydrogen-containing chlorofluorocarbons such as $CH_2ClF$, $CCl_2FCHClF$, $CF_3CHClF$, $CHF_2CClF_2$, $CHClFCHF_2$, $CF_3CH_2Cl$, and $CClF_2CH_3$; $C_{1-4}$ hydrogen-containing fluorocarbons (e.g., HFAs) such as $CHF_2CHF_2$, $CF_3CH_2F$, $CHF_2CH_3$, and $CF_3CHFCF_3$; and perfluorocarbons such as $CF_3CF_3$ and $CF_3CF_2CF_3$.

Specific fluorocarbons, or classes of fluorinated compounds, that may be used as suspension media include, but are not limited to, fluoroheptane, fluorocycloheptane, fluoromethylcycloheptane, fluorohexane, fluorocyclohexane, fluoropentane, fluorocyclopentane, fluoromethylcyclopentane, fluorodimethyl-cyclopentanes, fluoromethylcyclobutane, fluorodimethylcyclobutane, fluorotrimethyl-cyclobutane, fluorobutane, fluorocyclobutane, fluoropropane, fluoroethers, fluoropolyethers and fluorotriethylamines. These compounds may be used alone or in combination with more volatile propellants.

In addition to the aforementioned fluorocarbons and hydrofluoroalkanes, various exemplary chlorofluorocarbons and substituted fluorinated compounds may also be used as suspension media. In this respect, FC-11 ($CCl_3F$), FC-11B1 ($CBrCl_2F$), FC-11B2 ($CBr_2ClF$), FC12B2 ($CF_2Br_2$), FC21 ($CHCl_2F$), FC21B1 ($CHBrClF$), FC-21B2 ($CHBr_2F$), FC-31B1 ($CH_2BrF$), FC113A ($CCl_3CF_3$), FC-122 ($CClF_2CHCl_2$), FC-123 ($CF_3CHCl_2$), FC-132 ($CHClFCHClF$), FC-133 ($CHClFCHF_2$), FC-141 ($CH_2ClCHClF$), FC-141B($CCl_2FCH_3$), FC-142 ($CHF_2CH_2Cl$), FC-151 ($CH_2FCH_2Cl$), FC-152 ($CH_2FCH_2F$), FC-1112 ($CClF{=}CClF$), FC-1121 ($CHCl{=}CFCl$) and FC-1131 ($CHCl{=}CHF$) may also be used, while recognizing the possible attendant environmental concerns. As such, each of these compounds may be used, alone or in combination with other compounds (i.e., less volatile fluorocarbons) to form the stabilized suspensions disclosed herein.

In some embodiments, the suspension medium may be formed of a single propellant. In other embodiments, a combination of propellants (a "propellant system") may be used to form the suspension medium. In some embodiments, relatively volatile compounds may be mixed with lower vapor pressure components to provide suspension media having specified physical characteristics selected to improve stability or enhance the bioavailability of the dispersed active agent. In some embodiments, the lower vapor pressure compounds will comprise fluorinated compounds (e.g. fluorocarbons) having a boiling point greater than about 25° C. In some embodiments, lower vapor pressure fluorinated compounds for use in the suspension medium may include perfluorooctylbromide $C_8F_{17}Br$ (PFOB or perflubron), dichlorofluorooctane $C_8F_{16}Cl_2$, perfluorooctylethane $C_8F_{17}C_2H_5$ (PFOE), perfluorodecylbromide $C_{10}F_{21}Br$ (PFDB) or perfluorobutylethane $C_4F_9C_2H_5$. In certain embodiments, these lower vapor pressure compounds are present in a relatively low level. Such compounds may be added directly to the suspension medium or may be associated with the suspending particles.

The suspension medium included in compositions as described herein may be formed of a propellant or propellant system that is substantially free of additional materials, including, for example, antisolvents, solubilizing agents, cosolvents or adjuvants. For example, in some embodiments, the suspension medium may be formed of a non-CFC propellant or propellant system, such as an HFA propellant or propellant system, that is substantially free of additional materials. Such embodiments simplify the formulation and manufacture of pharmaceutical compositions suited for respiratory delivery of a LAMA or LABA active agent.

However, in other embodiments, depending on the selection of propellant, the properties of the suspending particles, or the nature of active agent to be delivered, the suspension medium utilized may include materials in addition to the propellant or propellant system. Such additional materials may include, for example, one or more of an appropriate antisolvent, solubilizing agent, cosolvent or adjuvant to adjust, for example, the vapor pressure of the formulation or the stability, or solubility of suspended particles. For example, propane, ethanol, isopropyl alcohol, butane, isobutane, pentane, isopentane or a dialkyl ether, such as dimethyl ether, may be incorporated with the propellant in the suspension medium. Similarly, the suspension medium may contain a volatile fluorocarbon. In other embodiments, one or both of polyvinylpyrrolidone ("PVP") or polyethylene glycol ("PEG") may be added to the suspension medium. Adding PVP or PEG to the suspension medium may achieve one or more desired functional characteristics, and in one example, PVP or PEG may be added to the suspension medium as a crystal growth inhibitor. In general, where a volatile cosolvent or adjuvant is used, such an adjuvant or cosolvent may be selected from known hydrocarbon or fluorocarbon materials and may account for up to about 1% w/w of the suspension medium. For example, where a cosolvent or adjuvant is incorporated in the suspension medium, the cosolvent or adjuvant may comprise less than about 0.01%, 0.1%, or 0.5% w/w of the suspension medium. Where PVP or PEG are included in the suspension medium, such constituents may be included at up to about 1% w/w, or they may comprise less than about 0.01%, 0.1%, or 0.5% w/w of the suspension medium.

(ii) Active Agent Particles

The active agent particles included in the co-suspensions described herein are formed to be capable of being dispersed and suspended within the suspension medium and are sized to facilitate delivery of respirable particles from the co-suspension. In one embodiment, therefore, the active agent particles are provided as a micronized material wherein at least 90% of the active agent particle material by volume exhibits an optical diameter of about 7 μm or less. In other embodiments, the active agent particles are provided as a micronized material wherein at least 90% of the active agent particles by volume exhibit an optical diameter selected from a range of about 6 μm to about 1 μm, about 5 μm to about 2 μm, and about 4 μm to about 3 μm. In further embodiments, the active agent particles are provided as a micronized material wherein at least 90% of the active agent particles by volume exhibit an optical diameter selected from 6 μm or less, 5 μm or less, and 4 μm or less. In another embodiment, the active agent particles are provided as a micronized material wherein at least 50% of the active agent particle material by volume exhibits an optical diameter of about 5 μm or less. In other embodiments, the active agent particles are provided as a micronized material wherein at least 50% of the active agent particles by volume exhibit an optical diameter selected from a range of about 4 μm to about 1 μm, about 3 μm to about 1 μm, and about 2.5 μm to about 1 μm. In another embodiment, the active agent particles are provided as a micronized material wherein at least 50% of the active agent particles by volume exhibit an optical diameter selected from 4 μm or less, 3 μm or less, and 2 μm or less.

In specific embodiments, the active agent material used as or to form the active agent particles may be entirely or substantially crystalline, i.e., a majority of the active agent molecules are arranged in a regularly repeating pattern, over a long range or external face planes. In another embodiment, the active agent particles may be present in both crystal and amorphous states. In yet another embodiment, the active agent particles may be present in substantially an amorphous state, i.e., the active agent particles are overall noncrystalline in nature and do not have a regularly repeating arrangement of molecules maintained over along range. Suitable excipients for formulation of active agent particles include those described herein in association with the suspending particles. In specific embodiments, for example, active agent particles may be formulated with one or more of the lipid, phospholipid, carbohydrate, amino acid, organic salt, peptide, protein, alditols, synthetic or natural polymer, or surfactant materials as described, for example, in association with the suspending particles. In other embodiments, the active agent particles are formed solely from micronized active agent material.

Because the compositions disclosed enable the formulation and reproducible delivery of very low doses of active agents, in certain embodiments, the active agents included in the compositions described herein may be selected from one or more potent or highly potent active agents. For example, in certain embodiments, the compositions described herein may include a potent active agent that is delivered at a single administration dose selected from between about 100 μg and about 100 mg per dose, about 100 μg and about 10 mg per dose, and about 100 μg and 1 mg per dose. In other embodiments, the compositions described herein may include a potent or highly potent active agent that is delivered at a dose selected from up to about 80 μg per single administration dose, up to about 40 μg per single administration dose, up to about 20 μg per single administration dose, up to about 10 μg per single administration dose or between about 10 μg and about 100 μg per single administration dose. Additionally, in certain embodiments, the compositions described herein may include a highly potent active agent delivered at a dose selected from between about 0.1 and about 2 μg per single administration dose, about 0.1 and about 1 μg per single administration dose, and about 0.1 and about 0.5 μg per single administration dose.

In certain embodiments, the active agent included in the compositions described herein is a LAMA active agent. Where the compositions include a LAMA active agent, in particular embodiments, the LAMA active agent may be selected from, for example, glycopyrrolate, dexipirronium, tiotropium, trospium, aclidinium, darotropium, including any pharmaceutically acceptable salts, esters, isomers or solvates thereof.

Glycopyrrolate can be used to treat inflammatory or obstructive pulmonary diseases and disorders such as, for example, those described herein. As an anticholinergic, glycopyrrolate acts as a bronchodilator and provides an antisecretory effect, which is a benefit for use in the therapy of pulmonary diseases and disorders characterized by increased mucus secretions. Glycopyrrolate is a quaternary ammonium salt. Where appropriate, glycopyrrolate may be used in the form of salts (e.g. alkali metal or amine salts, or as acid addition salts) or as esters or as solvates (hydrates). Additionally, the glycopyrrolate may be in any crystalline form or isomeric form or mixture of isomeric forms, for example a pure enantiomer, a mixture of enantiomers, a racemate or a mixture thereof. In this regard, the form of glycopyrrolate may be selected to optimize the activity and/or stability of glycopyrrolate and/or to minimize the solubility of glycopyrrolate in the suspension medium. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate. In particular embodiments of the compositions described herein, the bromide salt of glycopyrrolate, namely 3-[(cyclopentyl-hydroxyphenylacetyl)oxy]-1,1-dimethylpyrrolidinium bromide, is used and can be prepared according to the procedures set out in U.S. Pat. No. 2,956,062.

Where the compositions described herein include glycopyrrolate, in certain embodiments, the compositions may include sufficient glycopyrrolate to provide a target delivered dose selected from between about 10 μg and about 200 μg per actuation of an MDI, about 15 μg and about 150 μg per actuation of an MDI, and about 18 μg and 144 μg per actuation of an MDI. In other such embodiments, the formulations include sufficient glycopyrrolate to provide a dose selected from up to about 200 μg, up to about 150 μg, up to about 75 μg, up to about 40 μg, or up to about 20 μg per actuation. In yet further embodiments, the formulations include sufficient glycopyrrolate to provide a dose selected from about 18 μg per actuation, 36 μg per actuation, or about 72 μg per actuation. In order to achieve targeted delivered doses as described herein, where compositions described herein include glycopyrrolate as the active agent, in specific embodiments, the amount of glycopyrrolate included in the compositions may be selected from, for example, between about 0.04 mg/ml and about 2.25 mg/ml.

In other embodiments, tiotropium, including any pharmaceutically acceptable salts, esters, isomers or solvates thereof, may be selected as a LAMA active agent for inclusion in a composition as described herein. Tiotropium is a known, long-acting anticholinergic drug suitable for use in treating diseases or disorders associated with pulmonary inflammation or obstruction, such as those described herein. Tiotropium, including crystal and pharmaceutically acceptable salt forms of tiotropium, is described, for example, in U.S. Pat. Nos. 5,610,163, RE39820, 6,777,423, and 6,908,928. Where the compositions described herein include tiotropium, in certain embodiments, the compositions may include sufficient tiotropium to provide a delivered dose selected from between about 2.5 μg and about 50 μg, about 4 μg and about 25 μg, about 2.5 μg and about 20 μg, about 10 μg and about 20 μg, and about 2.5 μg and about 10 μg per actuation of an MDI. In other such embodiments, the formulations include sufficient tiotropium to provide a delivered dose selected from up to about 50 μg, up to about 20 μg, up to about 10 μg, up to about 5 μg, or up to about 2.5 μg per actuation of an MDI. In yet further embodiments, the formulations include sufficient tiotropium to provide a delivered dose selected from about 3 μg, 6 μg, 9 μg, 18 μg, and 36 μg per actuation of the MDI. In order to achieve delivered doses as described herein, where compositions described herein include tiotropium as the active agent, in specific embodiments, the amount of tiotropium included in the compositions may be selected from, for example, between about 0.01 mg/ml and about 0.5 mg/ml.

In certain embodiments, the compositions described herein include a LABA active agent. In such embodiments, a LABA active agent can be selected from, for example, bambuterol, clenbuterol, formoterol, salmeterol, carmoterol, milveterol, indacaterol, and saligenin- or indole-containing and adamantyl-derived $\beta_2$ agonists, and any pharmaceutically acceptable salts, esters, isomers or solvates thereof. In certain such embodiments, formoterol is selected as the LABA active agent. Formoterol can be used to treat inflammatory or obstructive pulmonary diseases and disorders such as, for example, those described herein. Formoterol has the chemical name (±)-2-hydroxy-5-[(1RS)-1-hydroxy-2-[[(1RS)-2-(4-methoxyphenyl)-1-methylethyl]-amino]ethyl] formanilide, and is commonly used in pharmaceutical compositions as the racemic fumarate dihydrate salt. Where appropriate, formoterol may be used in the form of salts (e.g. alkali metal or amine salts or as acid addition salts) or as esters or as solvates (hydrates). Additionally, the formoterol may be in any crystalline form or isomeric form or mixture of isomeric forms, for example a pure enantiomer, a mixture of enantiomers, a racemate or a mixture thereof. In this regard, the form of formoterol may be selected to optimize the activity and/or stability of formoterol and/or to minimize the solubility of formoterol in the suspension medium. Pharmaceutically acceptable salts of formoterol include, for example, salts of inorganic acids such as hydrochloric, hydrobromic, sulfuric and phosphoric acids, and organic acids such as fumaric, maleic, acetic, lactic, citric, tartaric, ascorbic, succinic, glutaric, gluconic, tricarballylic, oleic, benzoic, p-methoxybenzoic, salicylic, o- and p-hydroxybenzoic, p-chlorobenzoic, methanesulfonic, p-toluenesulfonic and 3-hydroxy-2-naphthalene carboxylic acids. Hydrates of formoterol are described, for example, in U.S. Pat. Nos. 3,994,974 and 5,684,199. Specific crystalline forms of formoterol and other $\beta_2$ adrenergic receptor agonists are described, for example, in WO95/05805, and specific isomers of formoterol are described in U.S. Pat. No. 6,040,344.

In specific embodiments, the formoterol material utilized to form the formoterol particles is formoterol fumarate, and in one such embodiment, the formoterol fumarate is present in the dihydrate form. Where the compositions described herein include formoterol, in certain embodiments, the compositions described herein may include formoterol at a concentration that achieves a targeted delivered dose selected from between about 1 μg and about 30 μg, about 1 μg and about 10 μg, about 2 μg and 5 μg, about 2 μg and about 10 μg, about 5 μg and about 10 μg, and 3 μg and about 30 μg per actuation of an MDI. In other embodiments, the compositions described herein may include formoterol in an amount sufficient to provide a targeted delivered dose selected from up to about 30 μg, up to about 10 μg, up to about 5 μg, up to about 2.5 μg, up to about 2 μg, or up to about 1.5 μg per actuation. In order to achieve targeted delivered doses as described herein, where compositions described herein include formoterol as the active agent, in specific embodiments, the amount of formoterol included in the compositions may be selected from, for example, between about 0.01 mg/ml and about 1 mg/ml, between about 0.01 mg/ml and about 0.5 mg/ml, and between about 0.03 mg/ml and about 0.4 mg/ml.

Where the pharmaceutical co-suspension compositions described herein include a LABA active agent, in certain embodiments, the active agent may be salmeterol, including any pharmaceutically acceptable salts, esters, isomers or solvates thereof. Salmeterol can be used to treat inflammatory or obstructive pulmonary diseases and disorders such as, for example, those described herein. Salmeterol, pharmaceutically acceptable salts of salmeterol, and methods for producing the same are described, for example, in U.S. Pat. Nos. 4,992,474, 5,126,375, and 5,225,445.

Where salmeterol is included as a LABA active agent, in certain embodiments, the compositions described herein may include salmeterol at a concentration that achieves a delivered dose selected from between about 2 µg and about 120 µg, about 4 µg and about 40 µg, about 8 µg and 20 µg, about 8 µg and about 40 µg, about 20 µg and about 40 µg, and 12 µg and about 120 µg per actuation of an MDI. In other embodiments, the compositions described herein may include salmeterol in an amount sufficient to provide a delivered dose selected from up to about 120 µg, up to about 40 µg, up to about 20 µg, up to about 10 µg, up to about 8 µg, or up to about 6 µg per actuation of an MDI. In order to achieve targeted delivered doses as described herein, where compositions described herein include salmeterol as the active agent, in specific embodiments, the amount of salmeterol included in the compositions may be selected from, for example, between about 0.04 mg/ml and about 4 mg/ml, between about 0.04 mg/ml and about 2.0 mg/ml, and between about 0.12 mg/ml and about 0.8 mg/ml. For example, the compositions described herein may include sufficient salmeterol to provide a target delivered dose selected from between about 4 µg and about 120 µg, about 20 µg and about 100 µg, and between about 40 µg and about 120 µg per actuation of an MDI. In still other embodiments, the compositions described herein may include sufficient salmeterol to provide a targeted delivered dose selected from up to about 100 µg, up to about 40 µg, or up to about 15 µg per actuation of an MDI.

Though the active agent material included in the compositions described herein may be amorphous or substantially amorphous, in specific embodiments, the active agent material used as or in the formation of the active agent particles included in the compositions described herein is substantially or entirely crystalline. Active agent material that is substantially or entirely crystalline may be selected to improve the chemical stability of the LAMA or LABA active agent when formulated in the compositions described herein. Therefore, in specific embodiments, the active agent material included in the compositions described herein is a micronized, crystalline LAMA material. In one such embodiment, the active agent particles are formed solely of micronized, crystalline LAMA material, such as a micronized crystalline material selected from glycopyrrolate, dexipirronium, tiotropium, trospium, aclidinium, darotropium, and any pharmaceutically acceptable salts, esters or solvates thereof. In other specific embodiments, the active agent material included in the compositions described herein is a micronized, crystalline LABA material. In one such embodiment, the active agent particles are formed solely of micronized, crystalline LABA material, such as a micronized crystalline material selected from bambuterol, clenbuterol, formoterol, salmeterol, carmoterol, milveterol, indacaterol, and saligenin- or indole-containing and adamantyl-derived $\beta_2$ agonists, and any pharmaceutically acceptable salts, esters or solvates thereof.

Any suitable process may be employed to achieve micronized active agent material as or in the formulation of the active agent particles included in the compositions described herein. A variety of processes may be used to create active agent particles suitable for use in the co-suspension formulations described herein, including, but not limited to micronization by milling or grinding processes, crystallization or recrystallization processes, and processes using precipitation from supercritical or near-supercritical solvents, spray drying, spray freeze drying, or lyophilization. Patent references teaching suitable methods for obtaining micronized active agent particles are described, for example, in U.S. Pat. Nos. 6,063,138, 5,858,410, 5,851,453, 5,833,891, 5,707,634, and International Patent Publication No. WO 2007/009164. Where the active agent particles include active agent material formulated with one or more excipient or adjuvant, micronized active agent particles can be formed using one or more of the preceding processes and such processes can be utilized to achieve active agent particles having a desired size distribution and particle configuration.

(iii) Suspending Particles

The suspending particles included in the co-suspension compositions described herein work to facilitate stabilization and delivery of the active agent included in the compositions. Though various forms of suspending particles may be used, the suspending particles are typically formed from pharmacologically inert material that is acceptable for inhalation and is substantially insoluble in the propellant selected. Generally, the majority of suspending particles are sized within a respirable range. In particular embodiments, therefore, the MMAD of the suspending particles will not exceed about 10 µm but is not lower than about 500 nm. In an alternative embodiment, the MMAD of the suspending particles is between about 5 µm and about 750 nm. In yet another embodiment, the MMAD of the suspending particles is between about 1 µm and about 3 µm. When used in an embodiment for nasal delivery from an MDI, the MMAD of the suspending particles is between 10 µm and 50 µm.

In order to achieve respirable suspending particles within the MMAD ranges described, the suspending particles will typically exhibit a volume median optical diameter between about 0.2 µm and about 50 µm. In one embodiment, the suspending particles exhibit a volume median optical diameter that does not exceed about 25 µm. In another embodiment, the suspending particles exhibit a volume median optical diameter selected from between about 0.5 µm and about 15 µm, between about 1.5 µm and about 10 µm, and between about 2 µm and about 5 µm.

The concentration of suspending particles included in a composition according to the present description can be adjusted, depending on, for example, the amount of active agent particles and suspension medium used. In one embodiment, the suspending particles are included in the suspension medium at a concentration selected from about 1 mg/ml to about 15 mg/ml, about 3 mg/ml to about 10 mg/ml, 5 mg/ml to about 8 mg/ml, and about 6 mg/ml. In another embodiment, the suspending particles are included in the suspension medium at a concentration of up to about 30 mg/ml. In yet another embodiment, the suspending particles are included in the suspension medium at a concentration of up to about 25 mg/ml.

The relative amount of suspending particles to active agent particles is selected to achieve a co-suspension as contemplated herein. A co-suspension composition may be achieved where the amount of suspending particles, as measured by mass, exceeds that of the active agent particles. For example, in specific embodiments, the ratio of the total mass of the suspending particles to the total mass of active agent particles may be between about 3:1 and about 15:1, or alternatively from about 2:1 and 8:1. Alternatively, the ratio of the total mass of the suspending particles to the total mass of active agent particles may be above about 1, such as up to about 1.5, up to about 5, up to about 10, up to about 15, up to about 17, up to about 20, up to about 30, up to about 40, up to about 50, up to about 60, up to about 75, up to about 100, up to about 150, and up to about 200, depending on the nature of the suspending particles and active agent particles used. In further embodiments, the ratio of the total mass of the suspending particles to the total mass of the active agent particles may be selected from between about 10 and about 200, between about 60 and about 200, between about 15 and about 60, between about 15 and about 170, between about 15 and about 60, about 16, about 60, and about 170.

In other embodiments, the amount of suspending particles, as measured by mass, is less than that of the active agent particles. For example, in particular embodiments, the mass of the suspending particles may be as low as 20% of the total mass of the active agent particles. However, in some embodiments, the total mass of the suspending particles may also approximate or equal the total mass of the active agent particles.

Suspending particles suitable for use in the compositions described herein may be formed of one or more pharmaceutically acceptable materials or excipients that are suitable for inhaled delivery and do not substantially degrade or dissolve in the suspension medium. In one embodiment, perforated microstructures, as defined herein, may be used as the suspending particles. Exemplary excipients that may be used in the formulation of suspending particles described herein include but are not limited to (a) carbohydrates, e.g., monosaccharides such as fructose, galactose, glucose, D-mannose, sorbose, and the like; disaccharides, such as sucrose, lactose, trehalose, cellobiose, and the like; cyclodextrins, such as 2-hydroxypropyl-β-cyclodextrin; and polysaccharides, such as raffinose, maltodextrins, dextrans, starches, chitin, chitosan, inulin, and the like; (b) amino acids, such as alanine, glycine, arginine, aspartic acid, glutamic acid, cysteine, lysine, leucine, isoleucine, valine, and the like; (c) metal and organic salts prepared from organic acids and bases, such as sodium citrate, sodium ascorbate, magnesium gluconate, sodium gluconate, tromethamin hydrochloride, and the like; (d) peptides and proteins such as aspartame, trileucine, human serum albumin, collagen, gelatin, and the like; (e) alditols, such as mannitol, xylitol, and the like; (f) synthetic or natural polymers or combinations thereof, such as polylactides, polylactide-glycolides, cyclodextrins, polyacrylates, methylcellulose, carboxymethylcellulose, polyvinyl alcohols, polyanhydrides, polylactams, polyvinyl pyrrolidones, hyaluronic acid, polyethylene glycols; and (g) surfactants including fluorinated and nonfluorinated compounds such as saturated and unsaturated lipids, nonionic detergents, nonionic block copolymers, ionic surfactants and combinations thereof. In particular embodiments, suspending particles may include a calcium salt, such as calcium chloride, as described, for example, in U.S. Pat. No. 7,442,388.

Additionally, phospholipids from both natural and synthetic sources may be used in preparing suspending particles suitable for use in the compositions described herein. In particular embodiments, the phospholipid chosen will have a gel to liquid crystal phase transition of greater than about 40° C. Exemplary phospholipids are relatively long chain (i.e., $C_{16}$-$C_{22}$) saturated lipids and may comprise saturated phospholipids, such as saturated phosphatidylcholines having acyl chain lengths of 16 C or 18 C (palmitoyl and stearoyl). Exemplary phospholipids include phosphoglycerides such as dipalmitoylphosphatidylcholine, disteroylphosphatidylcholine, diarachidoylphosphatidylcholine, dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, and long-chain saturated phosphatidylinositols. Additional excipients are disclosed in International Patent Publication No. WO 96/32149 and U.S. Pat. Nos. 6,358,530, 6,372,258 and 6,518,239.

In particular embodiments, the suspending particles may be formed using one or more lipids, phospholipids or saccharides, as described herein. In some embodiments, suspending particles include one or more surfactants. The use of suspending particles formed of or incorporating one or more surfactants may promote absorption of the selected active agent, thereby increasing bioavailability. The suspending particles described herein, such as, for example, suspending particles formed using one or more lipids, can be formed to exhibit a desired surface rugosity (roughness), which can further reduce inter-particle interactions and improve aerosolization by reducing the surface area available for particle-particle interaction. In further embodiments, if suitable, a lipid that is naturally occurring in the lung could be used in forming the suspending particles, as such suspending particles that have the potential to reduce opsonization (and thereby reducing phagocytosis by alveolar macrophages), thus providing a longer-lived controlled release particle in the lung.

In another aspect, the suspending particles utilized in the compositions described herein may be selected to increase storage stability of the selected active agent, similar to that disclosed in International Patent Publication No WO 2005/000267. For example, in one embodiment, the suspending particles my include pharmaceutically acceptable glass stabilization excipients having a Tg of at least 55° C., at least 75° C., or at least 100° C. Glass formers suitable for use in compositions described herein include, but are not limited to, one or more of trileucine, sodium citrate, sodium phosphate, ascorbic acid, inulin, cyclodextrin, polyvinyl pyrrolidone, mannitol, sucrose, trehalose, lactose, and, proline. Examples of additional glass-forming excipients are disclosed in U.S. Pat. Nos. RE 37,872, 5,928,469, 6,258,341.

The suspending particles may be designed, sized and shaped as desired to provide desirable stability and active agent delivery characteristics. In one exemplary embodiment, the suspending particles comprise perforated microstructures as described herein. Where perforated microstructures are used as suspending particles in the compositions described herein, they may be formed using one or more excipients as described herein. For example, in particular embodiments, perforated microstructures may include at least one of the following: lipids, phospholipids, nonionic detergents, nonionic block copolymers, ionic surfactants, biocompatible fluorinated surfactants and combinations thereof, particularly those approved for pulmonary use. Specific surfactants that may be used in the preparation of perforated microstructures include poloxamer 188, poloxamer 407 and poloxamer 338. Other specific surfactants include oleic acid or its alkali salts. In one embodiment, the perforated microstructures include greater than about 10% w/w surfactant.

In some embodiments, suspending particles may be prepared by forming an oil-in-water emulsion, using a fluorocarbon oil (e.g., perfluorooctyl bromide, perfluorodecalin) which may be emulsified using a surfactant such as a long chain saturated phospholipid. The resulting perfluorocarbon in water emulsion may be then processed using a high pressure homogenizer to reduce the oil droplet size. The perfluorocarbon emulsion may be fed into a spray dryer, optionally with an active agent solution, if it is desirable to include active agent within the matrix of the perforated microstructures. As is well known, spray drying is a one-step process that converts a liquid feed to a dried particulate form. Spray drying has been used to provide powdered pharmaceutical material for various administrative routes, including inhalation. Operating conditions of the spray dryer (such as inlet and outlet temperature, feed rate, atomization pressure, flow rate of the drying air and nozzle configuration) can be adjusted to produce the desired particle size producing a yield of the resulting dry microstructures. Such methods of producing exemplary perforated microstructures are disclosed in U.S. Pat. No. 6,309,623 to Weers et al.

Perforated microstructures as described herein may also be formed through lyophilization and subsequent milling or micronization. Lyophilization is a freeze-drying process in which water is sublimed from the composition after it is frozen. This process allows drying without elevated temperatures. In yet further embodiments, the suspending particles may be produced using a spray freeze drying process, such as is disclosed in U.S. Pat. No. 5,727,333.

Furthermore, suspending particles as described herein may include bulking agents, such as polymeric particles. Polymeric polymers may be formed from biocompatible and/or biodegradable polymers, copolymers or blends. In one embodiment, polymers capable of forming aerodynamically light particles may be used, such as functionalized polyester graft copolymers and biodegradable polyanhydrides. For example, bulk eroding polymers based on polyesters including poly(hydroxy acids) can be used. Polyglycolic acid (PGA), polylactic acid (PLA) or copolymers thereof may be used to form suspending particles. The polyester may include a charged or functionalizable group, such as an amino acid. For example, suspending particles may be formed of poly(D,L-lactic acid) and/or poly(D,L-lactic-co-glycolic acid) (PLGA), which incorporate a surfactant such as DPPC.

Other potential polymer candidates for use in suspending particles may include polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

The compositions described herein may include two or more species of suspending particles. Even further, compositions according to the present description can include suspending particles that include glycopyrrolate incorporated into the suspending particles. Where active agent is incorporated into suspending particles, the suspending particles will be of a respirable size and can be formulated and produced using, for example, the methods and materials described herein.

Compositions formulated according to the present teachings can inhibit degradation of active agent included therein. For example, in specific embodiments, the compositions described herein inhibit one or more of flocculation, aggregation and the solution mediated transformation of active agent material included in the compositions. The pharmaceutical compositions described herein are suited for respiratory delivery via and MDI in a manner that achieves desirable delivered dose uniformity ("DDU") of LABA and LAMA active agents, including potent and highly potent LABA and LAMA agents throughout emptying of an MDI canister. As is described in detail in the Examples included herein, even when delivering very low doses of LAMA or LABA active agents, compositions described herein can achieve a DDU for the active agent of ±30%, or better throughout emptying of an MDI canister. In one such embodiment, compositions described herein achieve a DDU for the active agent of ±25%, or better throughout emptying of an MDI canister. In yet another such embodiment, compositions described herein achieve a DDU for the active agent of ±20%, or better throughout emptying of an MDI canister.

Pharmaceutical compositions described herein also serve to substantially preserve FPF and FPD performance throughout emptying of an MDI canister, even after being subjected to accelerated degradation conditions. For instance, compositions according to the present description maintain as much as 80%, 90%, 95%, or more, of the original FPF and FPD performance throughout emptying of an MDI canister, even after being subjected to accelerated degradation conditions. Compositions described herein provide the added benefit of achieving such performance while being formulated using non-CFC propellants. In specific embodiments, the compositions described herein achieve desired one or all of a targeted DDU, FPF and FPD performance while being formulated with suspension medium including only one or more non-CFC propellants and without the need to modify the characteristics of the non-CFC propellant, such as by the addition of, for example, one or more cosolvent, antisolvent, solubilizing agent, adjuvant or other propellant modifying material.

In one embodiment, a co-suspension composition as described herein includes: a suspension medium comprising a pharmaceutically acceptable HFA propellant; a plurality of active agent particles comprising glycopyrrolate, including any pharmaceutically acceptable salts, esters, isomers or solvates thereof, suspended in the suspension medium at a concentration sufficient to provide a delivered dose of glycopyrrolate of between about 20 µg and about 150 µg per actuation of the metered dose inhaler; and a plurality of respirable suspending particles comprising perforated microstructures as described herein exhibiting a volume median optical diameter of between about 1.5 µm and about 10 µm, wherein perforated microstructures associate with the plurality of active agent particles to form a co-suspension. In one such embodiment, the glycopyrrolate active agent particles are formed of crystalline glycopyrrolate material. In another such embodiment, the ratio of the total mass of the suspending particles to the total mass of the active agent particles is selected from between about 3:1 and about 15:1 and between about 2:1 and 8:1. In yet another such embodiment, the glycopyrrolate active agent particles are formed of crystalline glycopyrrolate material and the ratio of the total mass of the suspending particles to the total mass of the active agent particles is selected from between about 3:1 and about 15:1 and between about 2:1 and 8:1. In still another such embodiment, the glycopyrrolate active agent particles are formed of crystalline glycopyrrolate material, at least 90% of the glycopyrrolate active agent particles by volume exhibit an optical diameter of less than 7 µm, and the ratio of the total mass of the suspending particles to the total mass of the active agent particles is selected from between about 3:1 and about 15:1 and between about 2:1 and 8:1.

In another embodiment, a co-suspension composition as described herein includes: a suspension medium comprising a pharmaceutically acceptable HFA propellant; a plurality of active agent particles comprising tiotropium, including any pharmaceutically acceptable salts, esters, isomers or solvates thereof, suspended in the suspension medium at a concentration sufficient to provide a delivered dose of glycopyrrolate of between about 5 µg and about 40 µg per actuation of the metered dose inhaler; and a plurality of respirable suspending particles comprising perforated microstructures as described herein exhibiting a volume median optical diameter of between about 1.5 µm and about 10 µm, wherein perforated microstructures associate with the plurality of active agent particles to form a co-suspension. In one such embodiment, the tiotropium active agent particles are formed of crystalline tiotropium material. In another such embodiment, the ratio of the total mass of the suspending particles to the total mass of the active agent particles is selected from between about 3:1 and about 15:1 and between about 2:1 and 8:1. In yet another such embodiment, the tiotropium active agent particles are formed of crystalline tiotropium material and the ratio of the total mass of the suspending particles to the total mass of the active agent particles is selected from between about 3:1 and about 15:1 and between about 2:1 and 8:1. In still another such embodiment, the tiotropium active agent particles are formed of crystalline tiotropium material, at least 90% of the tiotropium active agent particles by volume exhibit an optical diameter of less than 7 µm, and the ratio of the total mass of the suspending particles to the total mass of the active agent particles is selected from between about 3:1 and about 15:1 and between about 2:1 and 8:1.

In another embodiment, a co-suspension composition as described herein includes: a suspension medium comprising a pharmaceutically acceptable HFA propellant; a plurality of active agent particles comprising formoterol, including any pharmaceutically acceptable salts, esters, isomers or solvates thereof, suspended in the suspension medium at a concentration sufficient to provide a delivered dose of formoterol of between about 0.5 µg and about 10 µg per actuation of the metered dose inhaler; and a plurality of respirable suspending particles comprising perforated microstructures as described herein exhibiting a volume median optical diameter of between about 1.5 µm and about 10 µm, wherein perforated microstructures associate with the plurality of active agent particles to form a co-suspension. In one such embodiment, the formoterol active agent particles are formed of crystalline formoterol material. In another such embodiment, the ratio of the total mass of the suspending particles to the total mass of the active agent particles is selected from between about 3:1 and about 15:1 and between about 2:1 and 8:1. In yet another such embodiment, the formoterol active agent particles are formed of crystalline formoterol material and the ratio of the total mass of the suspending particles to the total mass of the active agent particles is selected from between about 3:1 and about 15:1 and between about 2:1 and 8:1. In still another such embodiment, the formoterol active agent particles are formed of crystalline formoterol material, at least 90% of the formoterol active agent particles by volume exhibit an optical diameter of less than 7 µm, and the ratio of the total mass of the suspending particles to the total mass of the active agent particles is selected from between about 3:1 and about 15:1 and between about 2:1 and 8:1.

In one embodiment, a co-suspension composition as described herein includes: a suspension medium comprising a pharmaceutically acceptable HFA propellant; a plurality of active agent particles comprising formoterol, including any pharmaceutically acceptable salts, esters, isomers or solvates thereof, suspended in the suspension medium at a concentration sufficient to provide a delivered dose of formoterol of between about 2 µg and about 10 µg per actuation of the metered dose inhaler; and a plurality of respirable suspending particles comprising perforated microstructures as described herein exhibiting a volume median optical diameter of between about 1.5 µm and about 10 µm, wherein perforated microstructures associate with the plurality of active agent particles to form a co-suspension. In one such embodiment, the formoterol active agent particles are formed of crystalline formoterol material. In another such embodiment, the ratio of the total mass of the suspending particles to the total mass of the active agent particles is selected from between about 3:1 and about 15:1 and between about 2:1 and 8:1. In yet another such embodiment, the formoterol active agent particles are formed of crystalline formoterol material and the ratio of the total mass of the suspending particles to the total mass of the active agent particles is selected from between about 3:1 and about 15:1 and between about 2:1 and 8:1. In still another such embodiment, the formoterol active agent particles are formed of crystalline formoterol material, at least 90% of the formoterol active agent particles by volume exhibit an optical diameter of less than 7 µm, and the ratio of the total mass of the suspending particles to the total mass of the active agent particles is selected from between about 3:1 and about 15:1 and between about 2:1 and 8:1.

In another embodiment, a co-suspension composition as described herein includes: a suspension medium comprising a pharmaceutically acceptable HFA propellant; a plurality of active agent particles comprising salmeterol, including any pharmaceutically acceptable salts, esters, isomers or solvates thereof, suspended in the suspension medium at a concentration sufficient to provide a delivered dose of salmeterol of between about 8 µg and about 40 µg per actuation of the metered dose inhaler; and a plurality of respirable suspending particles comprising perforated microstructures as described herein exhibiting a volume median optical diameter of between about 1.5 µm and about 10 µm, wherein perforated microstructures associate with the plurality of active agent particles to form a co-suspension. In one such embodiment, the salmeterol active agent particles are formed of crystalline salmeterol material. In another such embodiment, the ratio of the total mass of the suspending particles to the total mass of the active agent particles is selected from between about 3:1 and about 15:1 and between about 2:1 and 8:1. In yet another such embodiment, the salmeterol active agent particles are formed of crystalline salmeterol material and the ratio of the total mass of the suspending particles to the total mass of the active agent particles is selected from between about 3:1 and about 15:1 and between about 2:1 and 8:1. In still another such embodiment, the salmeterol active agent particles are formed of crystalline salmeterol material, at least 90% of the salmeterol active agent particles by volume exhibit an optical diameter of less than 7 µm, and the ratio of the total mass of the suspending particles to the total mass of the active agent particles is selected from between about 3:1 and about 15:1 and between about 2:1 and 8:1.

III. Metered Dose Inhaler Systems

As described in relation to the methods provided herein, the compositions disclosed herein may be used in an MDI system. MDIs are configured to deliver a specific amount of a medicament in aerosol form. In one embodiment, an MDI system includes a pressurized, liquid phase formulation-filled canister disposed in an actuator formed with a mouthpiece. The MDI system may include the formulations described herein, which include a suspension medium, glycopyrrolate and at least one species of suspending particles. The canister used in the MDI be any of any suitable configuration, and in one exemplary embodiment, the canister may have a volume ranging from about 5 mL to about 25 mL, such as, for example a canister having a 19 mL volume. After shaking the device, the mouthpiece is inserted into a patient's mouth between the lips and teeth. The patient typically exhales deeply to empty the lungs and then takes a slow deep breath while actuating the cartridge.

Inside an exemplary cartridge is a metering valve including a metering chamber capable of holding a defined volume of the formulation (e.g., 63 µl or any other suitable volume available in commercially available metering valves), which is released into an expansion chamber at the distal end of the valve stem when actuated. The actuator retains the canister and may also include a port with an actuator nozzle for receiving the valve stem of the metering valve. When actuated, the specified volume of formulation travels to the expansion chamber, out the actuator nozzle and into a high-velocity spray that is drawn into the lungs of a patient.

IV. Methods

Methods for formulating pharmaceutical compositions for respiratory delivery of LAMA and LAMA active agents are provided herein. In particular embodiments, such methods involve the steps of providing a suspension medium, active agent particles selected from active agent particles comprising a LAMA and active agent particles comprising a LABA, and one or more species of suspending particles, as described herein, and combining such constituents to form a formulation wherein the active agent particles associate with the suspending particles and co-locate with the suspending particles within the suspension medium such that a co-suspension is formed. In one such embodiment, the association of the glycopyrrolate particles and the suspending particles is such that they do not separate due to their different buoyancies in a propellant. As will be appreciated, the method may include providing two or more species of suspending particles in combination with active agent particles. In another embodiment, the method may include providing two or more species of active agent particles and combining the two or more species of active agent particles with one or more species of suspending particles in a manner that results in a co-suspension. In certain embodiments, the active agent particles consist essentially of a LAMA or LABA active agent as described herein.

In specific embodiments of methods for providing a stabilized composition of a LAMA or LABA active agent for pulmonary delivery, the present disclosure provides methods for inhibiting the solution mediated transformation of the LAMA or LABA active agent in a pharmaceutical composition for pulmonary delivery. In one embodiment, a suspension medium as described herein, such as a suspension medium formed by an HFA propellant, is obtained. Suspending particles are also obtained or prepared as described herein. Active agent particles are also obtained, and the suspension medium, suspending particles and active agent particles are combined to form a co-suspension wherein the active agent particles associate with suspending particles and co-locate with the suspending particles within the continuous phase formed by the suspension medium. When compared to active agent particles contained in the same suspension medium in the absence of suspending particles, co-suspensions according to the present description have been found to exhibit a higher tolerance to solution mediated phase transformation that leads to irreversible crystal aggregation, and thus may lead to improved stability and dosing uniformity.

In further embodiments, methods for forming stabilized compositions of LAMA and LABA active agents for pulmonary delivery include for preserving the FPF and/or FPD of the composition throughout emptying of an MDI canister. In specific embodiments of methods for preserving the FPF and/or FPD provided by a pharmaceutical composition for pulmonary delivery, a respirable co-suspension as described herein is provided which is capable of maintaining the FPD and/or the FPF to within ±20%, ±10%, or even ±5% the initial FPD and/or FPF, respectively, throughout emptying of an MDI canister. Such performance can be achieved even after the co-suspension is subjected to accelerated degradation conditions. In one embodiment, a suspension medium as described herein, such as a suspension medium formed by an HFA propellant, is obtained. Suspending particles are also obtained or prepared as described herein. Active agent particles are also obtained, and the suspension medium, suspending particles and active agent particles are combined to form a co-suspension wherein the glycopyrrolate particles associate with suspending particles and co-locate with the suspending particles within the suspension medium. Even after exposure of such composition to one or more temperature cycling events, the co-suspension maintains an FPD or FPF within ±20%, ±10%, or even ±5% of the respective values measured prior to exposure of the composition to the one or more temperature cycling events.

Methods for preparing an MDI for pulmonary delivery of LAMA or LABA active agent are disclosed. The method of preparing the MDI may include loading a canister, as described herein, with active agent particles and suspending particles. An actuator valve can be attached to an end of the canister and the canister sealed. The actuator valve may be adapted for dispensing a metered amount of the glycopyrrolate pharmaceutical formulation per actuation. The canister can be charged with a pharmaceutically acceptable suspension medium, such as a propellant as described herein. Whereupon the active agent particles and suspending particles yield a stable co-suspension in the suspension medium.

In methods involving pulmonary delivery of a LAMA or LABA active agent using compositions described herein, the compositions may be delivered by an MDI. Therefore, in particular embodiments of such methods, an MDI loaded with a composition described herein is obtained, and a LAMA or LABA active agent is administered to a patient through pulmonary delivery through actuation of the MDI. For example, in one embodiment, after shaking the MDI device, the mouthpiece is inserted into a patient's mouth between the lips and teeth. The patient typically exhales deeply to empty the lungs and then takes a slow deep breath while actuating the cartridge of the MDI. When actuated, the specified volume of formulation travels to the expansion chamber, out the actuator nozzle and into a high-velocity spray that is drawn into the lungs of a patient. In one embodiment the dose of active agent delivered throughout emptying of an MDI canister is not more than 30% greater than the mean delivered dose and is not less than 30% less than the mean delivered dose. Therefore, methods of achieving a desired DDU of glycopyrrolate delivered from an MDI are also provided. In such embodiments, the method may include achieving a DDU for glycopyrrolate delivered from an MDI selected from, for example, a DDU of ±30%, or better, a DDU of ±25%, or better, and a DDU of ±20%, or better.

Methods for treating patients suffering from an inflammatory or obstructive pulmonary disease or condition are provided herein. In specific embodiments, such methods include pulmonary delivery of a pharmaceutical composition described herein, and in certain such embodiments, pulmonary administration of the pharmaceutical composition is accomplished by delivering the composition using an MDI. The disease or condition to be treated can be selected from any inflammatory or obstructive pulmonary disease or condition that responds to the administration of a LAMA or LABA agent. In particular embodiments, the pharmaceutical compositions described herein may be used in treating a disease or disorder selected from asthma, COPD, exacerbation of airways hyper reactivity consequent to other drug therapy, allergic rhinitis, sinusitis, pulmonary vasoconstriction, inflammation, allergies, impeded respiration, respiratory distress syndrome, pulmonary hypertension, pulmonary vasoconstriction, emphysema, and any other respiratory disease, condition, trait, genotype or phenotype that can respond to the administration of a LAMA or LABA, alone or in combination with other therapies. In certain embodiments, the pharmaceutical compositions described herein may be used in treating pulmonary inflammation and obstruction associated with cystic fibrosis.

Additionally, pharmaceutical compositions according to the present description delivered from an MDI provide desirable pharmacodynamic (PD) performance. In particular embodiments, pulmonary delivery of the pharmaceutical compositions described herein results in rapid, significant improvement in the lung capacity, which can be characterized by an improvement in the patient's forced expiratory volume in one second ($FEV_1$). For example, in particular embodiments, methods for achieving a clinically relevant increase in $FEV_1$ are provided, wherein such methods include providing a co-suspension composition comprising a LABA or LAMA active agent as described herein and administering such composition to a patient experiencing pulmonary inflammation or obstruction via an MDI. For purposes of the present disclosure, a clinically relevant increase in $FEV_1$ is any increase of 100 ml or greater, and in certain embodiments of the methods described herein, administration of compositions according to the present description to patient results in a clinically significant increase in $FEV_1$ within 1 hour or less. In other such embodiments, methods for administering a composition as described herein to a patient via an MDI result in a clinically significant increase in FEV1 within 0.5 hours or less. The compositions provided and delivered in such embodiments may include a composition including a LAMA active agent or a composition including a LABA active agent as described herein.

In further embodiments, methods are provided for achieving an increase in $FEV_1$ greater than 100 ml. For example, in certain embodiments, the methods described herein include methods for achieving an $FEV_1$ of 150 ml or greater within a period of time selected from 0.5 hours or less, 1 hour or less, and 1.5 hours or less. In other embodiments, the methods described herein include methods for achieving an $FEV_1$ of 200 ml or greater within a period of time selected from 0.5 hours or less, 1 hour or less, and 1.5 hours or less, and 2 hours or less. In certain such embodiments, a composition comprising a LABA or LAMA active agent as described herein is provided and administered to a patient experiencing pulmonary inflammation or obstruction via an MDI.

In still further embodiments, methods for achieving and maintaining a clinically significantly increase in $FEV_1$ are provided. In particular embodiments, upon administration of a single dose of a LABA or LAMA active agent formulated in a composition as described herein to a patient via an MDI, a clinically significant increase in $FEV_1$ is achieved in a period of time selected from 0.5 hours or less, 1 hour or less, and 1.5 hours or less, and the clinically significant increase in $FEV_1$ is maintained for up 12 hours or more. In certain such embodiments, the increase in $FEV_1$ may be selected from an increase of 150 ml or greater, 200 ml or greater and 250 ml or greater, and the increase in $FEV_1$ remains clinically significant for a time period selected from up to 4 hours, up to 6 hours, up to 8 hours, up to 10 hours, and up to 12 hours, or more. In certain such embodiments, a composition comprising a LABA or LAMA active agent as described herein is provided and administered a patient experiencing pulmonary inflammation or obstruction via an MDI.

Compositions, systems and methods described herein are not only suited to achieving desirable pharmacodynamic performance in short periods of time, but will achieve such results in a high percentage of patients. For example, methods are provided herein for achieving a 10% or greater increase in $FEV_1$ in 50% or more of patients experiencing pulmonary inflammation or obstruction. For example, in particular embodiments, methods for achieving a 10% or greater increase in $FEV_1$ in a patient include providing a co-suspension composition comprising a LABA or LAMA active agent as described herein and administering such composition via an MDI to a patient experiencing pulmonary inflammation or obstruction. In certain such embodiments, administration of the composition results in 10% or greater increase in $FEV_1$ within a period of time selected from 0.5 hours or less, 1 hour or less, 1.5 hours or less, and 2 hours in 50% or more of patients. In other such embodiments, administration of the composition results in 10% or greater increase in $FEV_1$ within a period of time selected from 0.5 hours or less, 1 hour or less, 1.5 hours or less, and 2 or less hours in 60% or more of patients. In still other such embodiments, administration of the composition results in 10% or greater increase in $FEV_1$ within a period of time selected from 0.5 hours or less, 1 hour or less, 1.5 hours or less, and 2 hours or less in 70% or more of patients. In yet other such embodiments, administration of the composition results in 10% or greater increase in $FEV_1$ within a period of time selected from 0.5 hours or less, 1 hour or less, 1.5 hours or less, and 2 or less hours in 80% or more of patients In specific embodiments, the methods described herein facilitate treatment of patients experiencing pulmonary inflammation or obstruction, wherein such methods include providing a co-suspension composition comprising a LABA or LAMA active agent as described herein and administering such composition to a patient experiencing pulmonary inflammation or obstruction via an MDI and result in a high proportion of such patients experiencing either an increase from baseline in $FEV_1$ of at least 200 ml or a 12%, or greater, increase from baseline in $FEV_1$ coupled with total increase in $FEV_1$ of at least 150 ml. In certain such embodiments, administration of the composition results in either an increase from baseline in $FEV_1$ of at least 200 ml or a 12%, or greater, increase from baseline in $FEV_1$ coupled with total increase in $FEV_1$ of at least 150 ml within a period of time selected from 1 hour or less, 1.5 hours or less, 2 hours or less, and 2.5 hours or less in 50% or more of patients. In other such embodiments, administration of the composition results in an increase from baseline in $FEV_1$ of at least 200 ml or a 12%, or greater, increase from baseline in $FEV_1$ coupled with total increase in $FEV_1$ of at least 150 ml within a period of time selected from 1 hour or less, 1.5 hours or less, 2 hours or less, and 2.5 hours or less in 60% or more of patients. In still other such embodiments, administration of the composition results in either an increase from baseline in $FEV_1$ of at least 200 ml or a 12%, or greater, increase from baseline in $FEV_1$ coupled with total increase in $FEV_1$ of at least 150 ml within a period of time selected from 1.5 hours or less, 2 hours or less, 2.5 hours or less, and 3 hours or less in 70% or more of patients. In yet other such embodiments, administration of the composition results in either an increase from baseline in $FEV_1$ of at least 200 ml or a 12%, or greater, increase from baseline in $FEV_1$ coupled with total increase in $FEV_1$ of at least 150 ml within a period of time selected from 1.5 hours or less, 2 hours or less, 2.5 hours or less, and 3 hours or less in 80% or more of patients.

In some embodiments, pharmaceutical compositions according to the present description delivered from an MDI provide improvement in the lung capacity, which can be characterized by an improvement inspiratory capacity (IC), which is defined as the maximal volume of gas that can be taken into the lungs in a full inhalation following a normal expiration. For example, in particular embodiments, methods for achieving a clinically relevant increase in IC are provided, wherein such methods include providing a co-suspension composition comprising a LABA or LAMA active agent as described herein and administering such composition to a patient experiencing pulmonary inflammation or obstruction via an MDI. For purposes of the present disclosure, a clinically relevant increase in IC is any increase of 70 ml or greater, and in certain embodiments of the methods described herein, administration of compositions according to the present description to patient results in a clinically significant increase in IC within 2 hours or less. In other such embodiments, methods for administering a composition as described herein to a patient via an MDI result in a clinically significant increase in IC within 1 hour or less. In other such embodiments, administration of compositions according to the present description to patient results in an increase in IC of 100 ml or greater within a period of time selected from 1 hour or less and 2 hours or less. In still other such embodiments, administration of compositions according to the present description to patient results in an increase in IC of 150 ml or greater within a period of time selected from 1 hour or less and 2 hours or less. In even further such embodiments, administration of compositions according to the present description to patient results in an increase in IC of 300 ml or greater within a period of time selected from 1 hour or less and 2 hours or less. The compositions provided and delivered in such embodiments may include a composition including a LAMA active agent or a composition including a LABA active agent as described herein.

In particular embodiments of the methods described herein, the compositions provided include a LAMA active agent. In such embodiments, the LAMA active agent can be selected from, for example, glycopyrrolate, dexipirronium, tiotropium, trospium, aclidinium, and darotropium, including any pharmaceutically acceptable salts, esters, isomers or solvates thereof. In specific embodiments of the methods described herein, the composition is a co-suspension composition as described herein that includes glycopyrrolate or any pharmaceutically acceptable salt, ester, isomer or solvate thereof. In other specific embodiments of the methods described herein, the composition is a co-suspension composition as described herein that includes tiotropium or any pharmaceutically acceptable salt, ester, isomer or solvate thereof. Where glycopyrrolate or tiotropium is selected as the active agent for use in the compositions produced or administered as part of the methods described herein, the amount of glycopyrrolate or tiotropium included in the composition may be selected from, for example, those amounts specifically disclosed with respect to the pharmaceutical compositions described herein.

In further embodiments of the methods described herein, the compositions provided include a LABA active agent. In such embodiments, the LABA active agent can be selected from, for example, bambuterol, clenbuterol, formoterol, salmeterol, carmoterol, milveterol, indacaterol, and saligenin- or indole-containing and adamantyl-derived $\beta_2$ agonists, including any pharmaceutically acceptable salts, esters, isomers or solvates thereof. In specific embodiments of the methods described herein, the composition is a co-suspension composition as described herein that includes formoterol or any pharmaceutically acceptable salt, ester, isomer or solvate thereof. In other specific embodiments of the methods described herein, the composition is a co-suspension composition as described herein that includes salmeterol or any pharmaceutically acceptable salt, ester, isomer or solvate thereof. Where formoterol or salmeterol is selected as the active agent for use in the compositions produced or administered as part of the methods described herein, the amount of formoterol or salmterol included in the composition may be selected from, for example, those amounts specifically disclosed with respect to the pharmaceutical compositions described herein.

Compositions, methods and systems described herein provide desirable dose efficiency and dose response for LAMA or LABA active agents formulated for pulmonary delivery. For example, pulmonary delivery of glycopyrrolate for treatment of conditions such as COPD has been previously suggested or reported by Schroeckenstein et al., J. Allergy Clin. Immunol., 1988; 82(1): 115-119, Leckie et al., Exp. Opin. Invest. Drugs, 2000; 9(1): 3-23, Skorodin, Arch. Intern. Med., 1993; 153: 814-828, Walker et al., Chest, 1987; 91(1): 49-51, and International Patent Publication WO/1997/039758. These references report a minimum effective dose for glycopyrrolate of 200 µg-1,000 µg. Such dosing requirements are in line with human clinical results reported by Bannister et al. in U.S. Pat. No. 7,229,607, wherein subjects were given a 480 µg dose of glycopyrrolate. As is described in Example 6 provided herein, compositions of glycopyrrolate prepared according to the present description and delivered to human subjects via an MDI achieved quick onset of action and clinically relevant improvements in $FEV_1$ and IC in accordance with the methods detailed herein, even when delivering significantly smaller doses of glycopyrrolate (the largest single dose delivered in the study was 144 µg).

Singh et al. [D Singh, P A Corris, and S D Snape. "NVA237, a once-daily inhaled antimuscarinic, provides 24-hour bronchodilator efficacy in patients with moderate to-severe COPD" Poster presented at the American Thoracic Society International Conference, San Diego, Calif., May 19-24, 2006] reported clinical work wherein glycopyrrolate was administered to human subjects via pulmonary delivery at doses of 20 µg, 125 µg, 250 µg, and 400 µg. Though such doses ranged below the 200 µg threshold previously reported, as is also detailed in Example 6, compositions of glycopyrrolate formulated and delivered as described herein still achieved a relatively improved dose efficiency. For example, changes in $FEV_1$ AUC achieved by glycopyrrolate co-suspensions as described and evaluated in the clinical trial described in Example 6 are compared to those achieved by the compositions of Singh et al. in FIG. 10. The 18 µg glycopyrrolate dose from Example 6 provided significantly better bronchodilator response than the 20 µg dose reported by Singh et al., and the 36 µg and 144 µg glycopyrrolate doses from Example 6 providing comparable bronchodilator response to the 125 µg and 250 µg doses, respectively, reported by Singh et al.

In particular embodiments, methods for achieving desired pharmacodynamic effects are provided, wherein the methods include administering a co-suspension composition as described herein to a patient via a metered dose inhaler, wherein the co-suspension includes glycopyrrolate active agent particles as described herein to a patient via a metered dose inhaler such that a delivered dose of no more than 150 µg glycopyrrolate is administered to the patient. In one embodiment, a method for achieving a clinically significant increase in $FEV_1$ is provided, wherein the method includes administering a co-suspension as described herein comprising glycopyrrolate active agent particles to a patient via a metered dose inhaler such that a delivered dose of no more than 150 µg glycopyrrolate is administered to the patient. In one such embodiment, a delivered dose of no more than 100 µg glycopyrrolate is administered to the patient, and in another embodiment, a delivered dose of no more than 80 µg glycopyrrolate is administered to the patient. Even where doses of no more than 80 µg, no more than 100 µg glycopyrrolate, or no more than 150 µg glycopyrrolate are administered to the patient, in particular embodiments, the clinically significant increase in FEV1 is achieved in 1 hour or less. In some such embodiments, the clinically significant increase in FEV1 is achieved in 0.5 hours or less.

In further embodiments, methods are provided for achieving an increase in $FEV_1$ greater than 100 ml, wherein the methods include administering a co-suspension as described herein comprising glycopyrrolate active agent particles to a patient via a metered dose inhaler such that a delivered dose of no more than 150 µg glycopyrrolate is administered to the patient. For example, in certain embodiments, methods for achieving an $FEV_1$ of 150 ml or greater within a period of time selected from 0.5 hours or less, 1 hour or less, and 1.5 hours or less, are provided, wherein the methods include administering a co-suspension as described herein comprising glycopyrrolate active agent particles to a patient via a metered dose inhaler such that a delivered dose of no more than 150 µg glycopyrrolate is administered to the patient. In other embodiments, the methods described herein include methods for achieving an $FEV_1$ of 200 ml or greater within a period of time selected from 0.5 hours or less, 1 hour or less, and 1.5 hours or less, and 2 hours or less, wherein the methods include administering a co-suspension as described herein comprising glycopyrrolate active agent particles to a patient via a metered dose inhaler such that a delivered dose of no more than 150 µg glycopyrrolate is administered to the patient.

In still further embodiments, methods for achieving and maintaining a clinically significantly increase in $FEV_1$ are provided, wherein the methods include administering a co-suspension as described herein comprising glycopyrrolate active agent particles to a patient via a metered dose inhaler such that a delivered dose of no more than 150 µg glycopyrrolate is administered to the patient. In certain such embodiments, upon administration of a single delivered dose of glycopyrrolate of no more than 150 µg, a clinically significant increase in $FEV_1$ is achieved in a period of time selected from 0.5 hours or less, 1 hour or less, and 1.5 hours or less, and the clinically significant increase in $FEV_1$ is maintained for up 12 hours or more. For example, in particular embodiments, the increase in $FEV_1$ may be selected from an increase of 150 ml or greater, 200 ml or greater and 250 ml or greater, and the increase in $FEV_1$ remains clinically significant for a time period selected from up to 4 hours, up to 6 hours, up to 8 hours, up to 10 hours, and up to 12 hours, or more.

Methods for achieving an increase from baseline in $FEV_1$ of at least 200 ml or a 12%, or greater, increase from baseline in $FEV_1$ coupled with total increase in $FEV_1$ of at least 150 ml are also provided, wherein the methods include administering a co-suspension as described herein comprising glycopyrrolate active agent particles to a patient via a metered dose inhaler such that a delivered dose of no more than 150 µg glycopyrrolate is administered to the patient. In certain such embodiments, administration of a delivered dose of no more than 150 µg glycopyrrolate from a co-suspension as described herein via a metered dose inhaler results in either an increase from baseline in $FEV_1$ of at least 200 ml or a 12%, or greater, increase from baseline in $FEV_1$ coupled with total increase in $FEV_1$ of at least 150 ml within a period of time selected from 1 hour or less, 1.5 hours or less, 2 hours or less, and 2.5 hours or less in 50% or more of patients. In other such embodiments, administration of a delivered dose of no more than 150 µg glycopyrrolate from a co-suspension as described herein via a metered dose inhaler results in an increase from baseline in $FEV_1$ of at least 200 ml or a 12%, or greater, increase from baseline in $FEV_1$ coupled with total increase in $FEV_1$ of at least 150 ml within a period of time selected from 1 hour or less, 1.5 hours or less, 2 hours or less, and 2.5 hours or less in 60% or more of patients. In still other such embodiments, administration of a delivered dose of no more than 150 µg glycopyrrolate from a co-suspension as described herein via a metered dose inhaler results in either an increase from baseline in $FEV_1$ of at least 200 ml or a 12%, or greater, increase from baseline in $FEV_1$ coupled with total increase in $FEV_1$ of at least 150 ml within a period of time selected from 1.5 hours or less, 2 hours or less, 2.5 hours or less, and 3 hours or less in 70% or more of patients. In yet other such embodiments, administration of a delivered dose of no more than 150 µg glycopyrrolate from a co-suspension as described herein via a metered dose inhaler results in either an increase from baseline in $FEV_1$ of at least 200 ml or a 12%, or greater, increase from baseline in $FEV_1$ coupled with total increase in $FEV_1$ of at least 150 ml within a period of time selected from 1.5 hours or less, 2 hours or less, 2.5 hours or less, and 3 hours or less in 80% or more of patients.

Methods for achieving a clinically significant increase in IC are provided, wherein the methods include administering a co-suspension as described herein comprising glycopyrrolate active agent particles to a patient via a metered dose inhaler such that a delivered dose of no more than 150 µg glycopyrrolate is administered to the patient. In certain such embodiments, administration of a delivered dose of no more than 150 µg glycopyrrolate from a co-suspension as described herein via a metered dose inhaler results in a clinically significant increase in IC within 1 hour or less. In other such embodiments, administration of a delivered dose of no more than 150 µg glycopyrrolate from a co-suspension as described herein via a metered dose inhaler results in an increase in IC of 100 ml or greater within a period of time selected from 1 hour or less and 2 hours or less. In still other such embodiments, administration of a delivered dose of no more than 150 µg glycopyrrolate from a co-suspension as described herein via a metered dose inhaler results in an increase in IC of 150 ml or greater within a period of time selected from 1 hour or less and 2 hours or less. In even further such embodiments, administration of a delivered dose of no more than 150 µg glycopyrrolate from a cosuspension as described herein via a metered dose inhaler results in an increase in IC of 300 ml or greater within a period of time selected from 1 hour or less and 2 hours or less.

The specific examples included herein are for illustrative purposes only and are not to be considered as limiting to this disclosure. Moreover, the compositions, systems and methods disclosed herein have been described in relation to certain embodiments thereof, and many details have been set forth for purposes of illustration, it will be apparent to those skilled in the art that the invention is susceptible to additional embodiments and that certain of the details described herein may be varied without departing from the basic principles of the invention. Any active agents and reagents used in the following examples are either commercially available or can be prepared according to standard literature procedures by those skilled in the art of organic synthesis. The entire contents of all publications, patents, and patent applications referenced herein are hereby incorporated herein by reference.

Example 1

Active agent particles formed of glycopyrrolate (Pyrrolidinium, 3-((cyclopentylhydroxyphenylacetyl)oxy)-1,1-dimethyl-, bromide) were formed by micronizing glycopyrrolate using a jet mill. The particle size distribution of the micronized glycopyrrolate (GP) was determined by laser diffraction. 50% by volume of the micronized particles exhibited an optical diameter smaller than 2.1 µm, 90% by volume were smaller than 5 µm.

Suspending particles were manufactured as follows: 500 mL of a fluorocarbon-in water emulsion of PFOB (perfluoroctyl bromide) stabilized by a phospholipid was prepared. 18.7 g of the phospholipid, DSPC (1,2-Distearoyl-sn-Glycero-3-Phosphocholine), and 1.3 g of calcium chloride were homogenized in 400 mL of hot water (75° C.) using a high shear mixer. 100 mL of PFOB were added slowly during homogenization. The resulting coarse emulsion was then further homogenized using a high pressure homogenizer (Model C3, Avestin, Ottawa, Calif.) at pressures of up to 170 MPa for 5 passes.

The emulsion was spray dried in nitrogen using the following spray drying conditions: Inlet temperature 95° C., outlet temperature 72° C., emulsion feed rate 2.4 mL/min, total gas flow 525 L/min. The particle size distribution of the suspending particles was determined by laser diffraction. 50% by volume of the suspending particles were smaller than 2.9 µm, the Geometric Standard Deviation of the distribution was 1.8.

Metered dose inhalers were prepared by weighing the target masses of micronized GP particles and suspending particles into fluorinated ethylene polymer (FEP) coated aluminum canisters (Presspart, Blackburn, UK) with 19 mL volume. The target masses and the target delivered dose assuming 20% actuator deposition are given in Table 1 for five different configurations (configurations 1A through 1C representing different suspensions of GP particles and suspending particles; configuration 1D representing GP particles alone; configuration 1E representing suspending particles alone). The canisters were crimp sealed with 63 µl valves (#BK 357, Bespak, King's Lynn, UK) and filled with 12.4 g of HFA 134a (1,1,1,2-tetrafluoroethane) (Ineos Fluor, Lyndhurst, UK) by overpressure through the valve stem. After injecting the propellant, the canisters were sonicated for 15 seconds and agitated on a wrist action shaker for 30 minutes. The canisters were fitted with polypropylene actuators with a 0.3 mm orifice (#BK 636, Bespak, King's Lynn, UK). Additional inhalers for visual observation of suspension quality were prepared using glass vials.

TABLE 1

Results for Glycopyrrolate Co-suspensions of Example 1

| Configuration ID | GP (mg/can) | Suspending particles (mg/can) | Target delivered dose (µg) | Delivered Dose (µg) | FPF (%) | MMAD (µm) |
|---|---|---|---|---|---|---|
| 1A | 3.4 | 61 | 16.5 | 17.8 | 41.3 | 3.7 |
| 1B | 4.1 | 61 | 20 | 19.4 | 42.0 | 3.9 |
| 1C | 4.1 | 15 | 20 | 19.2 | 42.7 | 3.2 |
| 1D | 4.1 | 0 | 20 | 11.1-15.3 | 27.0 | 3.3 |
| 1E | 0 | 61 | — | — | 53.6 * | 3.2 |

* Based on DSPC assay.

Aerosol performance was assessed shortly after manufacturing in accordance with USP <601> (United States Pharmacopeia Monograph 601). A Next Generation Impactor (NGI) operated at a flow rate of 30 L/min was used for determination of particle size distribution. Sample canisters were seated into an actuator with two waste actuations and two additional waste priming actuations. Five actuations were collected in the NGI with a USP throat attached. The valve, actuator, throat, NGI cups, stages, and filter were rinsed with volumetrically dispensed solvent. The sample solutions were assayed using a drug specific chromatographic method. The fine particle fraction was defined using the sum of stages 3 through filter. Delivered dose uniformity through use testing was performed using a Dose Uniformity Sampling Apparatus as described in USP <601>. Inhalers were seated and primed as described before. Two actuations were collected and assayed at beginning, middle and end of use.

Visual observation of the co-suspended configurations (1A, 1B, 1C) showed no sedimentation of drug crystals. The suspension flocculated slowly and formed a homogeneous, single cream layer similar to the comparator configuration 1E, which included suspending particles suspended alone. In contrast, the micronized GP particles alone (configuration 1D) flocculated and sedimented quickly. Configuration 1B showed no indication of separation of GP particles from the suspending particles even after centrifugation at 35 g for 20 minutes. The same result was observed (i.e., lack of GP particle separation) when centrifuged up to 200 g. Configuration 1C (low suspending concentration) showed a small amount of GP crystals settling out after centrifugation at 35 g for 20 minutes.

While the co-suspended configurations achieved a delivered dose within 10% of target, the GP particles suspended alone showed much higher variability in delivered dose in a range significantly below target. The fine particle fraction relative to configuration 1D was improved by more than 50%. The MMADs of the co-suspended configurations were acceptable and depended on the suspension concentration of the suspending particles. The delivered dose uniformity through use was tested for configurations 1B and 1C. All individual delivered doses were within ±20% of mean. The results showed that the drug crystals forming the GP particles associate to the suspending particles, a co-suspension was formed, and the aerosol performance of the co-suspension was mostly determined by the suspending particles.

The association between GP crystals and suspending particles was strong enough to overcome buoyancy forces, as it was observed that GP crystals do not separate from the perforated microstructures and settling of the crystals is inhibited.

Example 2

Glycopyrrolate (GP) particles were formed by micronization using a jet mill. Suspending particles were manufactured as described in Example 1. The particle size distribution of the micronized GP was determined by laser diffraction. 50% by volume of the micronized particles exhibited an optical diameter smaller than 1.7 µm, 90% by volume exhibited an optical diameter smaller than 4.1 µm. Five different lots of metered dose inhalers were different lots were made. For configurations 2A, 2B and 2C the total concentration of DSPC, $CaCl_2$, and GP in the feedstock was 40 mg/mL, for configuration 2D and 2E this concentration was doubled.

Metered dose inhalers were prepared by weighing the target masses of GP particles and suspending particles into canisters as described in Example 1. No further excipients were used. The target masses were 4 mg/canister for GP particles and 60 mg/canister for the suspending particles, resulting in a suspending particle to GP particle ratio of 15 for configurations 2A and 2D. The target masses were 5.1 mg/canister for GP particles and 51 mg/canister for the suspending particles, resulting in a suspending particle to GP particle ratio of 10 for configuration 2B. The target masses were 8 mg/canister for GP particles and 60 mg/canister for the suspending particles, resulting in a suspending particle to GP particle ratio of 7.5 for configurations 2C and 2E. Propellant and container closure system were as described in Example 1.

The GP crystals were placed in HFA 134a in a canister under pressure and were equilibrated for 3 weeks at room temperature to determine their solubility in the propellant. The samples were filtered under pressure at ambient temperature through filters with a pore width of 0.22 µm. The filtrate was evaporated and the GP dissolved in methanol and chromatographically analyzed. A solubility of 0.17±0.07 µg/g was found. Using this value it was determined that 2.1 µg or 0.05% of GP present in the canister dissolved in the propellant. Previous articles teach that microcrystalline material with a measurable solubility in the propellant will not be physically stable due to solution mediated transformation [N. C. Miller, The Effects of Water in Inhalation Suspension Aerosol Formulations, in: P. A. Byron, Ed., Respiratory Drug Delivery, CRC Press, 1990, p 250], or that actives with solubility's above 0.1 µg/g should be formulated with an adjuvant to prevent a solution mediated transformation [P. Rogueda, Novel Hydrofluoroalkane Suspension Formulations for Respiratory Drug Delivery, Expert Opin. Drug Deliv. 2, 625-638, 2005].

The filled metered dose inhalers were stored valve down without overwrap at two different conditions: 1) refrigerated at 5° C.; and 2) room temperature at 25° C./60% RH. Aerosol performance and delivered dose uniformity tests as described in Example 1 were carried out at different time points. The results, which are summarized in Table 2, show a stable fine particle fraction at refrigerated and room temperature conditions.

TABLE 2

Fine particle fraction of configurations in Example 2

| # | Storage | FPF in % | | | |
|---|---|---|---|---|---|
| | | Initial | 2 months | 3 months | 6 months |
| 2A | 5° C. | 49 | 51 | 52 | — |
| | 25° C./60% RH | | 48 | 51 | — |
| 2B | 25° C./60% RH | 50 | 46 | 49 | 48 |
| 2D | 5° C. | 51 | 54 | 54 | — |
| | 25° C./60% RH | | 46 | 49 | 49 |

Configurations 2C and 2E were subjected to a temperature cycling test. The canisters were subjected to −5° C. and 40° C. alternating between temperatures every 6 hours for a total duration of twelve weeks. Fine particle fraction was 53% for both configurations at the beginning of the study. After twelve weeks of cycling the FPF was unchanged, i.e. at 55% for configuration 2C and at 53% for configuration 2E.

Figure 2:
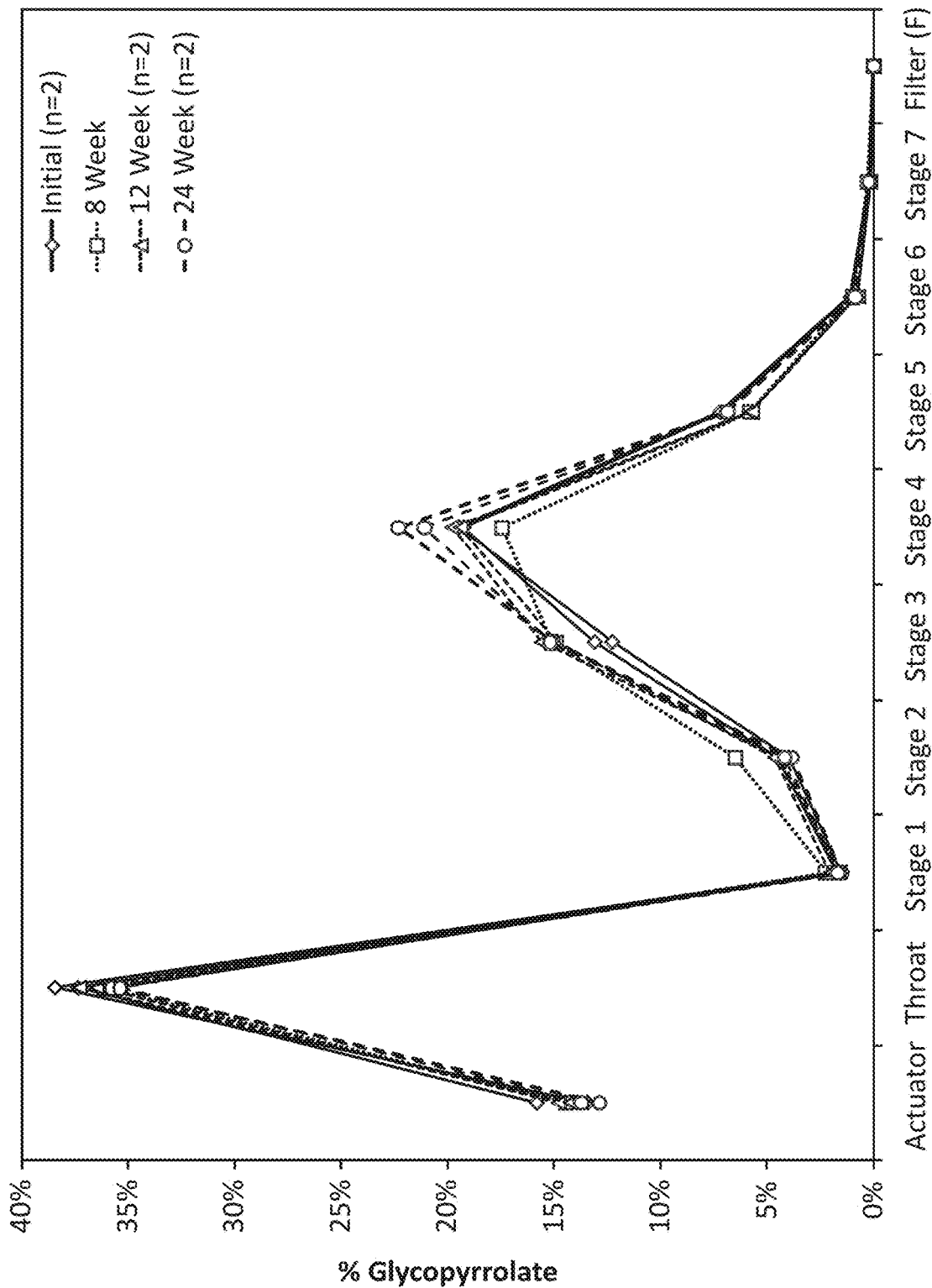
FIG. 2 is a graph, which depicts the particle size distribution exhibited by an exemplary co-suspension composition according to the present description, which included glycopyrrolate, a long-acting muscarinic antagonist, as the active agent. Co-suspension MDIs were subjected to temperature cycling conditions (alternating 6 h hold time at −5 or 40° C.) for 24 weeks.

The delivered dose uniformity through use was tested at the 1, 2 and 6 month time points. All individual delivered doses were within ±20% of mean. FIGS. 1 and 2 show the aerosol particle size distributions as measured by the NGI for configurations 2A and 2B, respectively. Also shown are the amounts of drug recovered from actuator, and from the induction port (throat) and its mouth piece adaptor. Recovered masses are expressed as percent of nominal dose. For configuration 2A, aerodynamic particle size distribution individual replicates are shown at 4, 8 and 12 weeks and at 8, 12 and 24 week for configuration 2B. Though there is a measurable fraction of the suspended GP dissolved in the propellant, there is no evidence of a coarsening of the size distributions. Moreover, as evidenced by these Examples, the aerosol performance of a co-suspension at suitable suspending particle to GP ratios is determined largely by the suspending particles.

Example 3

Several similar batches of suspending particles were made as described in Example 1. The suspending particles were combined with glycopyrrolate (GP) particles that were micronized to different extents, using two different types of jet mills with various milling parameters. The optical diameter and particle size distribution of the micronized GP particles was determined by laser diffraction. Table 3 lists the $d_{50}$ and $d_{90}$ values for the different lots of micronized material used. $d_{50}$ and $d_{90}$ denote the particle size at which the cumulative volume distribution reported by the particle sizing instrument reaches 50% and 90% respectively.

Twelve different lots of metered dose inhalers were prepared as described in Example 1. In all cases the suspension concentration of GP particles in HFA 134a was in the range of 0.32-0.45 mg/mL and the suspension concentration of the suspending particles was in the range of 5.8-6.1 mg/mL. The configurations were deemed similar enough to pool the data for a meta-analysis presented in this Example.

The filled metered dose inhalers were stored valve down without overwrap at two different conditions: refrigerated at 5° C. and controlled room temperature at 25° C./60% RH. Aerosol performance tests as described in Example 1 were carried out at different time points. The results did not show any statistically significant trend as a function of time up to twelve weeks of storage. No difference between room temperature storage and refrigerated storage was discernible. Hence, results from different stress conditions and time points were pooled to determine how the particle size distribution of the micronized material affects aerosol performance.

Table 3 summarizes the MMAD results of the meta-analysis. The first column describes the six different configurations. The second column identifies how many individual lots were used in the compilation of the data for the respective configuration. The third column lists the number of individual MMAD determinations used to calculate the average MMAD for the respective configuration. Columns four and five show the $d_{90}$ and $d_{50}$ of the micronized material used to manufacture the co-suspensions. The results are sorted by $d_{90}$ value from coarse to fine. The last two columns display the average MMAD and standard deviation.

TABLE 3

Pooled MMAD results for 12 glycopyrrolate co-suspensions, sorted by the $d_{90}$ of the micronized glycopyrrolate particles.

| Lot ID | number of lots | Number of MMAD measurements | $d_{90}$ (μm) | $d_{50}$ (μm) | Average MMAD (μm) | SD |
|---|---|---|---|---|---|---|
| 3A | 3 | 21 | 5.0 | 1.8 | 4.0 | 0.28 |
| 3B | 2 | 9 | 4.9 | 2.1 | 4.1 | 0.37 |
| 3C | 1 | 6 | 4.8 | 1.8 | 3.6 | 0.12 |
| 3D | 1 | 4 | 4.3 | 1.7 | 3.5 | 0.22 |
| 3E | 3 | 20 | 4.1 | 1.6 | 3.7 | 0.28 |
| 3F | 2 | 10 | 3.5 | 1.7 | 3.6 | 0.10 |

These results show a weak dependence of MMAD on the $d_{90}$ of the micronized material. A similar analysis for the $d_{50}$ showed no statistically significant trend. It can be concluded that changes in the size distribution of the micronized material (e.g., different micronized material lots, or induced by solution mediated transformations) lead to only minor differences in the size distribution of the aerosol emitted from the metered dose inhaler.

Example 4

Micronized glycopyrrolate (GP) particles were formed tested as described in Example 1. The optical diameter of the micronized GP particles was determined and 50% by volume of the micronized GP particles were smaller than 1.7 μm, 90% by volume were smaller than 3.8 μm.

Five batches of suspending particles were made as described in Example 1. The batches differed in concentration, $C_F$, and volume fraction of PFOB, $V_{PFOB}$, of the feed emulsion prior to spray drying, ranging from 20 mg/mL to 160 mg/mL and 20% to 40%, respectively. The different configurations are described in Table 4.

Metered dose inhalers were prepared by weighing the target masses of micronized GP and suspending particles into coated glass vials with 15 mL volume. The target suspension concentrations and suspending particle to GP ratios are given in Table 4 for the 26 different vials tested. The canisters were crimp sealed with 63 μl valves (Valois, Les Vaudreuil, France) and filled with 10 g or 12 g of HFA 134a (1,1,1,2-tetrafluoroethane) (Ineos Fluor, Lyndhurst, UK) by overpressure through the valve stem. After injecting the propellant, the canisters were sonicated for 15 seconds and agitated on a wrist action shaker for 30 minutes.

As formulated alone in Example 1, micronized GP particles flocculated and sedimented quickly. The glass vials in this example were left to settle for at least 24 h without agitation and then it was tested by visual observation whether the crystal, GP particles were co-suspended completely. For the vials marked with "Yes" in Table 4, no GP particles were observed at the bottom of the vials, except for very few foreign particulates in some vials. Occasional foreign particles were also visible in a similar very low amount in vials filled with suspending particles only. For the vials marked "Partial," a fraction of the GP particles was visible at the bottom of the vial.

TABLE 4

Co-suspension observations for glycopyrrolate configurations with various suspending particle to glycopyrrolate particle ratios.

| # | $C_F$ in mg/mL | $V_{PFOB}$ (%) | $C_S$ (mg/mL) Suspending particle | Suspending particle to glycopyrrolate particle ratio | Co-suspension |
|---|---|---|---|---|---|
| 4A | 20 | 40 | 1.8 | 3.8 | Partial |
|  | 20 | 40 | 7.2 | 15 | Yes |
| 4B | 40 | 40 | 3.0 | 1.9 | Partial |
|  | 40 | 40 | 1.8 | 3.8 | Partial |
|  | 40 | 40 | 3.0 | 3.8 | Yes |
|  | 40 | 40 | 6.0 | 3.8 | Yes |
|  | 40 | 40 | 9.0 | 5.6 | Yes |

| | $C_F$ in mg/mL | $V_{PFOB}$ (%) | $C_S$ (mg/mL) | Suspending particle to glycopyrrolate particle ratio | Co-suspension |
|---|---|---|---|---|---|
|  | 40 | 40 | 3.0 | 7.5 | Yes |
|  | 40 | 40 | 6.0 | 7.5 | Yes |
|  | 40 | 40 | 9.0 | 11.3 | Yes |
|  | 40 | 40 | 6.0 | 15 | Yes |
|  | 40 | 40 | 7.2 | 15 | Yes |
|  | 40 | 40 | 9.0 | 22.5 | Yes |
| 4C | 80 | 20 | 3.0 | 1.9 | Partial |
|  | 80 | 20 | 3.0 | 3.8 | Partial |
|  | 80 | 20 | 6.0 | 3.8 | Yes |
|  | 80 | 20 | 9.0 | 5.6 | Yes |
|  | 80 | 20 | 3.0 | 7.5 | Yes |
|  | 80 | 20 | 6.0 | 7.5 | Yes |
|  | 80 | 20 | 9.0 | 11.3 | Yes |
|  | 80 | 20 | 6.0 | 15 | Yes |
|  | 80 | 20 | 9.0 | 22.5 | Yes |
| 4D | 80 | 40 | 1.8 | 3.8 | Partial |
|  | 80 | 40 | 7.2 | 15 | Yes |
| 4E | 160 | 40 | 1.8 | 3.8 | Partial |
|  | 160 | 40 | 7.2 | 15 | Yes |

Example 5

Glycopyrrolate (GP) particles were micronized with a jetmill and tested as described in Example 1. 50% by volume of the micronized particles exhibited an optical diameter smaller than 1.7 μm, 90% by volume exhibited an optical diameter smaller than 4.4 μm.

Six batches of suspending particles were made by spray drying as described in Example 1. Configuration 5A was spray dried from an emulsion. Configuration 5B was manufactured in a similar fashion but using dipalmitoylphosphatidylcholine (DPPC) instead of DSPC. Configuration 5C was spray dried from an ethanolic solution. For configurations 5D, 5E, and 5F, saccharides were spray dried from aqueous solution. The spray drying parameters for all configurations are given in Table 5a.

TABLE 5a

Suspending particle configurations used in Example 5.

| | | | Spray Drying Parameters | | | | |
|---|---|---|---|---|---|---|---|
| Lot # | Powder composition (% w/w) | Feed composition (% v/v) | $C_F$ (mg/mL) | Feed rate (mL/min) | $T_{in}$ (° C.) | $T_{out}$ (° C.) | Total Gas Flow (L/min) |
| 5A | 93.5% DSPC 6.5% CaCl$_2$ | 80% H$_2$0 20% PFOB | 40 | 2.4 | 95 | 72 | 526 |
| 5B | 92.9% DPPC 7.1% CaCl$_2$ | 70% H$_2$0 30% PFOB | 60 | 2.4 | 95 | 67 | 525 |
| 5C | 100% DSPC | 95% Ethanol 5% PFOB | 100 | 5 | 95 | 70 | 520 |
| 5D | 100% Lactose | 100% H$_2$0 | 100 | 4 | 95 | 70 | 668 |
| 5E | 100% Trehalose | 100% H$_2$0 | 10 | 2.4 | 100 | 68 | 527 |
| 5F | 100% Trehalose | 100% H$_2$0 | 89 | 4 | 100 | 71 | 670 |

The particle size distribution of the suspending particles was determined by laser diffraction. The volume median optical diameter, VMD, and geometric standard deviation, GSD, for the different configurations are given in Table 5b.

TABLE 5b

Characteristics of suspending particle configurations used in Example 5.

| Lot # | VMD (µm) | GSD | Separation | Co-suspension | Comment |
|---|---|---|---|---|---|
| 5A | 3.6 | 1.8 | Creams | Yes | No or few crystals visible on bottom of vials |
| 5B | 3.6 | 1.8 | Creams | Yes | |
| 5C | 1.2 | 1.9 | Creams | Partial | |
| 5D | 1.7 | 2.3 | Sediments | Yes | Causes GP crystals to sediment with the suspending particles |
| 5E | 0.9 | 1.7 | Sediments | Yes | |
| 5F | 1.7 | 2.4 | Sediments | Yes | |

Figure 3:
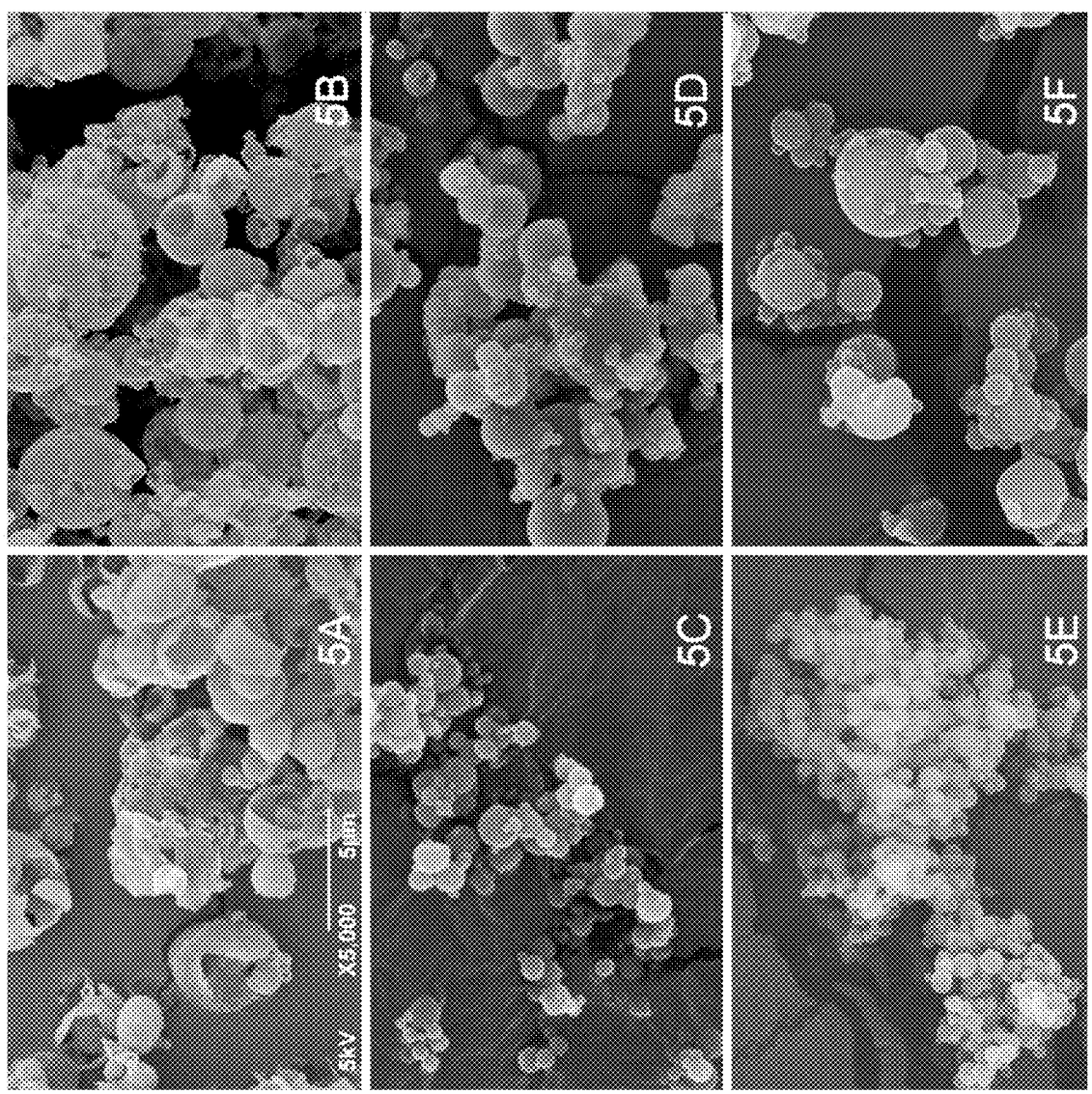
FIG. 3 provides a micrograph illustrating the morphologies of a variety of suspending particles prepared according to Example 5.
Figure 4:
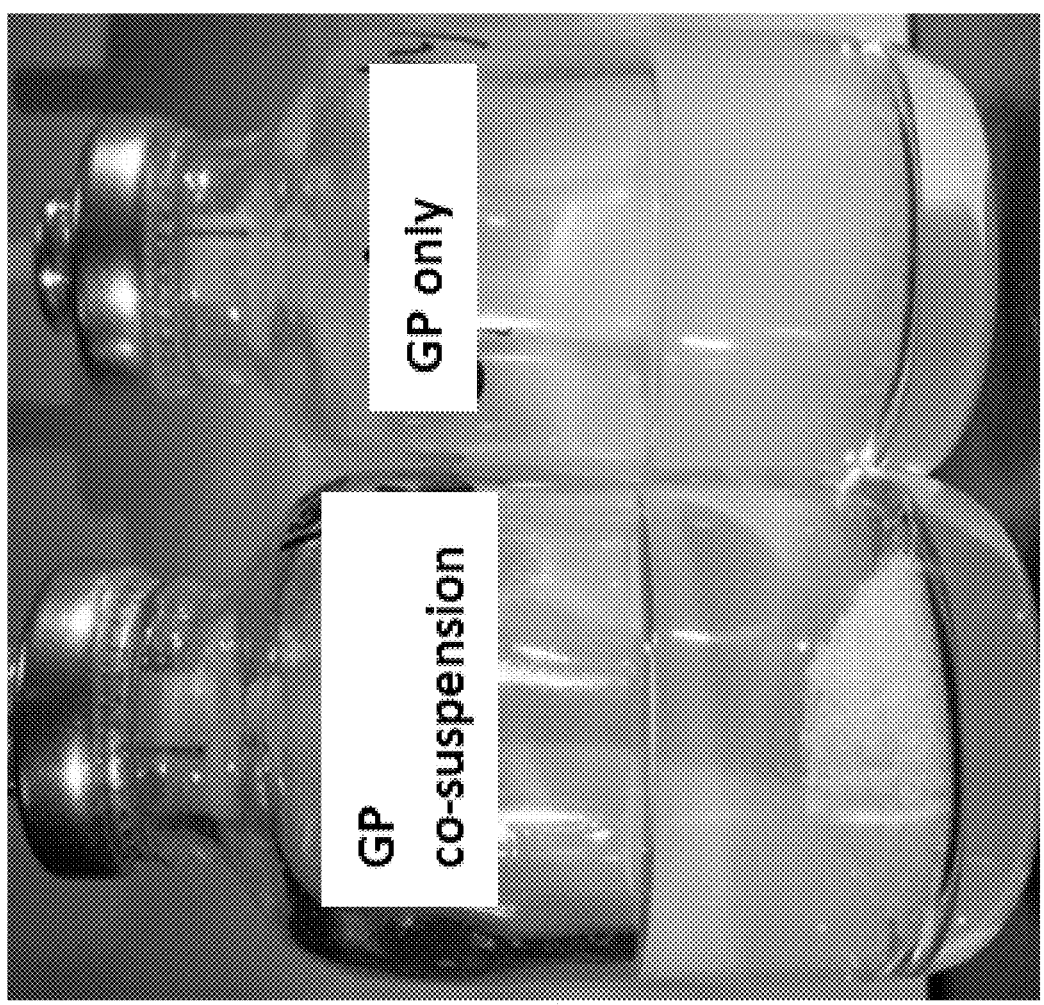
FIG. 4 is a photograph of two vials that allows visualization of a co-suspension formed using active agent particles formed using glycopyrrolate and suspending particles formed using a saccharide.

Electron micrographs of the suspending particles showed a variety of morphologies, summarized in FIG. 3. The particles that were spray dried from emulsion, 5A and 5B, had high porosity and low density. The DSPC particle spray dried from an ethanolic solution, 5C, showed a much smaller particle size with no noticeable porosity, indicating a high density. All saccharides produced smooth particles with no visible porosity. Configuration 5E had the smallest particles, as expected due to its low feed concentration.

Metered dose inhalers were prepared by weighing the 4 mg of micronized GP particles and 60 mg of suspending particles into coated glass vials with 15 mL volume. The canisters were crimp sealed with 63 µl valves (Valois DF30/63 RCU, Les Vaudreuil, France) and filled with 9.5 mL of HFA 134a (Ineos Fluor, Lyndhurst, UK) by overpressure through the valve stem. After injecting the propellant, the canisters were sonicated for 15 seconds and agitated on a wrist action shaker for 30 minutes. Additional inhalers with suspending particles only were manufactured as control for each configuration.

The suspending particles in Examples 5A, 5B, and 5C, have true densities lower than the propellant. They formed a cream layer and were tested for the presence of a co-suspension as described in Example 4. No GP particles were visible at the bottom of the vials for configuration 5A and 5B. Configuration 5C formed a partial co-suspension.

The saccharide particles sediment because they have a higher true density than the propellant. However, all control vials for the saccharide configurations showed a significantly faster sedimentation rate than micronized GP particles alone. In configurations 5D, 5E, and 5F, the sedimentation rate was similar to that of the control vials with the suspending particles alone and faster than the micronized GP particles alone, demonstrating the association of the GP crystals with the suspending particles. A co-suspension was formed in these cases. FIG. 4 shows an example of this behavior for configuration 5D. The glass vial was observed one minute after agitation. The co-suspension has already settled leaving a clear propellant layer, while in the control containing GP particles alone, most of the crystals are still suspended in the propellant.

Example 6

Pharmaceutical compositions according to the present description were evaluated in a multi-center clinical trial. MDI devices containing a pharmaceutical composition of glycopyrrolate prepared according to the present description were provided.

Suspending particles used were prepared in a similar manner described in Example 1. MDI manufacturing was accomplished using a drug addition vessel (DVA) by first adding half of Suspending particle quantity, next filling the microcrystalline GP, and lastly adding the remaining half of suspending particles to the top. Materials were added to the vessel in a humidity controlled environment of <10% RH. The DAV was then connected to a 4 L suspension vessel and flushed with HFA 134a propellant and then mixed. The temperature inside the vessel was maintained at 21-23° C. throughout the entire batch production. After recirculation of the batch for 30 min canisters were filled with the suspension mixture through 50 μL EPDM valves. Sample canisters were then selected at random for total canister assay to ensure correct formulation quantities. The freshly manufactured co-suspension MDI batch was then placed on one week quarantine before initial product performance analysis.

The composition was formulated and the MDI devices configured to provide a dose of 18 μg glycopyrrolate per MDI actuation.

The study was a randomized, double-blind, four-period, six-treatment, placebo and active-controlled crossover study which evaluated single administration of 4 ascending doses of glycopyrrolate in patients with mild to moderate COPD compared to placebo and open label tiotropium (18 μg via the Spiriva Handihaler) as an active control. The six study treatments were Glycopyrrolate MDI at doses of 18, 36, 72 and 144 μg were achieved by one, two, four or eight consecutive actuations of the 18 μg per actuation Glycopyrrolate MDI. Tiotropium Handihaler at 18 μg, and Placebo MDI, which was identical to the Glycopyrrolate MDI but without glycopyrrolate. Each patient was randomized to one of six possible sequences that included four of the study treatments. Each sequence included two or three Glycopyrrolate MDI doses, which were administered in ascending order to each patient. Glycopyrrolate MDI and Placebo MDI treatments were blinded and tiotropium was open label. Thirty-three patients were enrolled and analyzed for safety; thirty patients were analyzed for efficacy. Peak improvement in $FEV_1$ relative to test day baseline ($FEV_1$ is the maximum volume of air exhaled during the first second of maximum effort from a maximum inhalation), time to onset of action, time to peak $FEV_1$, $FEV_1AUC_{0-12}$, $FEV_1AUC_{0-24}$, $FEV_1AUC_{12-24}$, 12 and 24-hour trough $FEV_1$, and similar analyses for peak expirator flow rate (PEFR) and FVC, as well as peak improvement in inspiratory capacity (IC) were evaluated. Blood samples were collected pre-dose and 2, 6, 20 minutes, and 1, 2, 4, 8, 12, and 24 hours post-dose for determining plasma concentrations used to calculate PK parameters. The ratios of clinical spirometry outcomes (FEV1) to glycopyrrolate PK outcomes (AUC0-12 and $C_{max}$) were determined.

Figure 5:
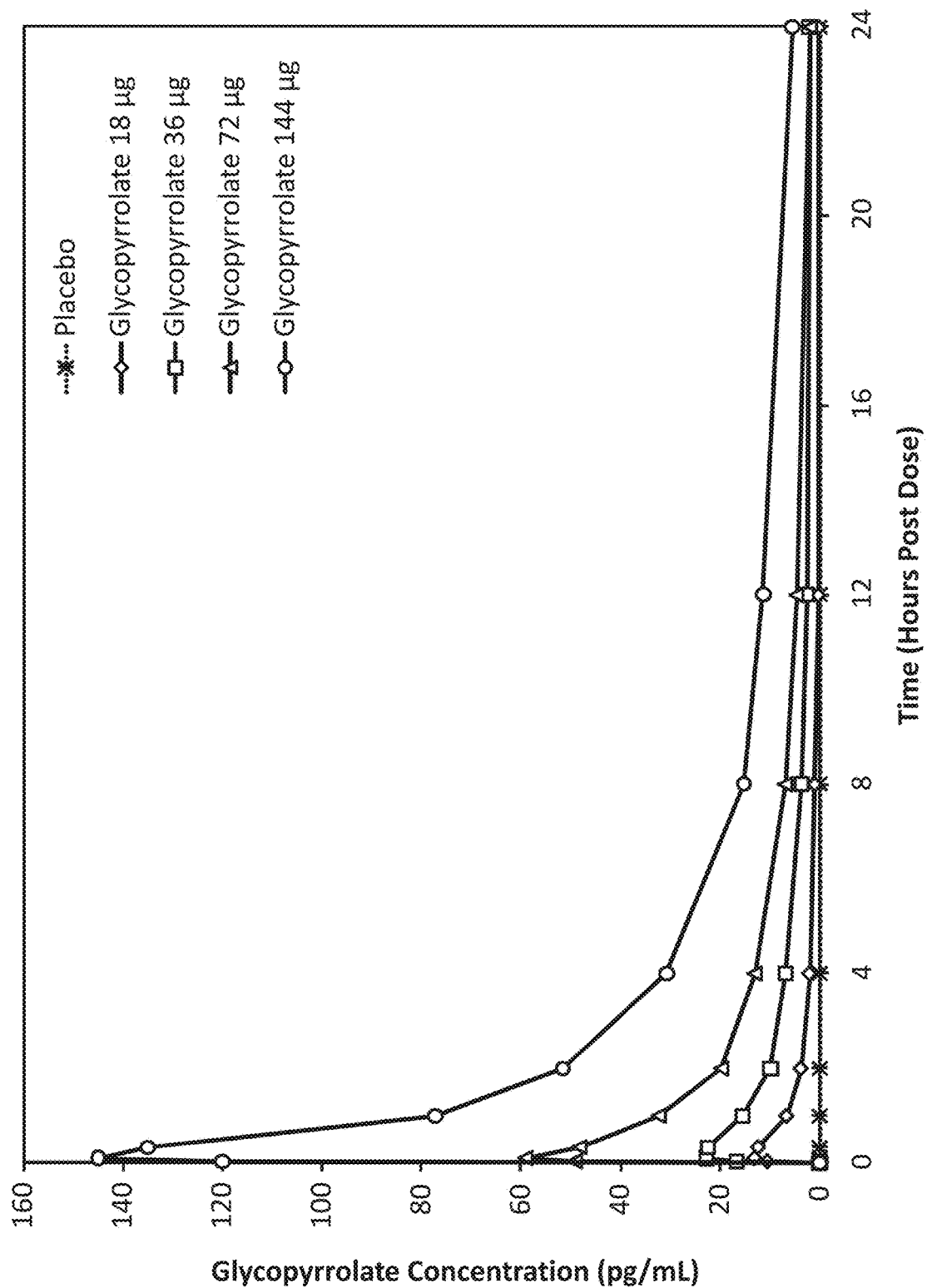
FIG. 5 is a graph, which depicts the serum glycopyrrolate concentration level achieved over a period of 24 hours after a single administration of four different doses of glycopyrrolate delivered from a co-suspension composition as described herein.

All doses of Glycopyrrolate MDI were safe and well tolerated, and the mean plasma glycopyrrolate concentration-time profiles were well characterized with rapidly occurring peak plasma concentrations, generally within 20 minutes. Plasma glycopyrrolate increased with dose level. FIG. 5 shows the serum glycopyrrolate concentration (in µg/mL) compared to placebo over a 24 hour period experienced in the study subjects.

Glycopyrrolate MDI showed statistically significant and clinically relevant superior efficacy compared to Placebo MDI (p<0.001 for all four glycopyrrolate doses) with a clear dose response relationship. The efficacy of Glycopyrrolate MDI 144 µg and Glycopyrrolate 72 µg bracketed that of tiotropium 18 µg in terms of peak improvement in $FEV_1$ over time. For improvement in secondary $FEV_1$ endpoints relative to test day baseline, including trough $FEV_1$ at 12 hours, $FEV_1$ $AUC_{0-12}$, $FEV_1AUC_{0-24}$, $FEV_1$ $AUC_{12-24}$, and 12 and 24-hour trough $FEV_1$, all doses of Glycopyrrolate MDI demonstrated clinically relevant and statistical superiority compared to Placebo MDI (p≤0.049 for all four dose levels), with the exception of improvement in trough $FEV_1$ at 24 hours following administration of Glycopyrrolate MDI 36 µg (difference compared to placebo=0.073 L; p=0.059). Similar to the clear dose-response relationship observed for improvement in peak $FEV_1$, dose ordering across all four doses of Glycopyrrolate MDI evaluated was also observed for improvements in $FEV_1$ $AUC_{0-12}$, $FEV_1$ $AUC_{0-24}$, and $FEV_1AUC_{12-24}$.

The Glycopyrrolate MDI 144 µg and 72 µg doses were shown to be statistically non-inferior to tiotropium 18 µg in terms of peak change in $FEV_1$, $FEV_1$ $AUC_{0-12}$, and $FEV_1$ $AUC_{0-24}$, with the a priori defined non-inferiority bound of 100 mL. The Glycopyrrolate 144 µg dose was also non-inferior to tiotropium for 12-hour trough and $FEV_1$ $AUC_{12-24}$. Point-estimates for the majority of the $FEV_1$ parameters for the 72 and 144 µg doses were within ±50 mL compared to tiotropium. In general, the secondary endpoints (time to onset of effect, peak and trough $FEV_1$, FVC, PEFR, and peak IC) confirmed the findings of the primary endpoint. Glycopyrrolate MDI demonstrated a more rapid onset of action compared to tiotropium 18 µg, with mean time to ≥10% improvement in $FEV_1$ of 1 hour or less for all doses of Glycopyrrolate MDI evaluated, compared to approximately 3 hours for tiotropium 18 µg.

Figure 6:
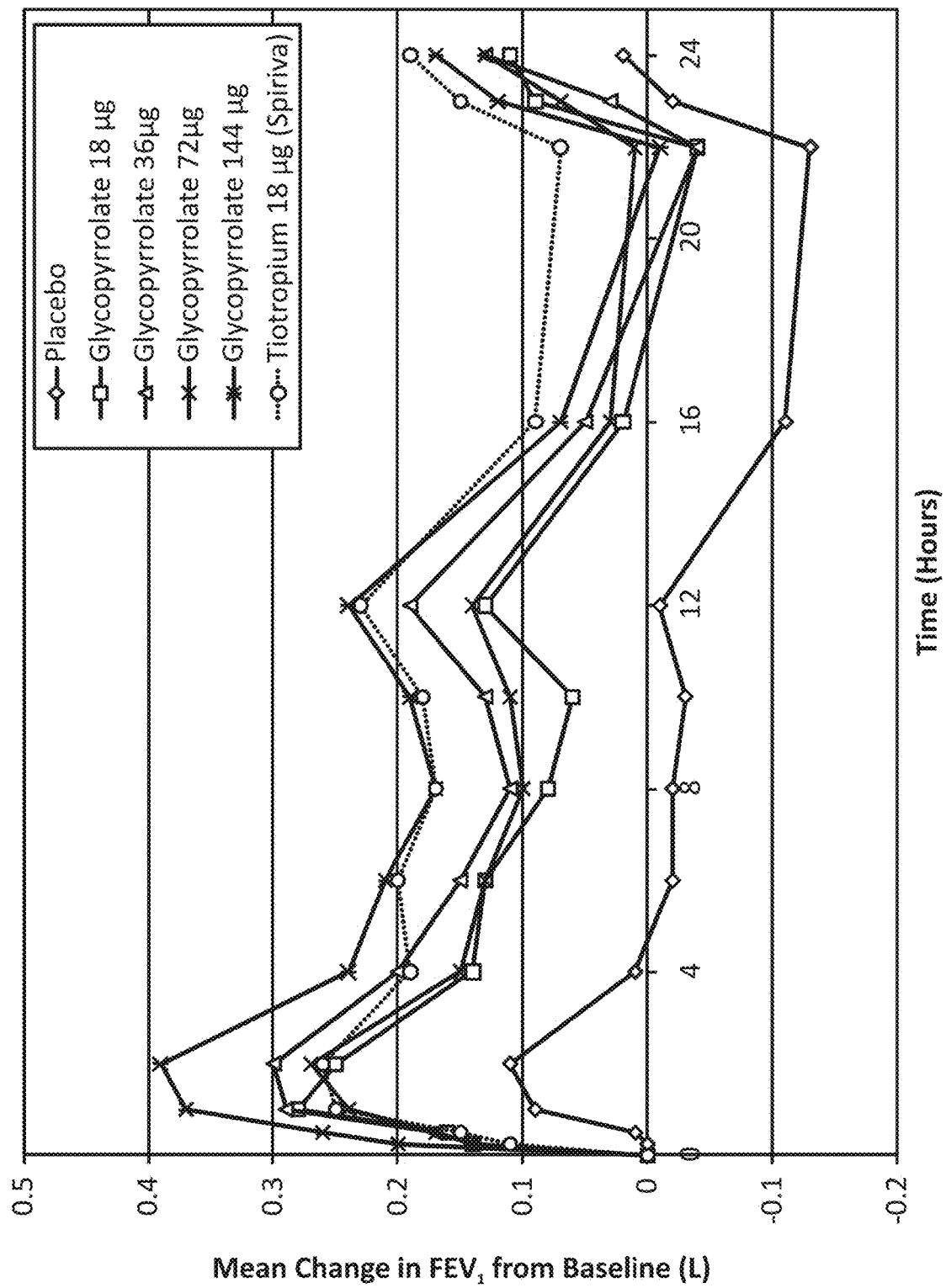
FIG. 6 is a graph, which depicts the mean change in $FEV_1$ from baseline (in liters) experienced in patients over a period of 24 hours after receiving a single administration of the indicated dose of glycopyrrolate formulated in a co-suspension as described herein. In this study, Spiriva (18 µg Tiotropium) was included as an active control, and the mean change in $FEV_1$ from baseline (in liters) experienced in patients receiving a single administration of Spiriva is also depicted.
Figure 7:
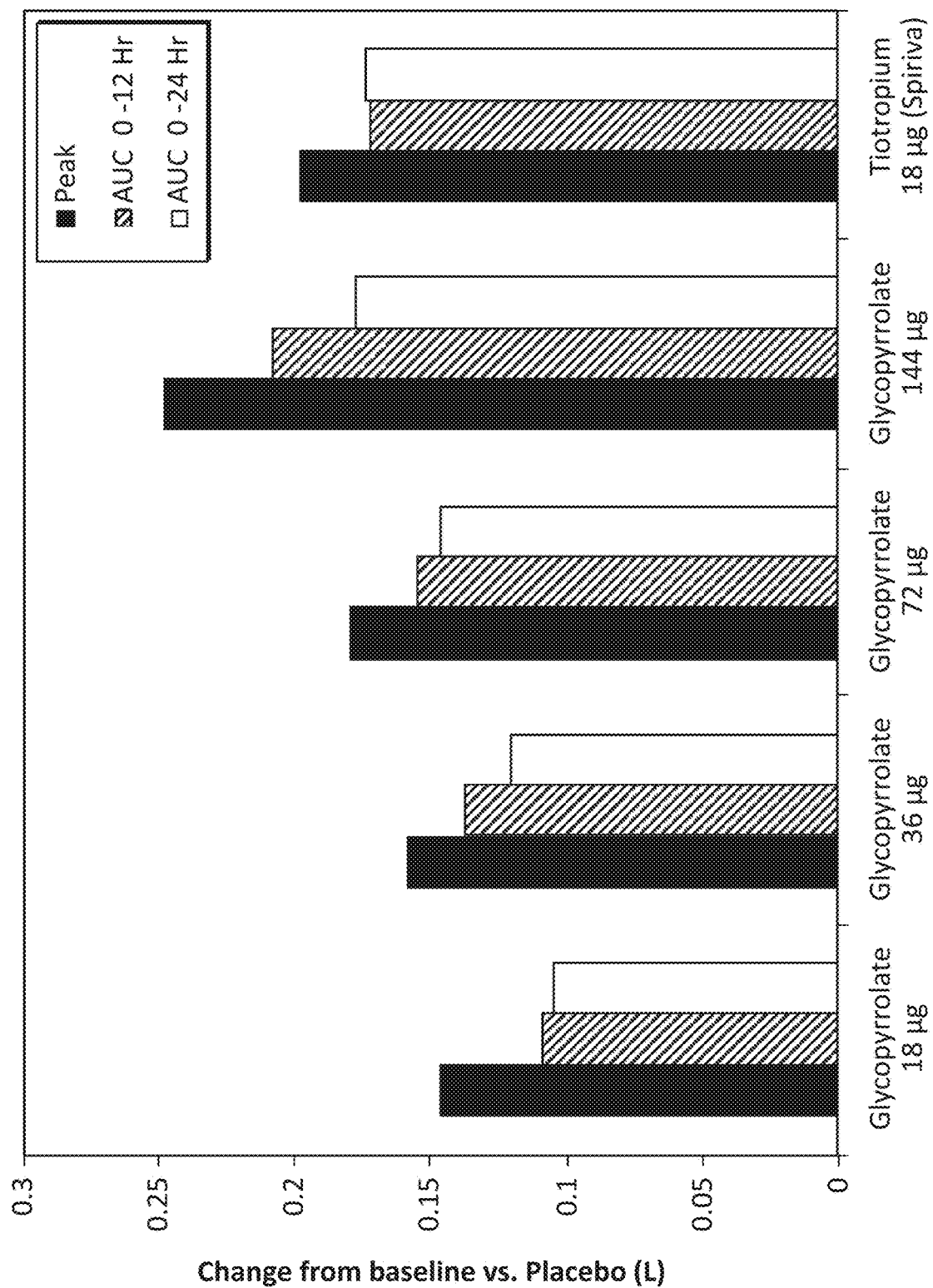
FIG. 7 is a bar graph, which depicts the peak change in $FEV_1$ from baseline (in liters) experienced in patients after receiving a single administration of the indicated dose of glycopyrrolate formulated in a co-suspension as described herein relative to placebo, the area under the curve of the $FEV_1$ over 12 hours after dosing, and the area under the curve of the $FEV_1$ over 24 hours after dosing relative to placebo across the four doses evaluated. In this study, Spiriva (18 μg Tiotropium) was included as an active control and the results following single administration of Spiriva for the above parameters are also depicted in this figure.
Figure 8:
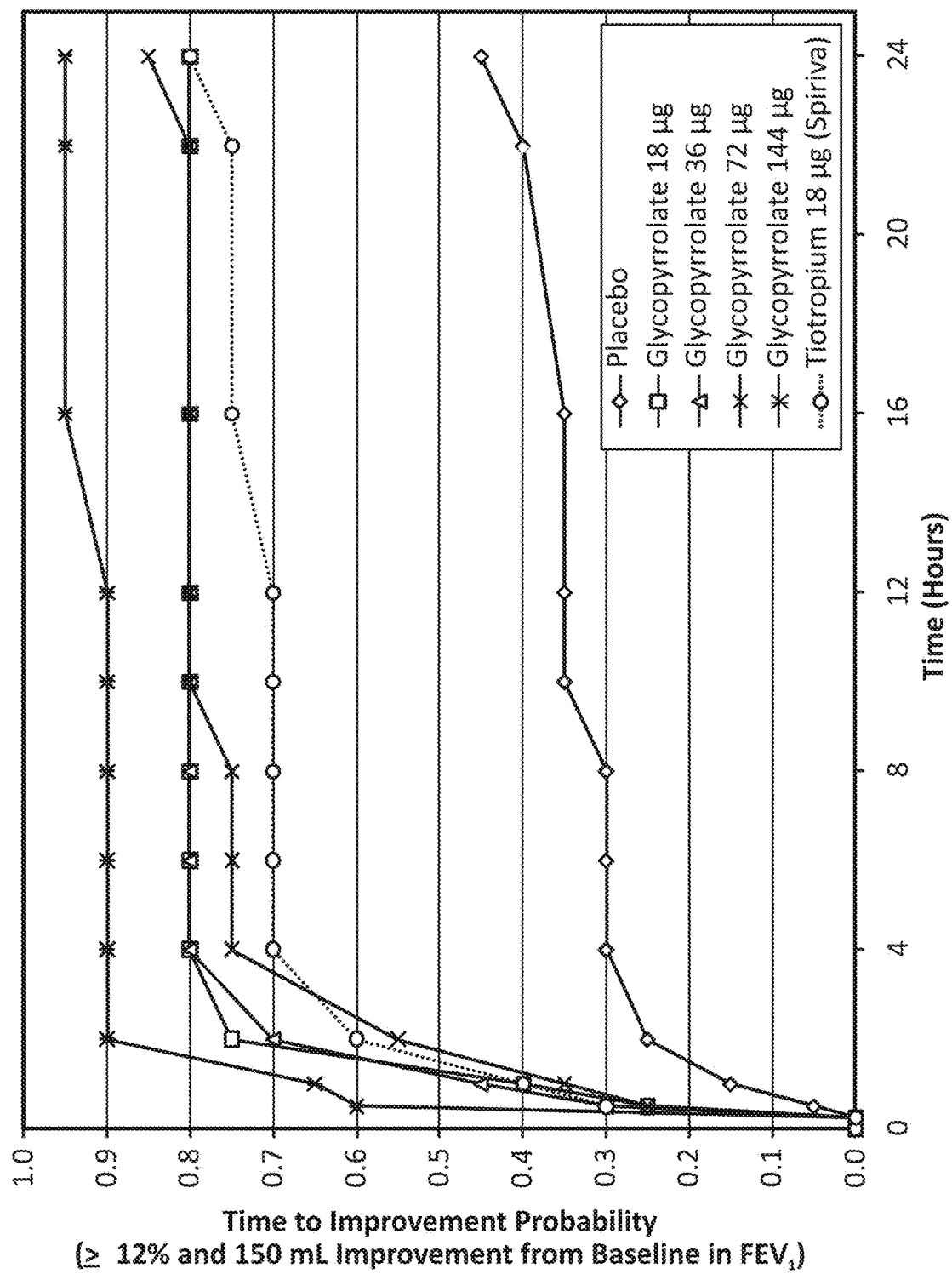
FIG. 8 is a graph, which depicts the proportion of patients which achieved a greater than 12% change in $FEV_1$ from baseline and an improvement of 150 mL change from baseline or an absolute improvement of 200 mL from baseline regardless of % change in $FEV_1$ from baseline, after receiving a single administration of the indicated doses of a glycopyrrolate co-suspension as described herein. In this study, Spiriva (18 μg Tiotropium) was included as an active control and the results following single administration of Spiriva for the above parameter are also depicted on this figure.
Figure 9:
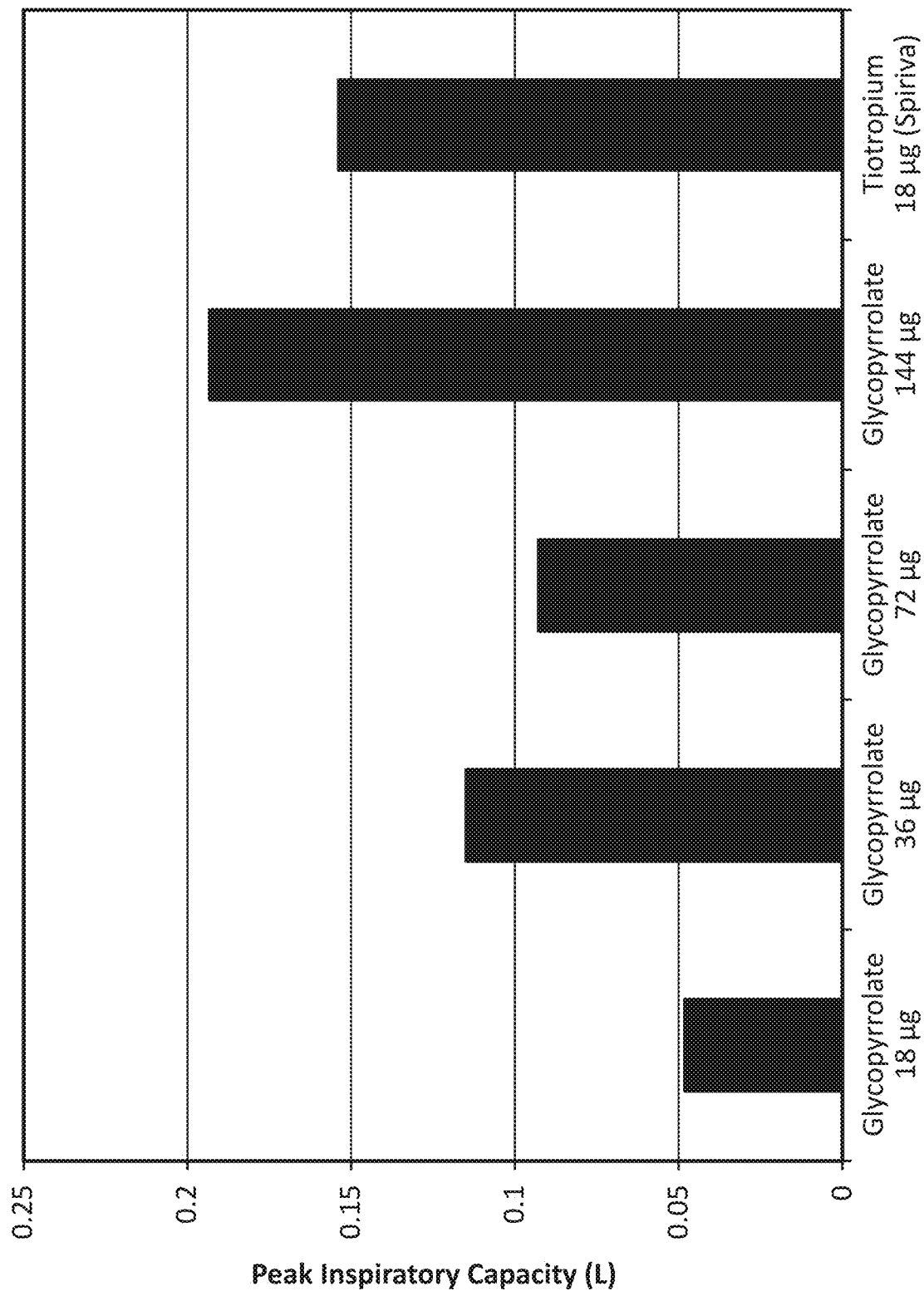
FIG. 9 is a bar graph, which depicts the peak change in inspiratory capacity experienced in patients after receiving a single administration of the indicated doses of a glycopyrrolate co-suspension as described herein. In this study, Spiriva (18 μg Tiotropium) was included as an active control and the results following single administration of Spiriva for the above parameter are also depicted on this figure.
Figure 10:
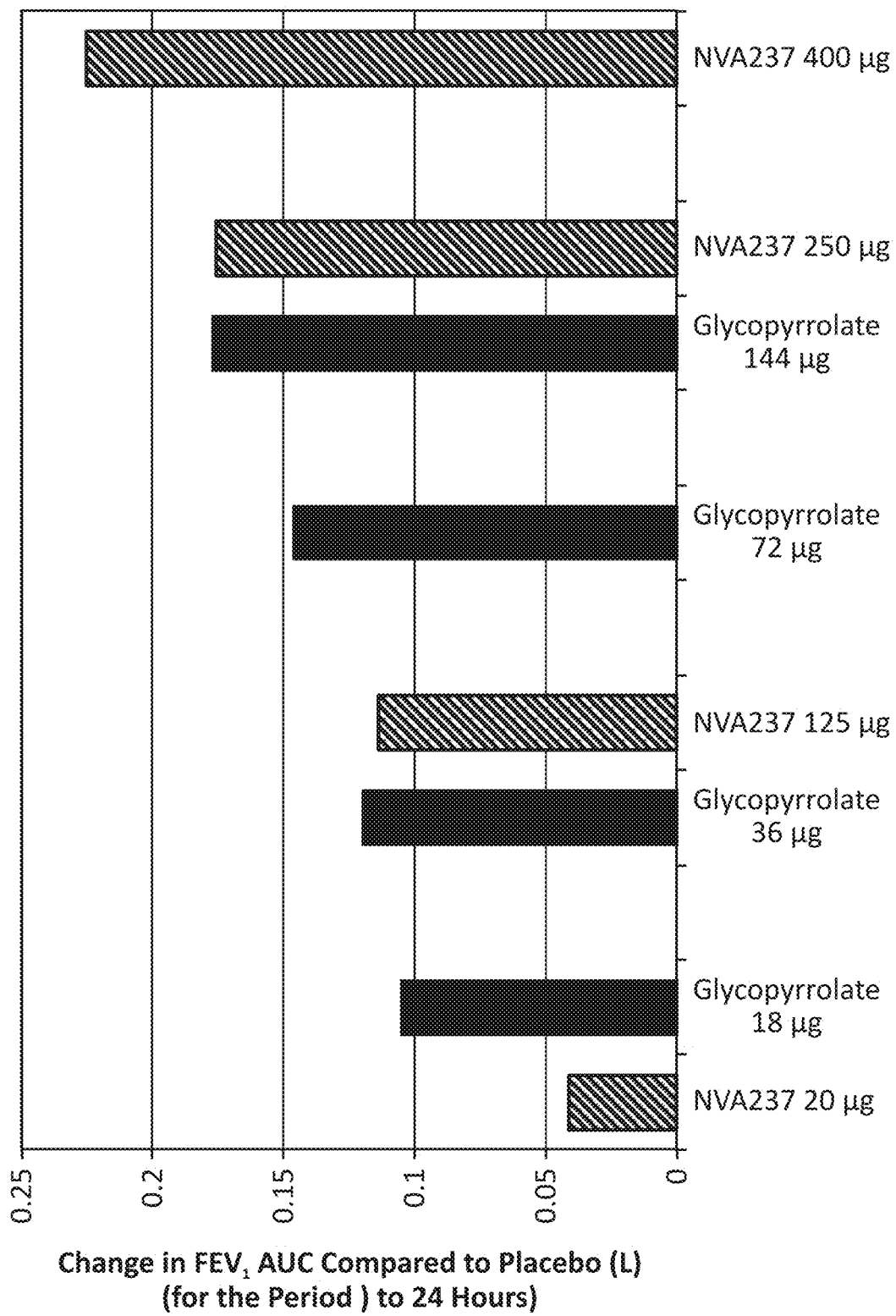
FIG. 10 is a bar graph providing the change in $FEV_1$ AUC achieved in patients after receiving a single administration of the indicated doses of a glycopyrrolate co-suspension as described herein. The results achieved by the glycopyrrolate co-suspension according to the present description are shown in comparison with the change in $FEV_1$ AUC reported in a published study in patients who received a powder formulation of glycopyrrolate not prepared according to the teachings provided herein.

FIG. 6 plots the mean change in $FEV_1$ from baseline (in liters) experienced by the study subjects over a period of 24 hours. FIG. 7 depicts the change in $FEV_1$ from baseline (in liters) for patients at different glycopyrrolate dosing levels compared to the results obtained for tiotropium. Specifically, FIG. 7 compares the peak change from baseline over the placebo value for different glycopyrrolate concentrations and the area under the curve over a 12 hour and 24 hour period. FIG. 8 depicts the proportion of patients which experienced either 1) an increase from baseline in $FEV_1$ of at least 200 mL or 2) a 12%, or greater, increase from baseline in $FEV_1$ coupled with total increase in $FEV_1$ of at least 150 mL or greater. FIG. 9 shows the peak improvement in IC experienced by patients administered the various doses of Glycopyrrolate, as well as the peak improvement in IC for patients receiving tiotropium. FIG. 10 shows change in $FEV_1$ cumulatively over a 24 hour period in patients receiving glycopyrrolate, compared with the results obtained from another clinical study where NVA237 (a powder formulation of glycopyrrolate) was given at various doses by Singh et al (D Singh, P A Corris, and S D Snape. "NVA237, a once-daily inhaled antimuscarinic, provides 24-hour bronchodilator efficacy in patients with moderate to-severe COPD" Poster presented at the American Thoracic Society International Conference, San Diego, Calif., May 19-24, 2006).

Example 7

Glycopyrrolate (GP) was micronized using a jet mill to a volume median optical diameter ($d_{50}$) of 1.4 µm with 90% of the cumulative distribution ($d_{90}$) having a volume optical diameter below 3.0 µm. Suspending particles were manufactured similarly to those in Example 1. MDI canisters were manufactured using FEP coated Presspart cans to provide products with metered dose of 5.5 µg/actuation GP and 44 µg/actuation GP which correlates to approximately 4.5 µg/actuation and 36 µg/actuation GP delivered dose from a 50 µl volume metering chamber from commercially available Bespak valves. The formulations contained 6 mg/mL of suspending particles. The MDI canisters were manufactured using standard pressure filling process where drug substance and the suspending were mixed with HFA 134a in a suspension vessel and filled into canisters through a commercially available filling head.

Figure 11:
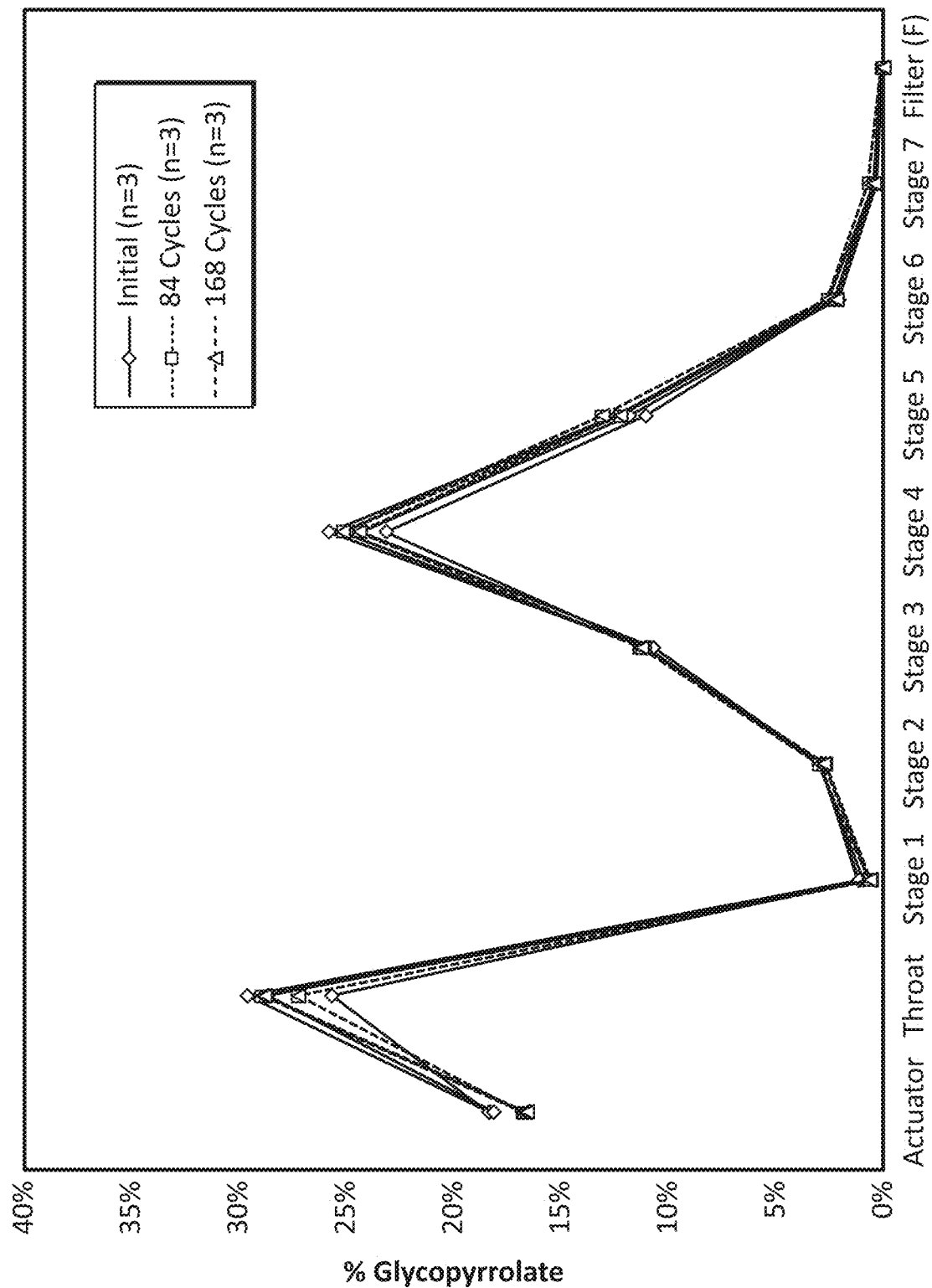
FIG. 11 is a graph, which depicts the particle size distribution of an exemplary glycopyrrolate co-suspension prepared according to the present description, containing 4.5 μg/actuation delivered dose of glycopyrrolate and 6 mg/mL suspending particles and subjected to temperature cycling conditions (alternating 6 h hold time at −5 or 40° C.).
Figure 12:
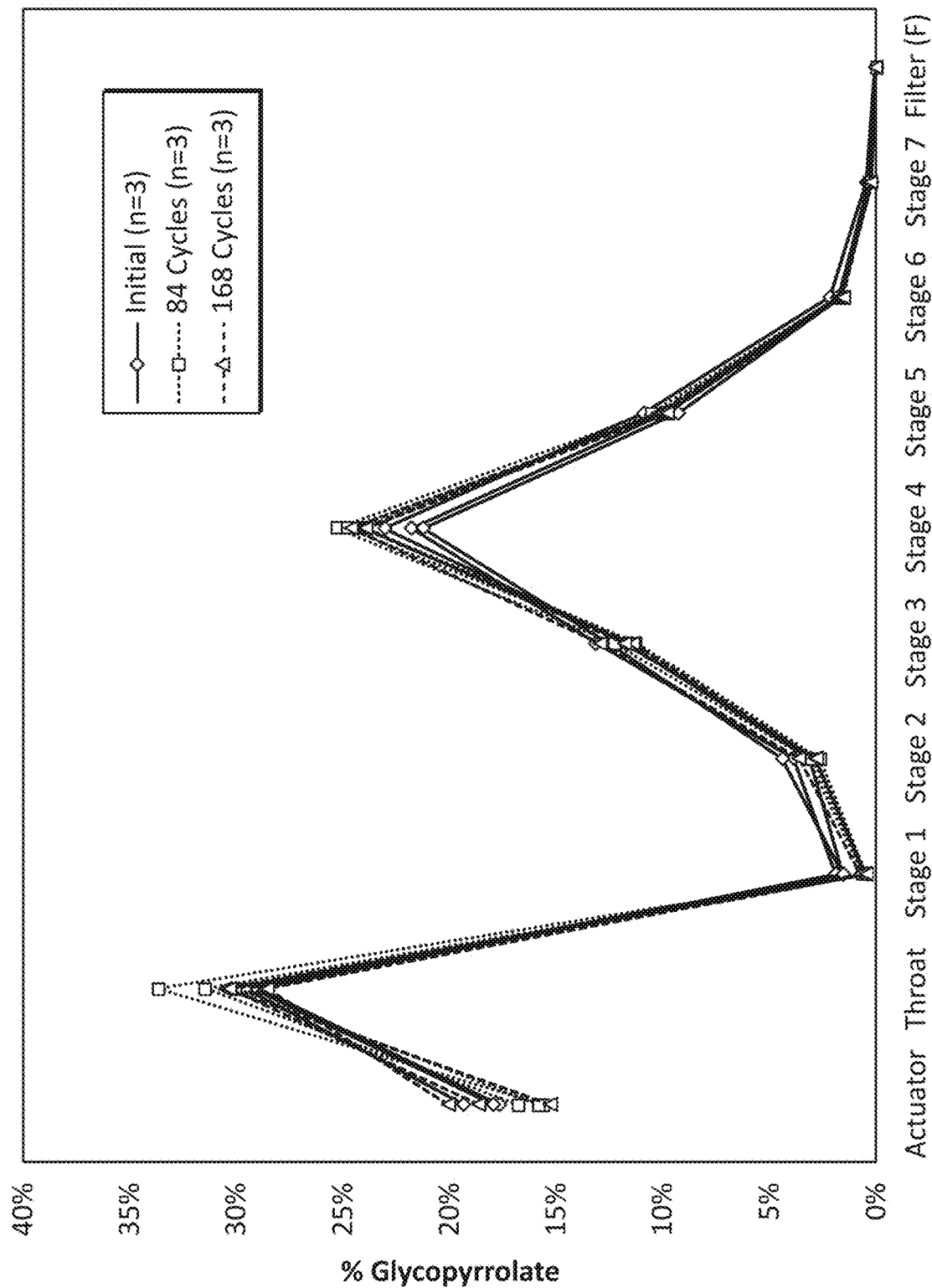
FIG. 12 is a graph, which depicts the particle size distribution of an exemplary glycopyrrolate co-suspension prepared according to the present description, containing 36 μg/actuation delivered dose of glycopyrrolate and 6 mg/mL suspending particles and subjected to temperature cycling conditions (alternating 6 h hold time at −5 or 40° C.).
Figure 13:
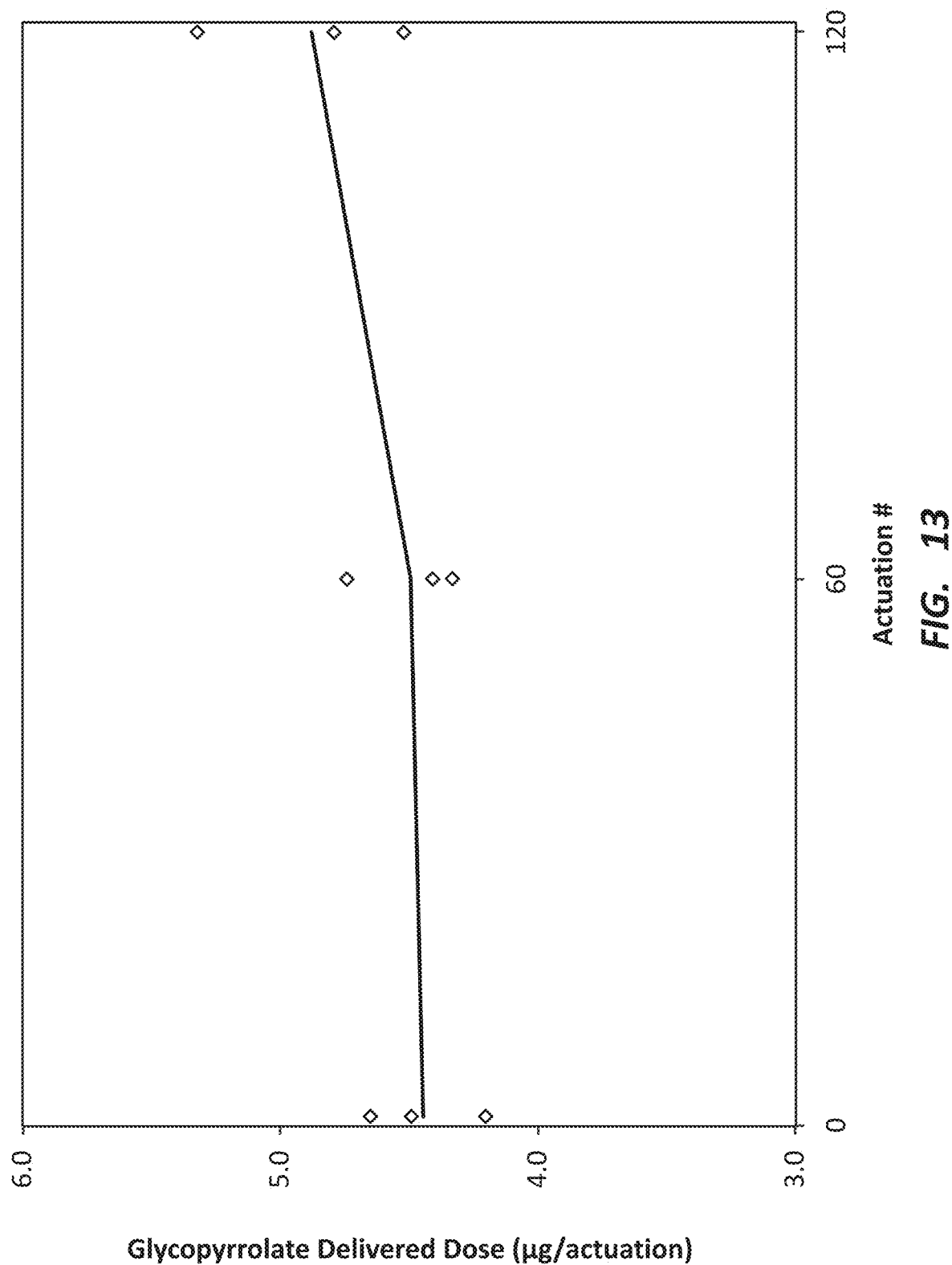
FIG. 13 is a graph, which depicts the delivered dose through canister life of an exemplary glycopyrrolate co-suspension prepared according to the present description, containing 4.5 μg/actuation delivered dose of glycopyrrolate and 6 mg/mL suspending particles.
Figure 14:
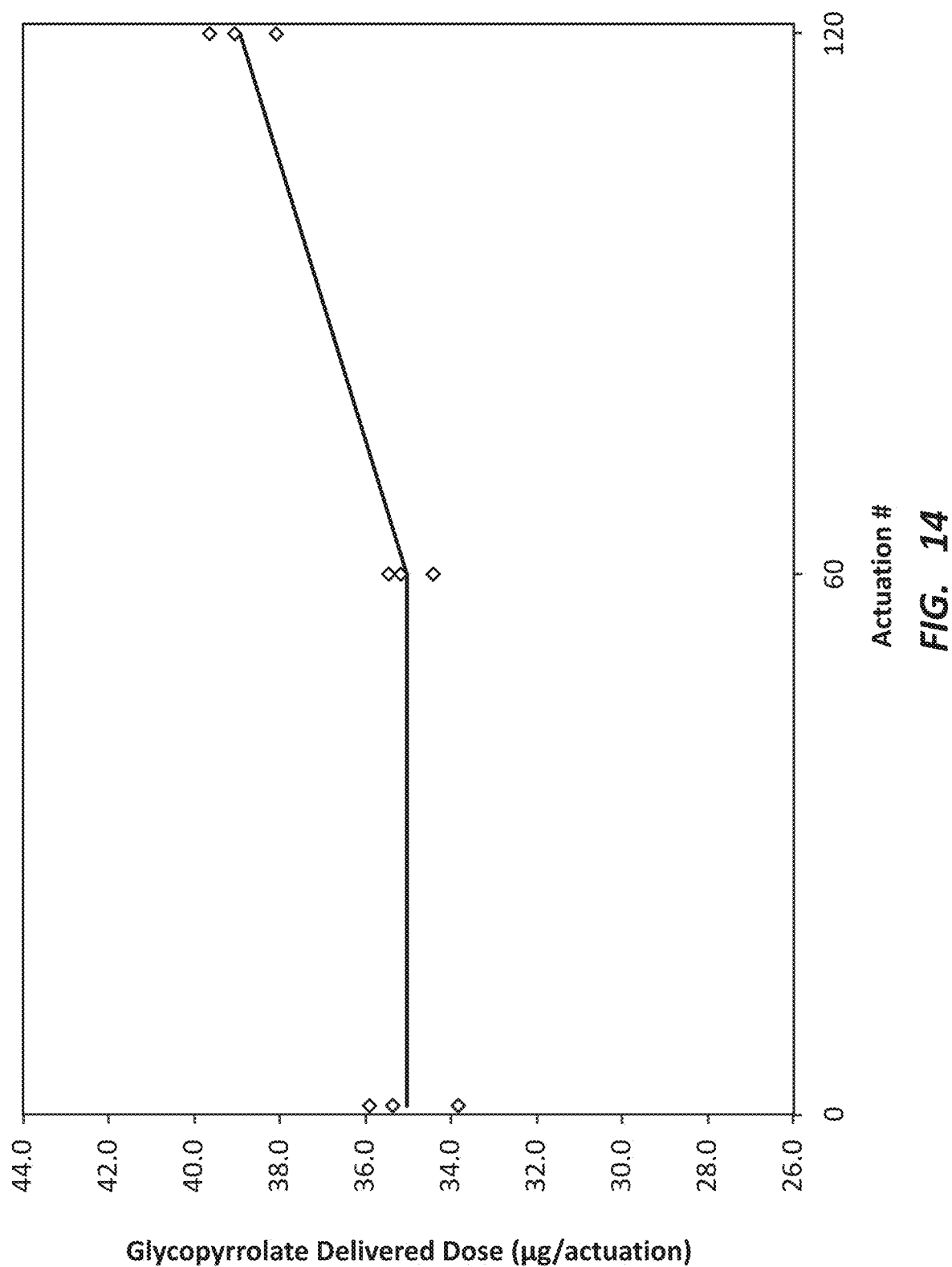
FIG. 14 is a graph, which depicts the delivered dose through canister life of an exemplary glycopyrrolate co-suspension prepared according to the present description, containing 36 μg/actuation delivered dose of glycopyrrolate and 6 mg/mL suspending particles.

Each lot was tested for delivered dose uniformity through can life and aerodynamic particle size distribution by Next Generation Impactor after manufacture. The aerodynamic particle size distributions as measured by the NGI are shown in FIGS. 11 and 12. Also shown are the amounts of drug recovered from valve stem and actuator, and from the induction port (throat) and its mouth piece adaptor. Recovered masses are expressed as percent of nominal dose. The fine particle fraction remained unchanged over 168 cycles, illustrating the stability of the GP co-suspensions disclosed herein across a GP dose range. The delivered dose through life of the MDI canisters is shown in FIGS. 13 and 14. No change in delivered dose from beginning to middle of can is observed and a ~10% increase from middle to end of canister. The change from middle to end is anticipated based upon evaporative losses of propellant as the can is emptied. The compositions described in this example demonstrate desirable delivered dose uniformity for MDI for doses as low as 4.5 µg/actuation.

In addition, canisters from each lot were subjected to a temperature cycling stability study. The canisters were subjected to −5° C. and 40° C. alternating between temperatures every 6 hours for a total duration of 84 cycles (3 weeks) and 168 cycles (6 weeks). After 184 cycles, the % FPF (ex-actuator) is not significantly different from initial. A summary of the stability of the fine particle fraction is shown in Table 6.

TABLE 6

Temperature Cycling Stability of the Fine Particle Fraction of crystalline GP co suspended with suspending particles at two doses in MDI containing HFA 134a

| Timepoint | 4.5 µg/actuation (% FPF ex-actuator) | 36 µg/actuation (% FPF ex-actuator) |
|---|---|---|
| Initial | 60.9 | 57.4 |
| 3 Weeks (84 cycles) | 61.9 | 58.0 |
| 6 Weeks (168 cycles) | 60.6 | 59.0 |

Example 8

Figure 15:
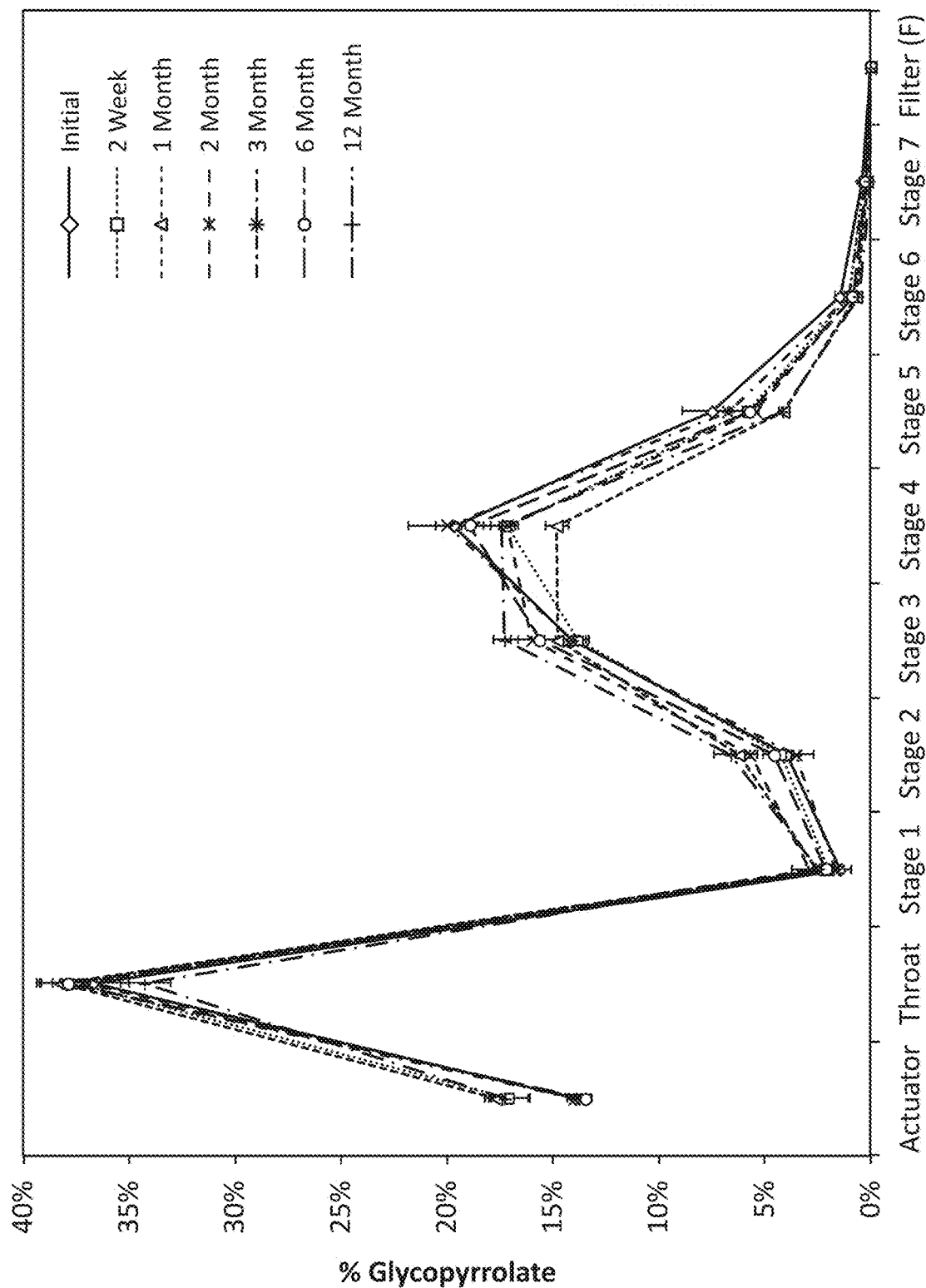
FIG. 15 is a graph, which depicts the particle size distribution of an exemplary glycopyrrolate co-suspension prepared according to the present description, containing 36 μg/actuation delivered dose of glycopyrrolate and 6 mg/mL suspending particles and subjected to 12 months storage at 25° C./60% RH unprotected.

MDI Canisters were manufactured to contain 6 mg/mL suspending particle concentration and to provide a metered dose of 36 μg/actuation with a 50 μl valve volume according to Example 7. Micronized GP had a $d_{50}$ and $d_{90}$ of 1.6 μm and 4.1 μm respectively and suspending particles were manufactured similarly to the process described in Example 1. The canisters were placed on stability without protective packaging at 25° C./60% RH and stored for duration of 12 months. Aerodynamic particle size distribution was determined by next generation impaction at 2 weeks, 1, 2, 3, 6 or 12 months. The fine particle fraction, as a percentage of GP ex-actuator, at initial sampling was 50.2%. No significant change in the fine particle fraction was noted at any of the timepoints out to 12 months, with FPF of 47.7% after 12 months. FIG. 15 provides a view of the entire aerodynamic size distribution for each of the timepoints demonstrating desirable consistency on aerosol delivery. A summary of the fine particle fraction is shown in Table 7.

TABLE 7

Stability of the Fine Particle Fraction of crystalline GP co suspended with suspending particles in MDI containing HFA 134a at 25° C. and 60% RH with no protective packaging

| Time-Point | % FPF (ex actuator) |
| --- | --- |
| Initial | 50.2 |
| 2 Week | 46.1 |
| 1 Month | 42.0 |
| 2 Month | 46.0 |
| 3 Month | 48.9 |
| 6 Month | 47.7 |
| 12 Month | 47.7 |

Example 9

Figure 16:
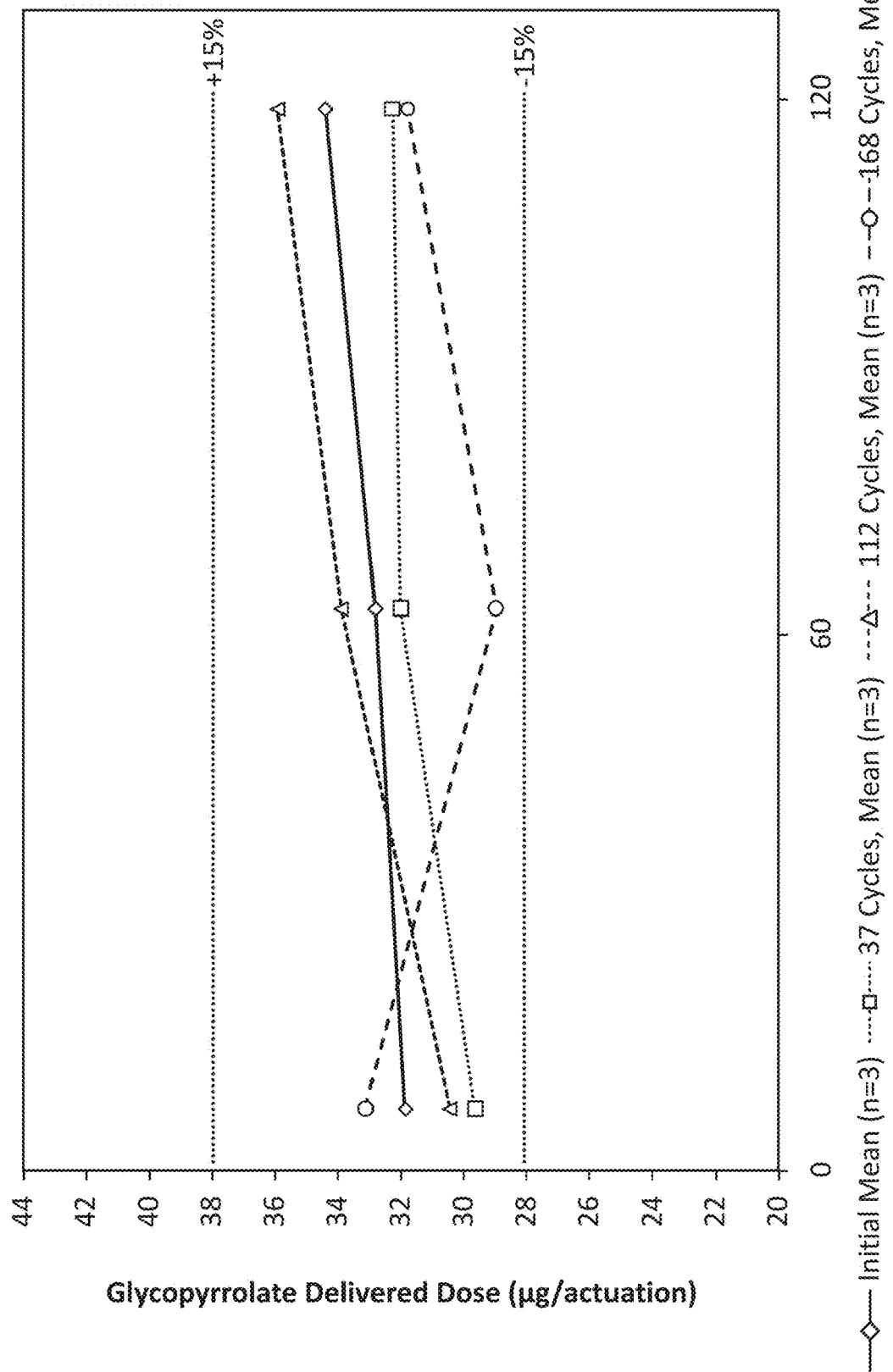
FIG. 16 is a graph, which depicts the mean delivered dose through canister life of an exemplary glycopyrrolate co-suspension prepared according to the present description, containing 32 μg/actuation delivered dose of glycopyrrolate and 6 mg/mL suspending particles and subjected to temperature cycling conditions (alternating 6 h hold time at −5 or 40° C.).
Figure 17:
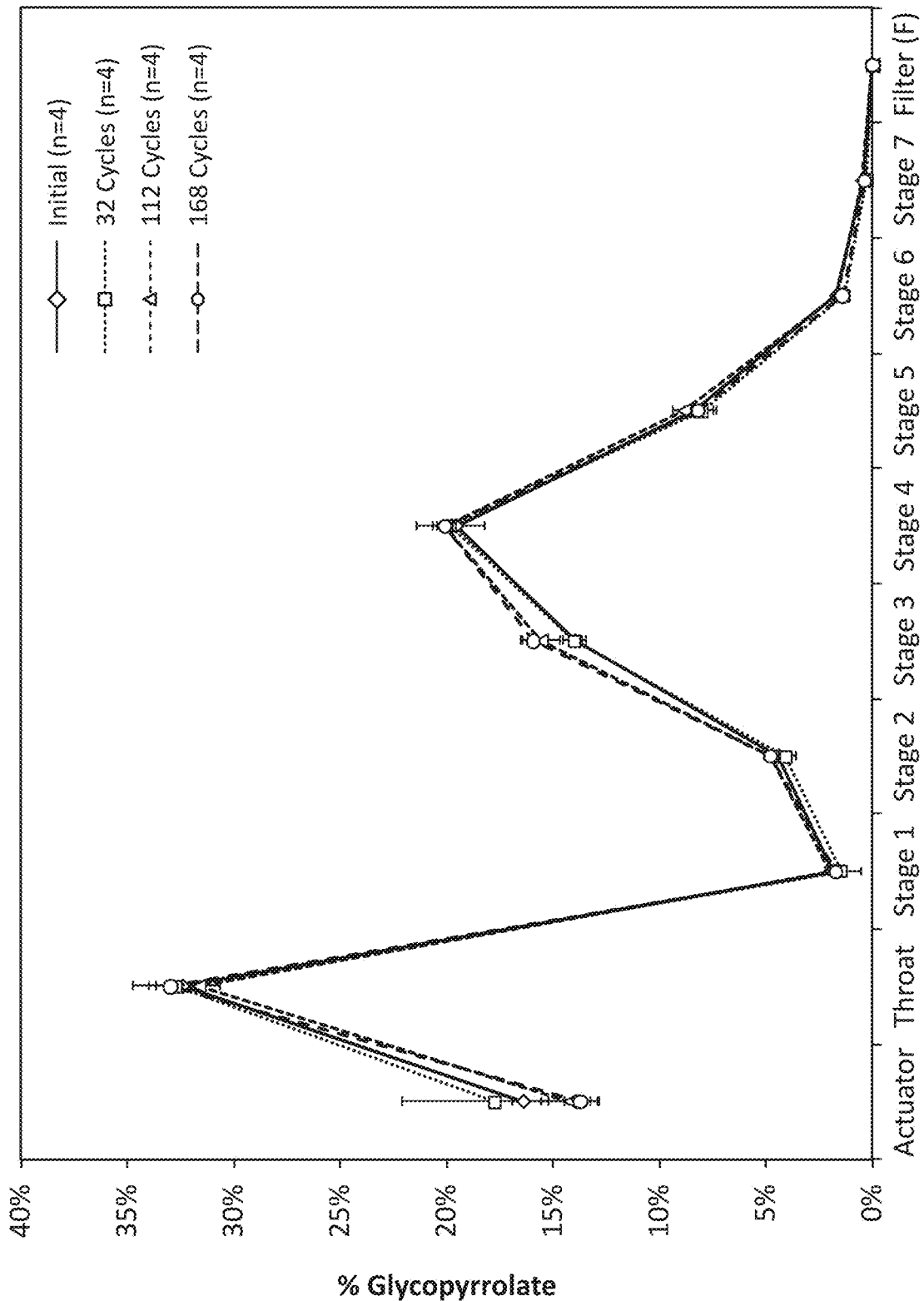
FIG. 17 is a graph, which depicts the particle size distribution of an exemplary glycopyrrolate co-suspension prepared according to the present description, containing 32 μg/actuation delivered dose of glycopyrrolate and 6 mg/mL suspending particles and subjected to temperature cycling conditions (alternating 6 h hold time at −5 or 40° C.)

MDI Canisters were manufactured to contain 6 mg/mL suspending particle concentration and to provide a metered dose of 36 μg/actuation as described in Example 7. These canisters were packaged in a heat sealed aluminum foil overwrap containing desiccant, and cycled for 6 weeks (6 hours at −5° C. and 6 hours at 40° C.). The delivered dose uniformity through use was tested at the 0, 2, 4 and 6 weeks time points. The mean glycopyrrolate delivered dose of each lot each time period was within ±15% of the mean, with one exception, as demonstrated in FIG. 16. The aerodynamic particle size distribution as measured by NGI remain unchanged after 168 temperature cycles as shown in FIG. 17.

Example 10

Figure 18:
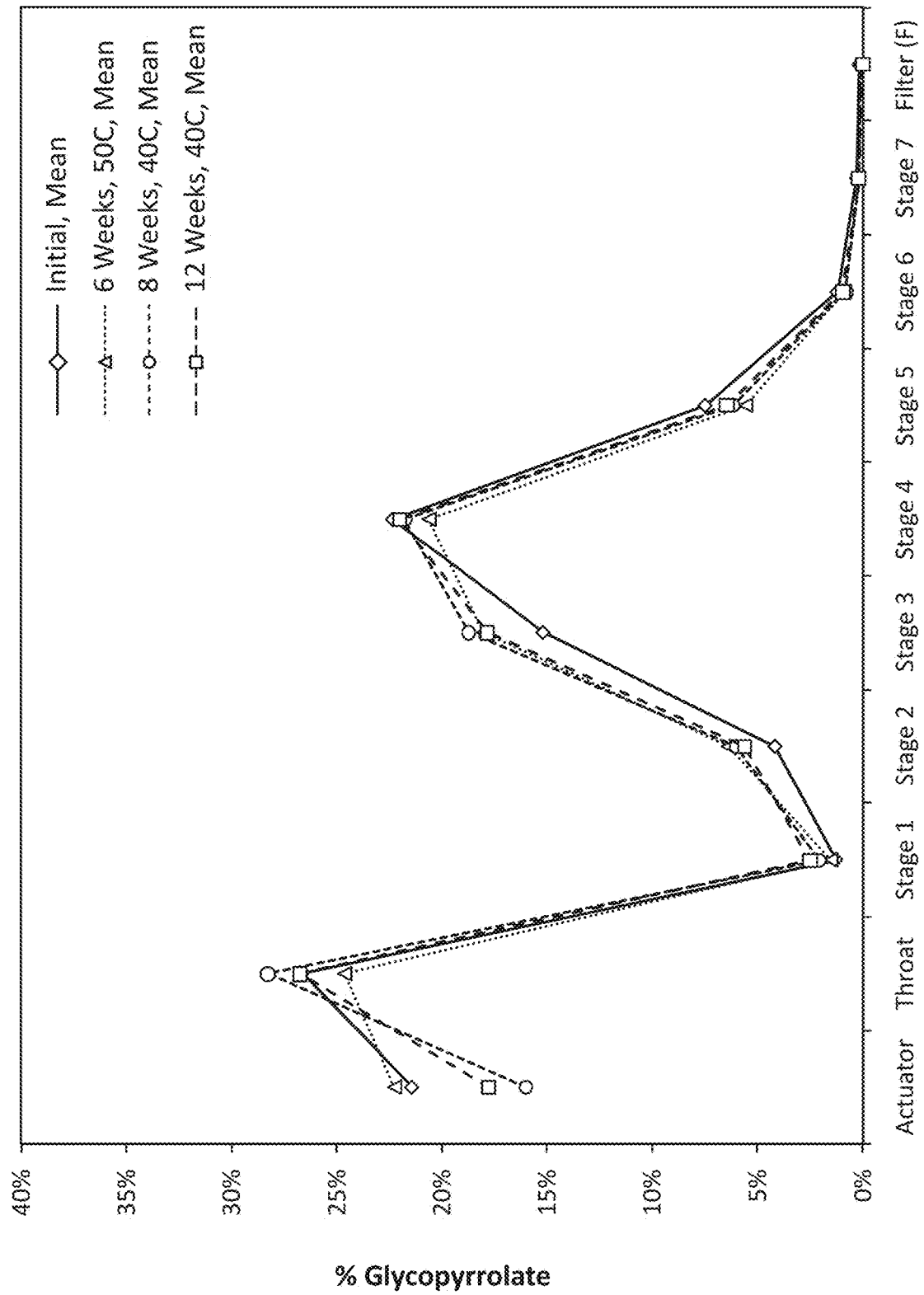
FIG. 18 is a graph, which depicts the particle size distribution of an exemplary glycopyrrolate co-suspension prepared according to the present description, containing 24 μg/actuation delivered dose of glycopyrrolate and 6 mg/mL suspending particles and subjected to 6 weeks storage at 50° C./ambient relative humidity and 12 weeks at 40° C.

MDI Canisters were manufactured to contain 6 mg/mL suspending particle concentration and to provide a metered dose of 24 μg per actuation according to Example 7. These canisters were stored for six weeks at 50° C. under ambient humidity. Another lot was stored for 8 weeks at 40° C. and 75% relative humidity. Yet another lot was stored for 12 weeks at 40° C. and 75% relative humidity. The fine particle fraction was 59.3% initially. The canister stored for 6 weeks at 50° C. had an FPF that was unchanged compared to the initial lot, i.e. at 58.4%. The lot stored at 40° C. for 8 and 12 weeks had an FPF that was also unchanged compared to the initial, i.e. at 56.8% and 57.6% respectively. The aerodynamic particle size distributions as measured by the NGI are shown in FIG. 18. The MMAD remains relatively unchanged after 6 weeks at 50° C., 3.94 μm, and up to 12 weeks at 40° C., 3.84 μm, compared to the initial at 3.54 μm. In addition, the FPF and the amounts of glycopyrrolate recovered from valve stem and actuator, and from the induction port (throat) and its mouth piece adaptor, remained relatively unchanged over 3 months at elevated temperatures.

Example 11

Metered dose inhalers including pharmaceutical compositions of formoterol fumarate as described herein were prepared. Formoterol fumarate, (±)-2-hydroxy-5-[(1RS)-1-hydroxy-2-[[(1RS)-2-(4-methoxyphenyl)-1-methylethyl]-amino]ethyl] formanilide fumarate, also known as (±)-2'-hydroxy-5'-[(RS)-1-hydroxy-2-[[(RS)-p-methoxy-α-methylphenethyl]-amine]ethyl] formanilide fumarate, dihydrate was micronized to form active agent particles. The particle size distribution of the micronized formoterol fumarate (FF) was determined by laser diffraction. 50% by volume of the micronized particles exhibited an optical diameter smaller than 1.6 μm, and 90% by volume exhibited an optical diameter smaller than 3.9 μm.

Suspending particles were manufactured as follows: 503 mL of a fluorocarbon-in-water emulsion of PFOB (perfluorooctyl bromide) stabilized by a phospholipid was prepared. 20.6 g of the phospholipid, DSPC (1,2-disteroyl-sn-glycero-3-phosphocholine), and 1.9 g of calcium chloride were homogenized in 403 mL of hot water (75° C.) using a high shear mixer. 100 mL of PFOB were added slowly during homogenization. The resulting coarse emulsion was then further homogenized using a high pressure homogenizer (Model C3, Avestin, Ottawa, Calif.) at pressures of up to 170 MPa for 5 passes.

The emulsion was spray dried in nitrogen using the following spray drying conditions: Inlet temperature 95° C., outlet temperature 71° C., emulsion feed rate 2.4 mL/min, total gas flow 498 L/min. The particle size distribution of the suspending particles was determined by laser diffraction. 50% by volume of the suspending particles were smaller than 3 μm, the geometric standard deviation of the distribution was 1.9.

Metered dose inhalers were prepared by weighing the target masses of micronized active agent particles and suspending particles into coated glass vials with 15 mL volume. The target masses and the target delivered dose assuming 20% actuator deposition are given in Table 8 for three different configurations. For each configuration, additional glass bottles were filled with the respective amount of FF active agent particles without any suspending particles. The canisters were crimp sealed with 63 μl valves (Valois, Les Vaudreuil, France) and filled with 11 g (9.1 mL at 25° C.) of HFA 134a (1,1,1,2-tetrafluoroethane) (Ineos Fluor, Lyndhurst, UK) by overpressure through the valve stem. After injecting the propellant, the canisters were sonicated for 15 seconds and agitated on a wrist action shaker for 30 minutes.

TABLE 8

Target doses for formoterol fumarate co-suspensions of Example 10

| Configuration # | FF Active Agent Particles μg/can | Suspending Particles mg/can | Target delivered dose μg | Suspending Particle to active particle ratio |
|---|---|---|---|---|
| 6A | 300 | 50 | 1.7 | 167 |
| 6B | 860 | | 4.6 | 58 |
| 6C | 3010 | | 16.5 | 16.6 |

Figure 19:
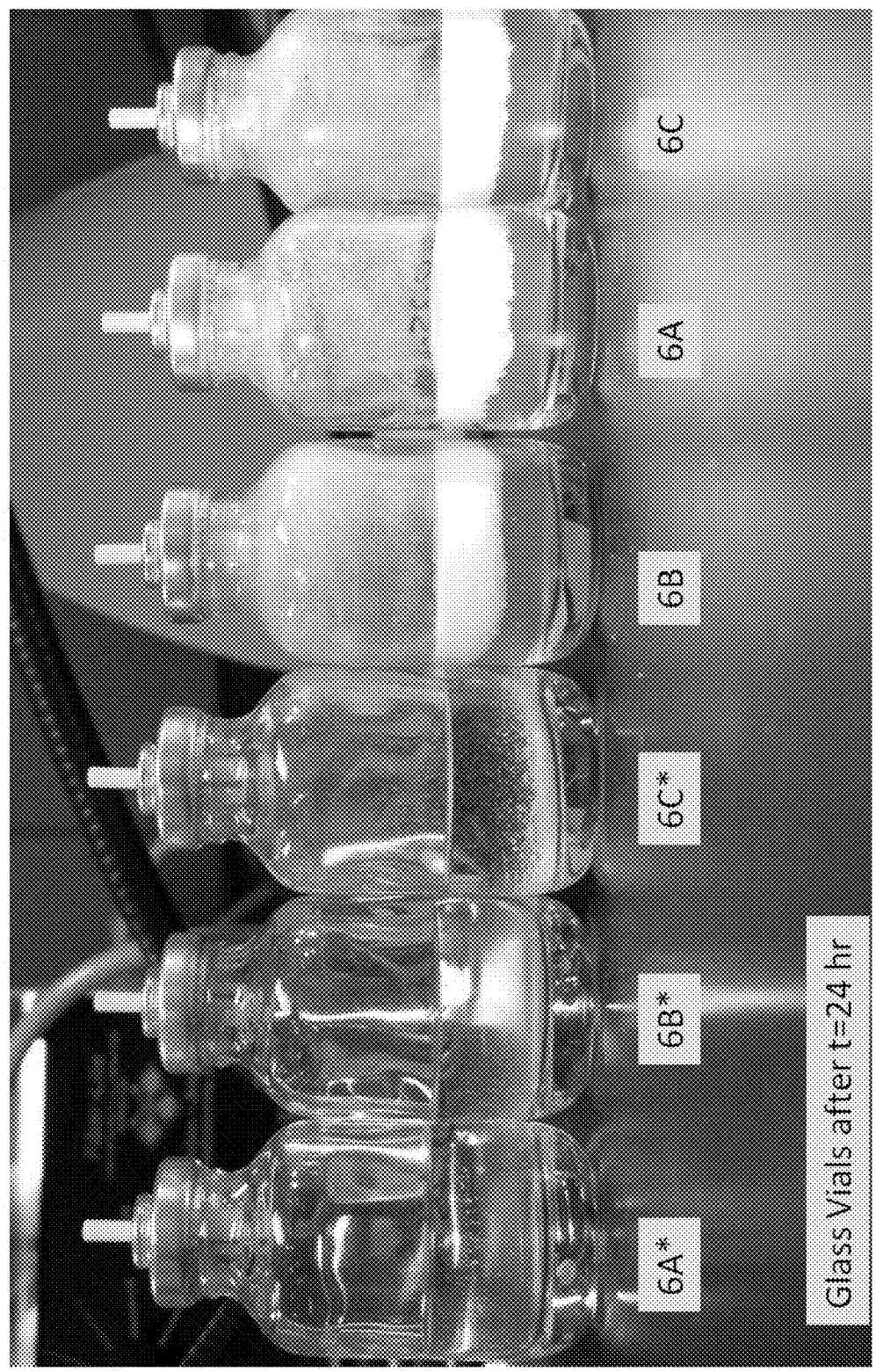
FIG. 19 is a photograph that allows visualization of co-suspension compositions prepared according to the present description which include formoterol fumarate active agent particles.
Figure 20:
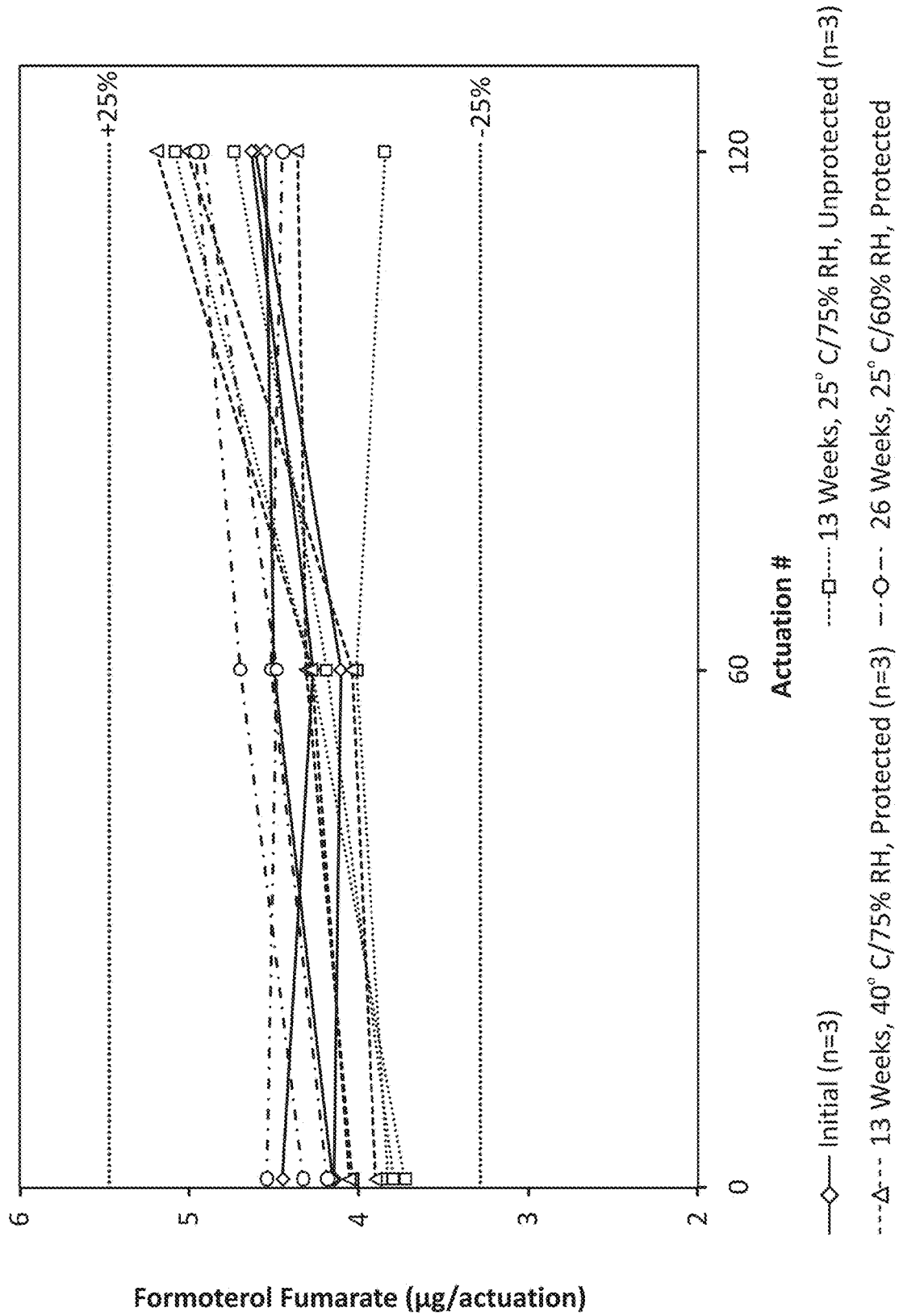
FIG. 20 is a graph, which depicts the delivered dose uniformity achieved by formoterol fumarate co-suspension compositions prepared according to the present description.
Figure 21:
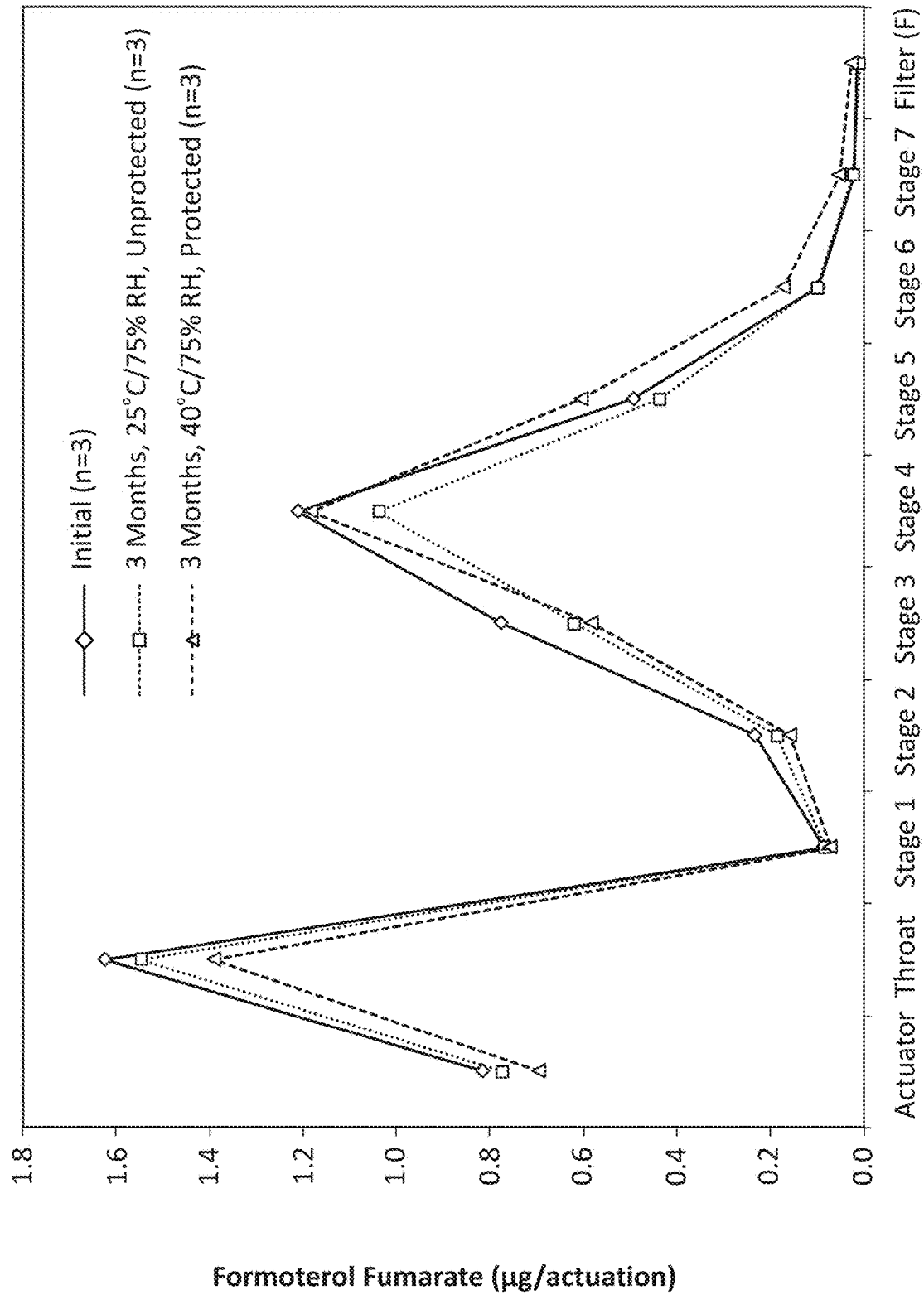
FIG. 21 is a graph, which depicts the aerodynamic particle size distribution determined by cascade impaction of exemplary formoterol fumarate co-suspension compositions prepared according to the present description and stored for three months at 25° C./75% RH, without protective overwrap, or at 40° C./75% RH with protective overwrap.

Visual observation of the co-suspended configurations (6A, 6B, 6C) showed no sedimentation of the crystalline FF forming the active agent particles. The suspension flocculated slowly and formed a homogeneous, single cream layer. For all concentrations tested the micronized active agent particles alone sedimented quickly. Pictures of the co-suspension and the traditional comparator suspensions, indicated by an asterisk, are shown in FIG. 19. The vials were left to settle for 24 h without agitation. No FF crystals were visible at the bottom of any of the co-suspension vials.

The results showed that the FF crystals associated with the suspending particles. The association between FF particles and suspending particles was strong enough to overcome buoyancy forces, as FF particles did not separate from the suspending particles and settling of the active agent particles was successfully inhibited in each of the three different formulation configurations.

Example 12

Formoterol fumarate MDI compositions were prepared according to the present invention. Micronized formoterol fumarate was commercially obtained and its particle size distribution measured as described in Example 1 was characterized by a $d_{10}$, $d_{50}$, $d_{90}$ of 0.6, 1.9 and 4.4 µm respectively and a Span of 2.0. Suspending particles used were prepared in a similar manner described in Example 1. MDI manufacturing was accomplished using a drug addition vessel (DVA) by first adding half of suspending particle quantity, next filling the microcrystalline FF, and lastly adding the remaining half of suspending particles to the top. Materials were added to the DAV in a humidity controlled environment of <10% RH. The DAV was then connected to a 4 L suspension vessel. A slurry was then formed by adding a known amount of HFA-134a propellant (Ineos Fluor, Lyndhurst, UK) into the DAV, which is then removed from the suspension vessel and gently swirled. The slurry is then transferred back to the suspension mixing vessel and diluted with additional HFA-134a to form the final suspension at target concentration stirring gently with an impeller. The temperature inside the vessel was maintained at 21-23° C. throughout the entire batch production. After recirculation of the batch for 30 min, 14-mL fluorinated ethylene polymer (FEP) coated aluminum canisters (Presspart, Blackburn, UK) were filled with the suspension mixture through 50 µL EPDM valves (Bespak, King's Lynn, UK). Sample canisters were then selected at random for total canister assay to ensure correct formulation quantities.

The freshly manufactured co-suspension MDI batch was then placed on one week quarantine before initial performance analysis. Aerosol performance was assessed in accordance with USP <601> (United States Pharmacopeia monograph 601). A Next Generation Impactor (NGI) operated at a flow rate of 30 L/min was used for determination of particle size distribution. Sample canisters were seated into an actuator with two waste actuations and two additional waste priming actuations. Five actuations were collected in the NGI with a USP throat attached. The valve, actuator, throat, NGI cups, stages, and filter were rinsed with volumetrically dispensed solvent. The sample solutions were assayed using a drug specific chromatographic method. The fine particle fraction was defined using the sum of stages 3 through filter. Delivered dose uniformity through use testing was performed using a Dose Uniformity Sampling Apparatus as described by USP <601>. Two actuations were collected and assayed at beginning, middle and end of use.

FIG. 20 shows the delivered dose uniformity for a co-suspension of FF at a 4.8 µg target dose per actuation. The individual delivered dose per actuation for beginning, middle and end of actuations was within ±25% of the mean delivered dose.

Example 13

Formoterol Fumarate MDI compositions were prepared according to the present invention. Micronized formoterol fumarate was commercially obtained and its particle size distribution measured as described in Example 1 was characterized by a $d_{10}$, $d_{50}$, $d_{90}$ of 0.6, 1.9 and 4.4 µm respectively and a Span of 2.0. Suspending particles used were prepared in a similar manner described in Example 1. MDI manufacturing was accomplished as described in Example 12.

Aerosol performance was assessed in accordance with USP <601>. A Next Generation Impactor (NGI) operated at a flow rate of 30 L/min was used for determination of particle size distribution. Sample canisters were seated into an actuator with two waste actuations and two additional waste priming actuations. Five actuations were collected in the NGI with a USP throat attached. The valve, actuator, throat, NGI cups, stages, and filter were rinsed with volumetrically dispensed solvent. The sample solutions were assayed using a drug specific chromatographic method. The fine particle fraction was defined using the sum of stages 3 through filter. The aerodynamic particle size distribution of a FF co-suspension formulation was evaluated after manufacture and after three months of storage at 25° C. and 75% RH (unprotected canisters) and 40° C. and 75% RH (protected canisters wrapped in aluminum foil pouch). The aerodynamic particle size distributions shown in FIG. 21 demonstrate that the compositions described in the present invention display desirable stability characteristics even at accelerated conditions.

Example 14

The chemical stability of formoterol fumarate (FF) included in a co-suspension formulation prepared according Example 11 was evaluated. FF MDI canisters containing HFA 134a were overwrapped with an aluminum foil pouch and stored at 25° C. and 60% relative humidity and 40° C. and 75% relative humidity for thirteen and six months, respectively. Likewise FF MDI canisters containing HFA

Figure 22:
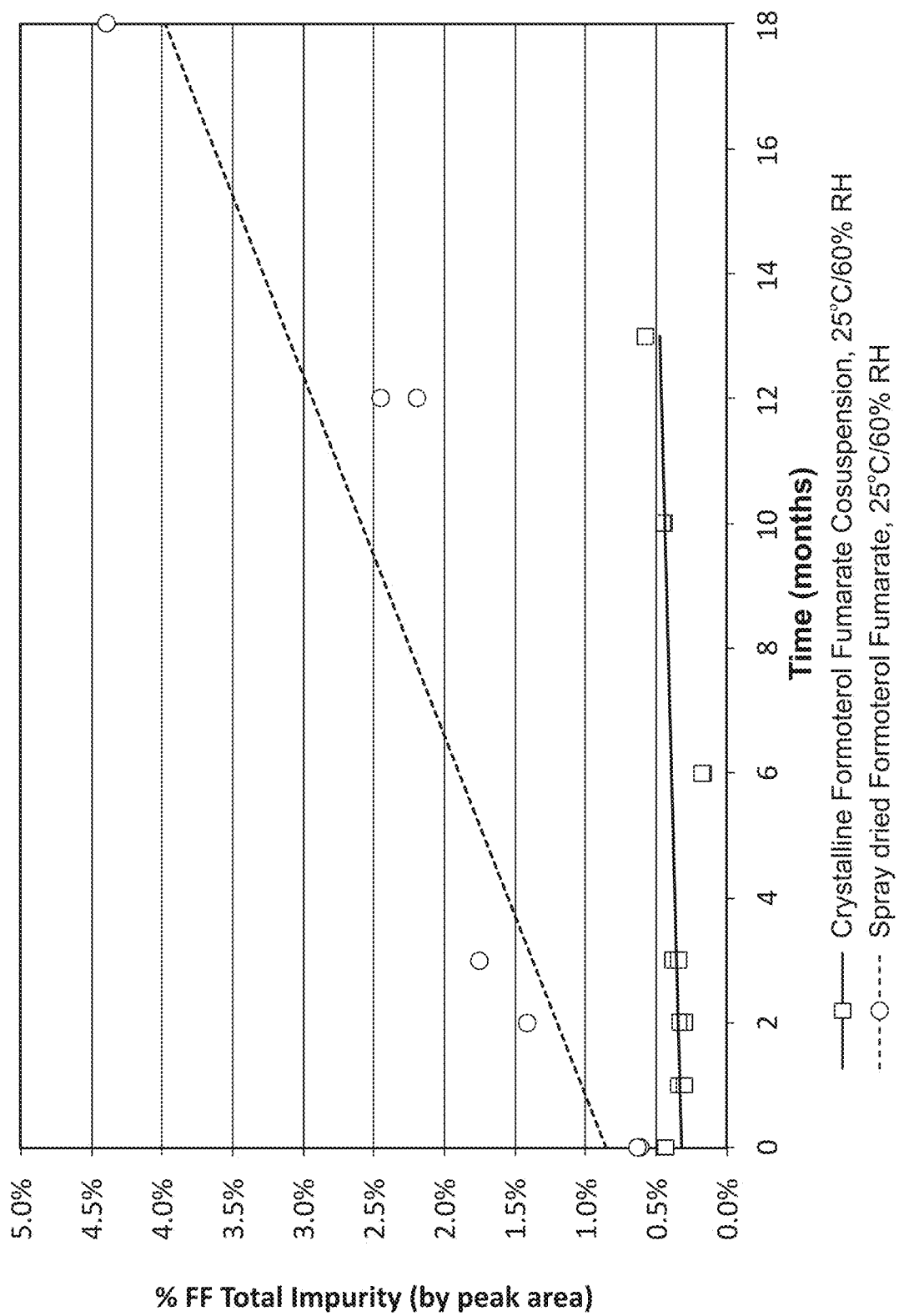
FIG. 22 is a graph, which depicts the chemical stability of exemplary co-suspension compositions including formoterol fumarate as the active agent. The results depicted in this figure allow comparison of the chemical stability of formoterol fumarate achieved in a co-suspension composition formulated using crystalline formoterol fumarate with the chemical stability of suspension formulations prepared using spray dried formoterol fumarate.

227ea were overwrapped with an aluminum foil pouch and stored at 25° C. and 60% relative humidity and 40° C. and 75% relative humidity for six months. The amount of impurity F, a characteristic degradation product of FF, and total impurities were determined by reverse phase HPLC assay as follows: each canister is chilled, cut open, and the can contents are transferred to a centrifuge tube; the contents were dissolved in organic solvent, followed by the addition of an aqueous solvent to precipitate excipient (DSPC) from the solution; the solution was centrifuged to produce a clear supernatant solution; and each sample solution was analyzed using a C18 column, 4.6×150 mm and 3.0 µm particle size. The column temperature was kept at 30° C. The injection volume was 20 µl, and flow rate was set at 1 mL/min and detected by determining the UV absorption at 214 nm. A gradient was used mixing pH 3.1 aqueous phosphate buffer and acetonitrile, 17% acetonitrile first 27 minutes, then 50% acetonitrile for 30 seconds followed by 6.5 minutes at 75% acetonitrile and 17% acetonitrile for 8 minutes. Impurities were reported as area percent of formoterol peak area (corrected for relative response factors, where available). As shown in FIG. 22 (or Table 9 and 10), a co-suspension prepared using crystalline FF active agent particles suspended in HFA 134a with suspending particles was chemically stable for 18 months at a temperature of 25° C. and 60% relative humidity, in contrast a spray dried, non co-suspended formoterol formulation showed a faster degradation rate under the same storage conditions. Likewise crystalline FF active agent particles formed a chemically stable co-suspension in HFA 227a, as shown in Table 11.

TABLE 9

Chemical Stability of Spray Dried FF Suspending Particles in FF MDI Containing HFA 134a at 25° C./60% RH, Overwrapped in Aluminum Foil Pouches

| | Time (months) | | | | |
|---|---|---|---|---|---|
| | 0 | 2 | 3 | 12 | 18 |
| Impurity F (%) | ND | 0.12% | 0.04% | 1.16% | 2.77% |
| Total Impurities (%) | 0.62% | 1.42% | 1.75% | 2.33% | 4.39% |

ND = Not detected

TABLE 10

Chemical Stability of Crystalline FF Co-suspended with Suspending Particles in FF MDI Containing HFA 134a at 25° C./60% RH, Overwrapped in Aluminum Foil Pouches

| | Time (months) | | | | | | |
|---|---|---|---|---|---|---|---|
| | 0 | 1 | 2 | 3 | 6 | 10 | 13 |
| Impurity F (%) | 0.05% | 0.08% | 0.08% | 0.14% | 0.06% | 0.22% | 0.35% |
| Total Impurities (%) | 0.44% | 0.32% | 0.32% | 0.37% | 0.18% | 0.45% | 0.64% | at 40° C./75% RH, Overwrapped in Aluminum Foil Pouches

| | Time (months) | | | | |
|---|---|---|---|---|---|
| | 0 | 1 | 2 | 3 | 6 |
| Impurity F (%) | 0.05% | 0.11% | 0.31% | 1.18% | 1.74% |
| Total Impurities (%) | 0.44% | 0.41% | 0.75% | 1.58% | 2.54% |

TABLE 11

Chemical Stability of Crystalline FF Co-suspended with Suspending Particles in FF MDI Containing HFA 227ea at 25° C./60% RH, Overwrapped in Aluminum Foil Pouches

| | Time (months) | | | | |
|---|---|---|---|---|---|
| | 0 | 1 | 2 | 3 | 6 |
| Impurity F (%) | 0.04 | 0.06 | 0.07 | 0.13 | 0.05 |
| Total Impurities (%) | 0.4 | 0.3 | 0.3 | 0.4 | 0.1 | at 40° C./75% RH, Overwrapped in aluminum foil pouches

| Impurity F (%) | 0.04 | 0.08 | 0.18 | 0.80 | 1.14 |
| Total Impurities (%) | 0.40 | 0.39 | 0.53 | 1.13 | 1.56 |

Example 15

Micronized formoterol fumarate dihydrate (FF) (Inke, S.A., Barcelona, Spain) used in the present example had with particle size distribution by laser diffraction of 50% by volume of the micronized particles exhibited an optical diameter smaller than 1.9 µm, 90% by volume exhibited an optical diameter smaller than 4.1 µm. Four batches of suspending particles were manufactured by spray drying as described in Example 1. All four batches were spray-dried from aqueous solution; solution concentration and spray drying parameters are given in Table 12.

TABLE 12

Suspending particle configurations used in Example 15

| | | | Spray Drying Parameters | | | | | |
|---|---|---|---|---|---|---|---|---|
| | | $C_f$ | Feed rate | | | Total Gas | Particle Size Distribution | |
| # | Powder Composition | in mg/mL | in mL/min | $T_{in}$ in ° C. | $T_{out}$ in ° C. | Flow in std L/min | VMD in µm | GSD |
| XA | 100% trehalose | 80 | 10 | 150 | 82 | 385 | 1.62 | 2.20 |
| XB | 100% HP-β-cyclodextrin | 80 | 10 | 100 | 68 | 885 | 1.61 | 2.21 |
| XC | 100% Ficoll PM 70 | 80 | 10 | 100 | 70 | 885 | 1.19 | 2.27 |
| XD | 100% Inulin | 80 | 10 | 100 | 70 | 885 | 1.23 | 2.20 |

Figure 23:
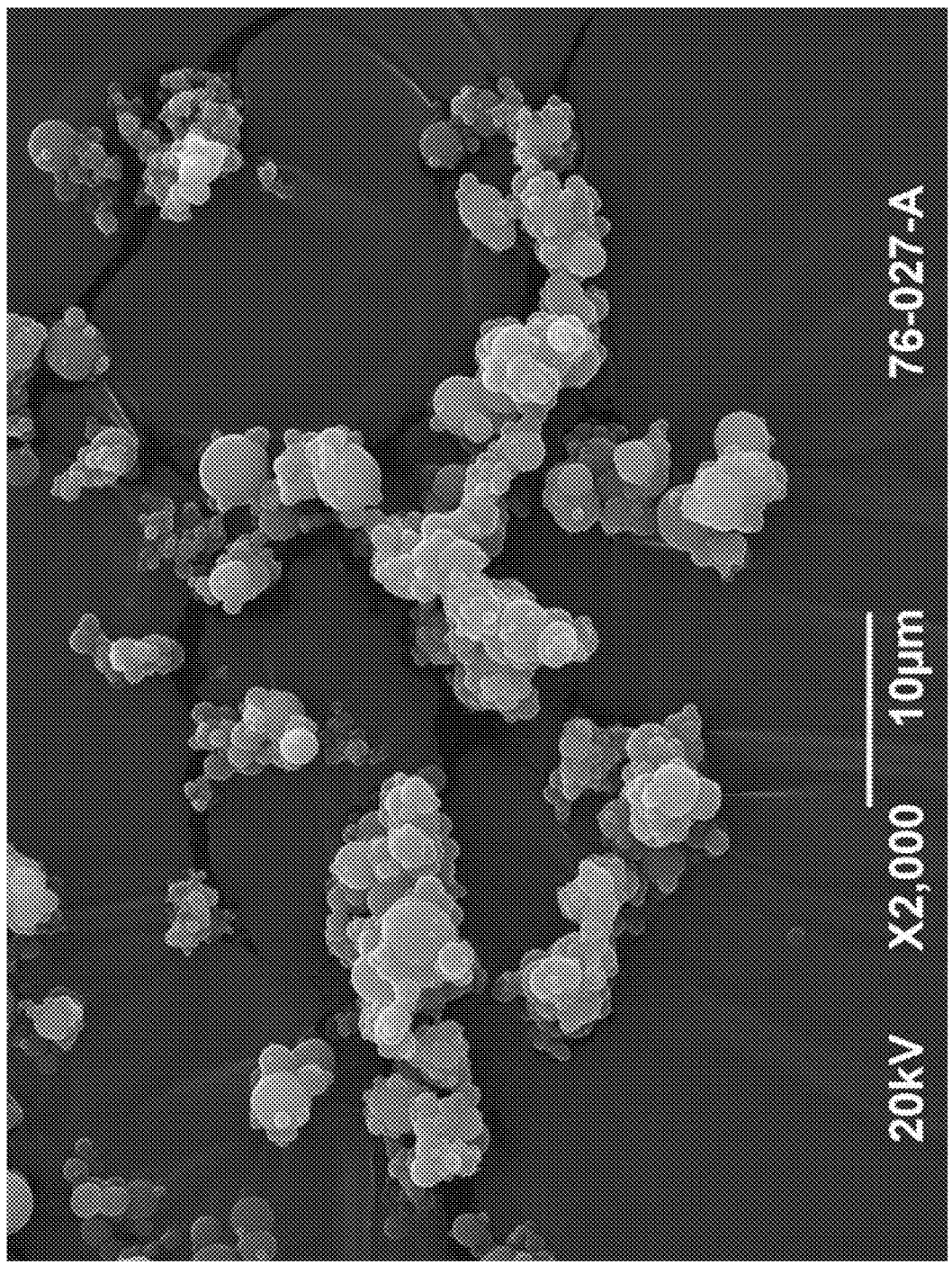
FIG. 23 through FIG. 26 are electron micrographs of suspending particles prepared from various different materials, with FIG. 23 providing a micrograph of trehalose suspending particles, FIG. 24 providing a micrograph of HP-β-cyclodextrin suspending particles, FIG. 25 providing a micrograph of Ficoll MP 70 suspending particles, and FIG. 26 providing a micrograph of inulin suspending particles.
Figure 24:
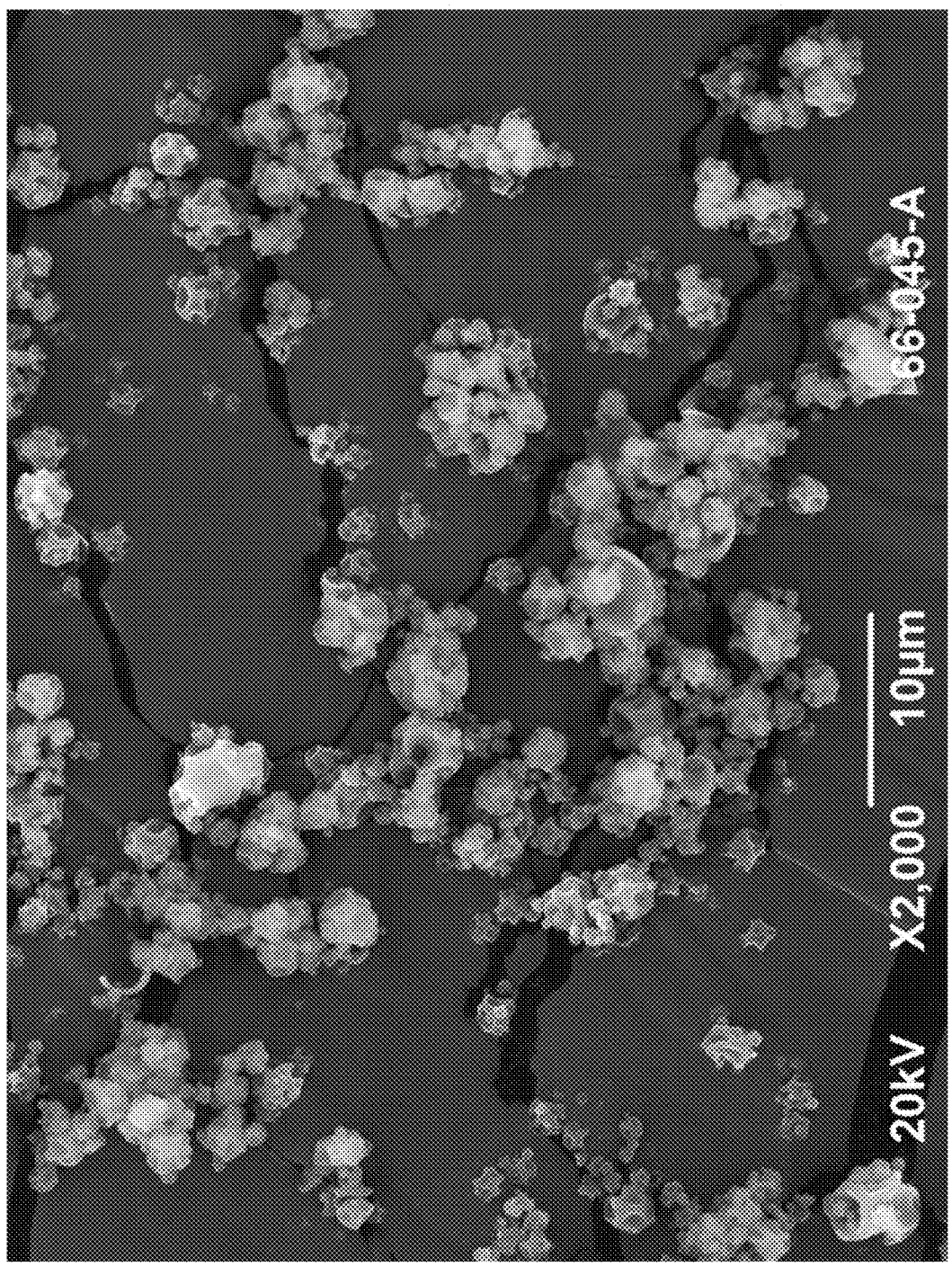
Figure 25:
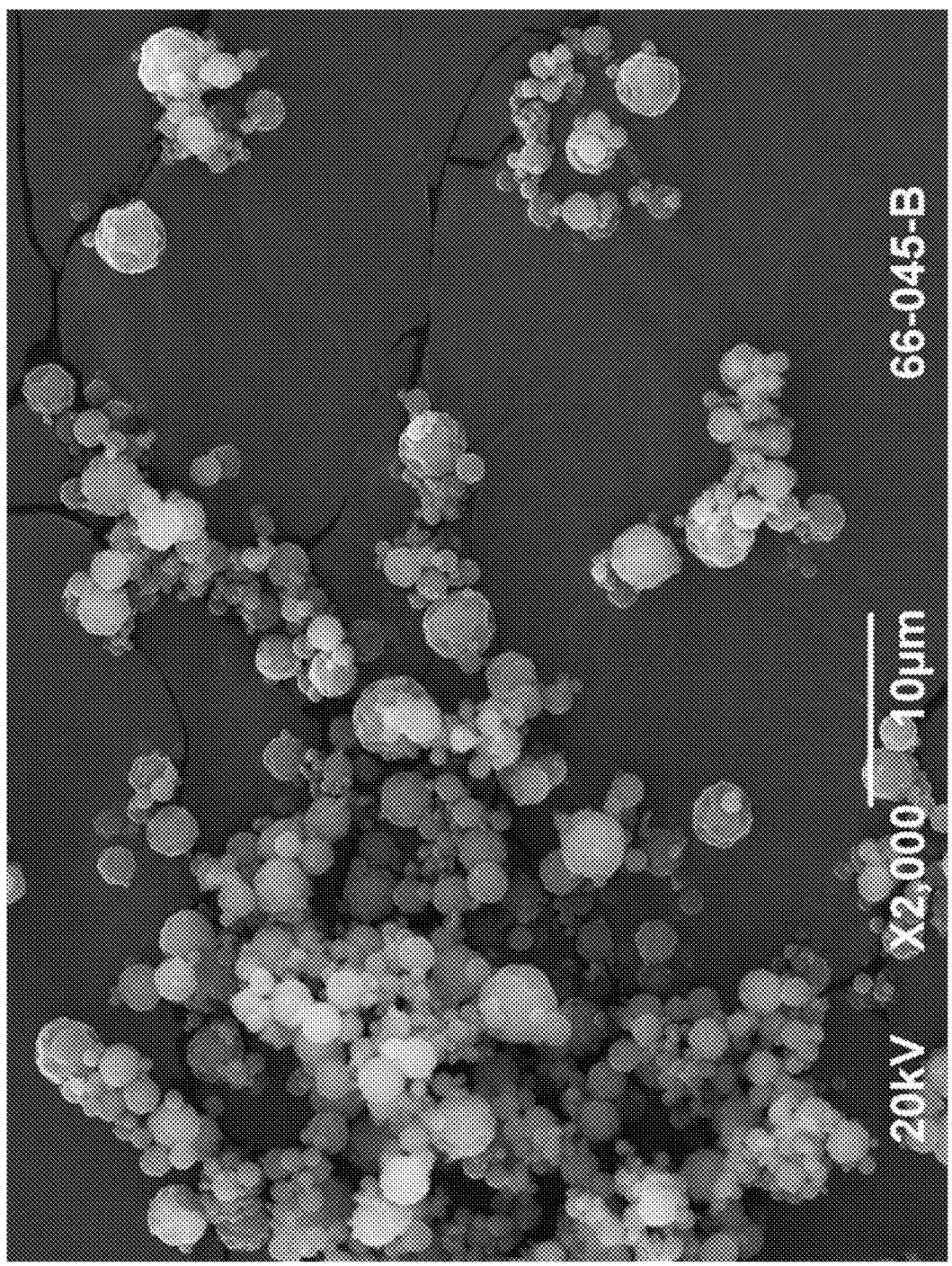
Figure 26:
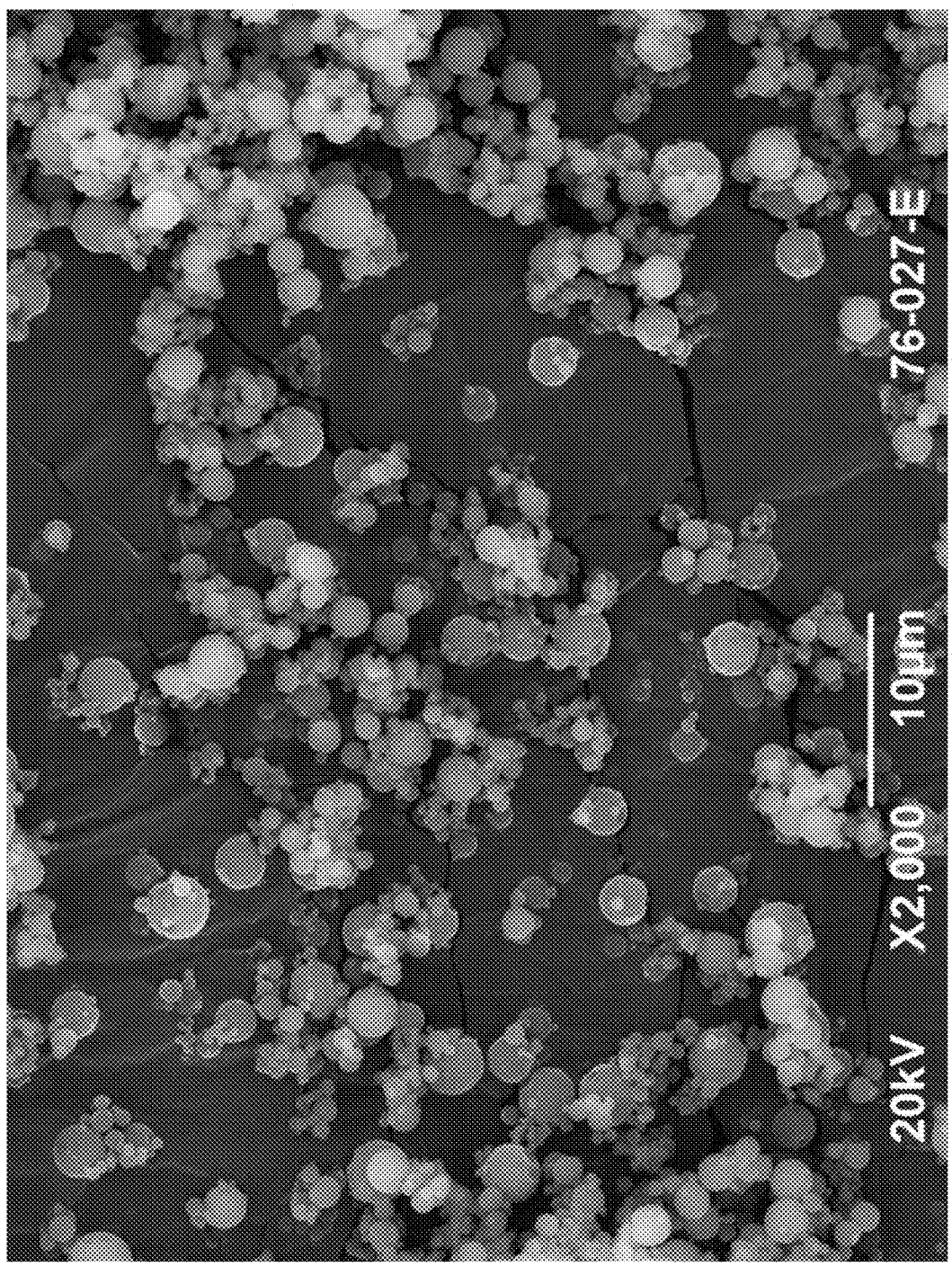

Electron micrographs of the suspending particles showed a variety of morphologies, and are shown in FIG. 23 through FIG. 26, with FIG. 23 providing a micrograph of trehalose suspending particles, FIG. 24 providing a micrograph of HP-β-cyclodextrin suspending particles, FIG. 25 providing a micrograph of Ficoll MP 70 suspending particles, and FIG. 26 providing a micrograph of inulin suspending particles. Trehalose particles appear to be spherical, with a smooth surface. HP-β-cyclodextrin particles show extensive wrinkling of the surface, suggesting a partially buckled exterior with a hollow core. Ficoll MP 70 and Inulin particles display some surface rugosity but are generally spheroidal.

Metered dose inhalers were prepared by weighing 0.9 mg of the micronized FF active agent particles and 60 mg of suspending particles into coated glass vials with 15 mL volume. FF was combined with each type of the four suspending particle species of Table 11. The canisters were crimp sealed with 50 μL valves (Valois DF31/50 RCU, Les Vaudreuil, France) and filled with 10 mL of HFA propellant 134a (Ineos Fluor, Lyndhurst, UK) by overpressure through the valve stem. After injecting the propellant, the canisters were sonicated for 30 seconds and agitated on a wrist action shaker for 30 minutes. Additional inhalers containing suspending particles only and active agent particles only were filled as a control for each configuration.

Crystalline FF has a greater density than propellant 134a at room temperature, as do all four species of suspending particles in the present example. Consequently both FF and suspending particles settled to the bottom of the inhalers at room temperature. To test these inhalers for active-suspending agent particle interactions indicating a co-suspension, the inhalers were immersed in an ethanol bath at ≤−10° C. (resulting in increased propellant density) and allowed to equilibrate for a minimum of 30 minutes. At this temperature, the FF active agent particles are less dense than the propellant and consequently cream to the top of the propellant volume, while all four species of suspending agent particles remain settled at the bottom of the propellant volume.

The tested configurations and the results of the observations are presented in Table 13. FF active agent particles alone formed a cream layer atop the propellant volume, and trehalose, HP-β-cyclodextrin, inulin, and Ficoll PM70 particles alone all settled to the bottom of the glass vial. FF active agent particles in combination with trehalose suspending particles formed a single sediment layer, with no particles creamed or afloat in the propellant, indicating that the FF particles interact with the trehalose suspending particles, and a co-suspension is formed. In the case of FF particles in combination with HP-β-cyclodextrin suspending particles, some turbidity was present in the propellant, similar to that observed in the suspending particle only control vial. Additionally, some floating flocs were observed, which may have been FF particles; however, such flocs accounted for a small amount of solid mass relative to the control vial, indicating that some if not all FF particles were interacting with the suspending agent particles. Thus, this configuration is an example of a partial co-suspension. FF particles in combination with inulin suspending particles formed a single sediment layer, indicating a co-suspension was formed. Though some turbidity was present in this configuration, similar cloudiness was observed in the inulin-only control vial. FF active agent particles in combination with Ficoll PM70 suspending particles formed a sediment layer at the bottom of the vial, indicating that a co-suspension was formed. While some turbidity and floating flocs were observed in this configuration, similar turbidity, and floc frequency were observed in the Ficoll-only control vial.

TABLE 13

Summary of tested configurations and results of observations

| Container ID | Contents in 10 mL p134a | Suspending Particle to Active Particle Ratio | Observational Notes, ≤−10° C. | Co-suspension |
|---|---|---|---|---|
| 0-FF | 0.9 mg FF | n/a | Creamed to top | n/a |
| T | 60 mg trehalose | n/a | Settled to bottom | n/a |
| T-FF | 60 mg trehalose, 0.9 mg FF | 67 | Sediment layer; no particles creamed | Yes |
| C | 60 mg HP-β-cyclodextrin | n/a | Settled to bottom; some turbidity | n/a |
| C-FF | 60 mg HP-β-cyclodextrin, 0.9 mg FF | 67 | Solids mostly in sediment layer at bottom; some turbidity; some floating flocs present | partial |
| I | 60 mg Inulin | n/a | Settled to bottom; some turbidity | n/a |
| I-FF | 60 mg Inulin, 0.9 mg FF | 67 | Sediment layer; no particles creamed; some turbidity | Yes |
| F | 60 mg Ficoll PM70 | n/a | Settled to bottom, with some floating flocs | n/a |
| F-FF | 60 mg Ficoll PM70, 0.9 mg FF | 67 | Sediment layer; very few floating flocs | Yes |

Example 16

Co-suspension compositions including glycopyrrolate (GP) and formoterol fumarate (FF) active agent particles were produced and MDIs incorporating the co-suspension compositions were prepared. The co-suspension compositions produced included GP active agent particles, FF active agent particles or a combination of both GP and FF active agent particles. The GP and FF material was supplied as micronized, crystalline material with particle size distribution as shown in Table 14.

Suspending particles were manufactured via spray dried emulsion at a feed stock concentration of 80 mg/mL with a composition of 93.44% DSPC (1,2-Distearoyl-sn-Glycero-3-Phosphocholine) and 6.56% anhydrous calcium chloride (equivalent to a 2:1 DSPC:CaCl$_2$ mole/mole ratio). During the emulsion preparation, DSPC and CaCl$_2$ was dispersed with a high shear mixer at 8000-10000 rpm in a vessel containing heated water (80±3° C.) with PFOB slowly added during the process. The emulsion was then processed with 6 passes in a high pressure homogenizer (10000-25000 psi). The emulsion was then spray dried via a spray dryer fitted with a 0.42" atomizer nozzle with a set atomizer gas flow of 18 SCFM. The drying gas flow rate was set to 72 SCFM with an inlet temperature of 135° C., outlet temperature 70° C., and an emulsion flow rate of 58 mL/min.

The co-suspensions were prepared by first dispensing the appropriate quantities of micronized GP and FF active agent particles and suspending particles into a drug addition vessel (DAV) inside a humidity controlled chamber (RH<5%). In the present Example, the suspending particles were added in three equal portions intercalating the addition of GP and FF after the first and second addition respectively. The DAV is then sealed under a nitrogen atmosphere and connected to the suspension vessel containing 12 kg of HFA-134a (Ineos Fluor, Lyndhurst, UK). A slurry was then formed by adding 0.5-1 kg of HFA-134a into the DAV, which is then removed from the suspension vessel and gently swirled. The slurry is then transferred back to the suspension mixing vessel and diluted with additional HFA-134a to form the final suspension at target concentration stirring gently with an impeller. The suspension is then recirculated via a pump to the filling system for a minimum time prior to initiation of filling. Mixing and recirculation continue throughout the filling process. 50 µL valves (Bespak, King's Lynn, UK) are placed onto 14-mL fluorinated ethylene polymer (FEP) coated aluminum canisters (Presspart, Blackburn, UK) canisters and then purged of air either by a vacuum crimping process, or an HFA-134a purging process followed by valve crimping. The crimped canisters are then filled through-the-valve with the appropriate quantity of suspension, adjusted by the metering cylinder.

TABLE 14

Glycopyrrolate and Formoterol Fumarate particle size distributions.

| Designation | $d_{10}$ (µm) | $d_{50}$ (µm) | $d_{90}$ (µm) | Span |
|---|---|---|---|---|
| FF API | 0.6 | 1.9 | 4.1 | 1.8 |
| GP API | 0.5 | 1.3 | 3.0 | 1.9 |

MDIs containing the dual co-suspensions described in this Example were prepared to contain two different doses GP and FF. Specifically, a first run of dual co-suspension compositions were prepared to provide 18 µg per actuation GP and 4.8 µg per actuation FF ("low dose"), and a second run of dual co-suspension compositions were prepared to provide 36 µg per actuation GP and 4.8 µg per actuation FF ("high dose"). In addition to the dual co-suspensions compositions, co-suspensions including a single species of active agent particle were prepared. These compositions included either GP active agent particles or FF active agent particles and were referred to as "mono" or "monotherapy" co-suspensions. The monotherapy co-suspension compositions were prepared as described for the dual co-suspensions, except that they included only one species of active agent particles (either GP or FF). The monotherapy co-suspensions were formulated and monotherapy MDIs prepared to provide the following targeted delivered doses: 18 µg per actuation of GP, and 0.5, 1.0, 3.6 or 4.8 µg per actuation of FF. The compositions and MDIs providing 0.5 µg FF and 1 µg FF per actuation are referred to as "ultra low" dose and were manufactured in a similar manner at a 4 L scale.

Figure 27:
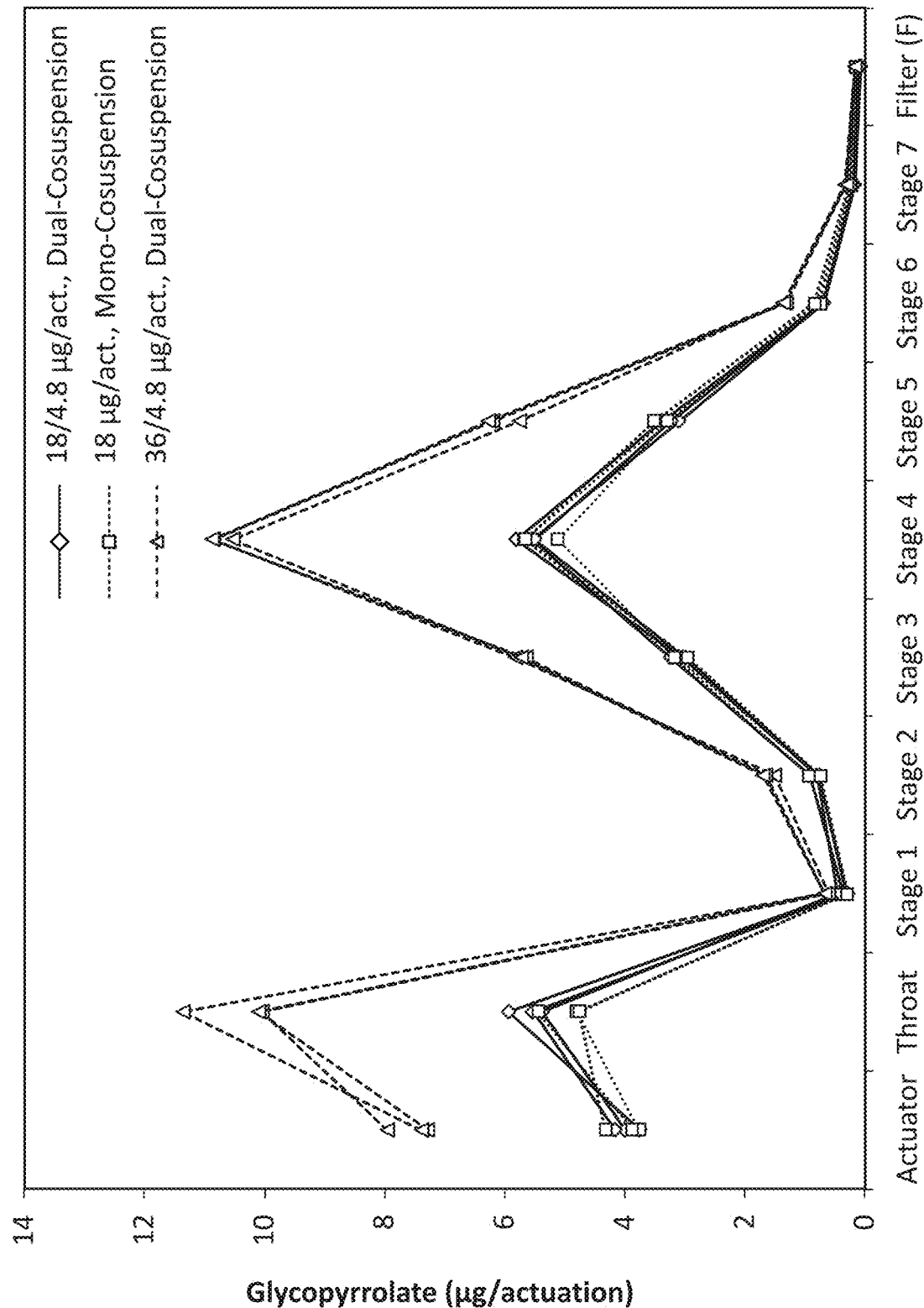
FIG. 27 provides a graph that depicts the aerodynamic particle size distribution determined by cascade impaction of exemplary co-suspension compositions prepared according to the present description and including glycopyrrolate active agent particles.
Figure 28:
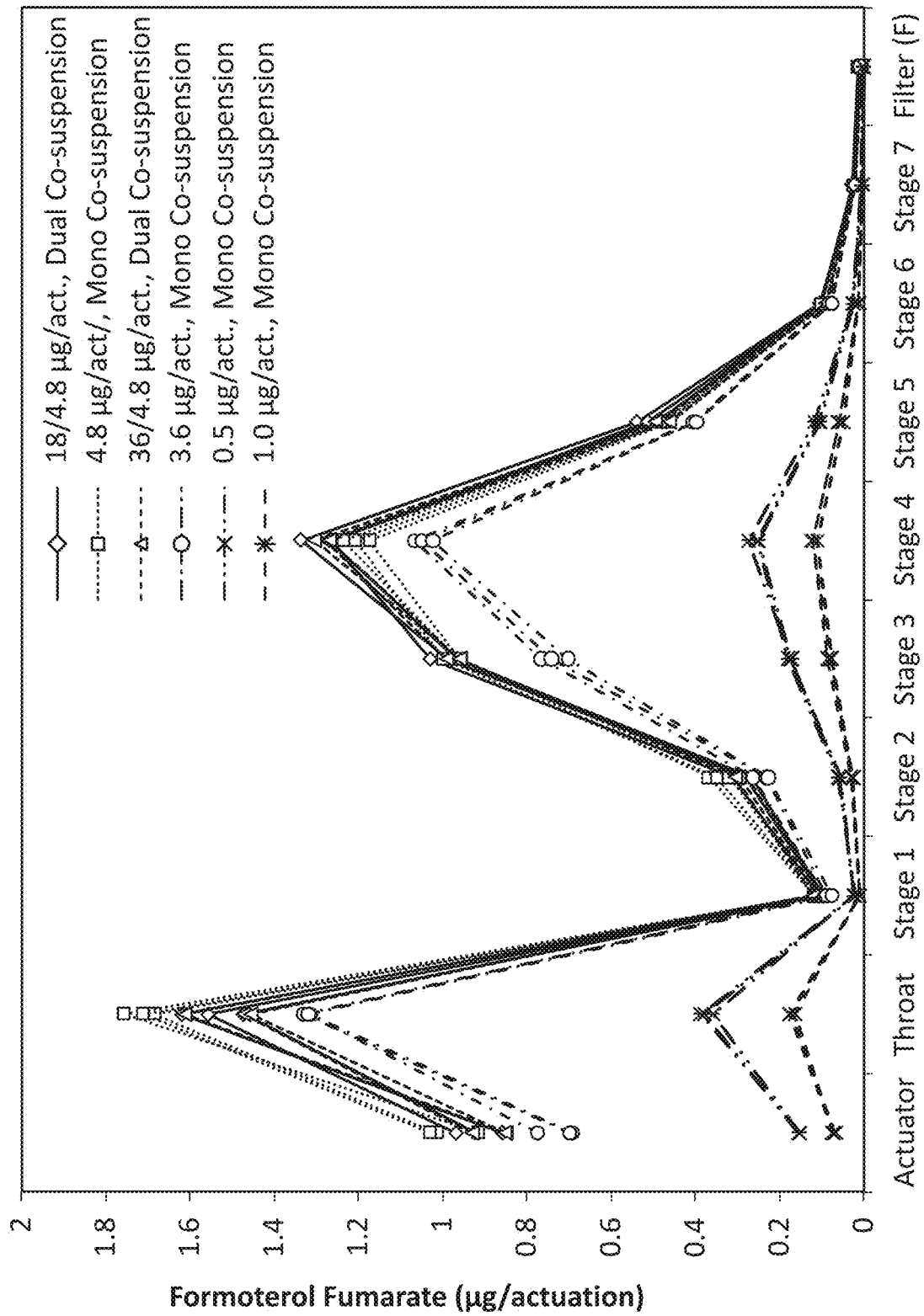
FIG. 28 provides a graph that depicts the aerodynamic particle size distribution determined by cascade impaction of exemplary co-suspension compositions prepared according to the present description and including formoterol fumarate active agent particles.

The drug specific aerodynamic size distributions achieved with MDIs containing the co-suspension compositions prepared according to this Example were determined as described in Example 1. The proportionality of the aerodynamic size distributions of GP obtained from the low and high dose dual co-suspensions as well as the equivalency between the dual and monotherapy co-suspensions is demonstrated in FIG. 27. In the same manner, the proportionality of the aerodynamic size distributions of FF obtained from the dual and monotherapy co-suspensions, including the ultralow, low, and high dose compositions is demonstrated in FIG. 28.

Figure 29:
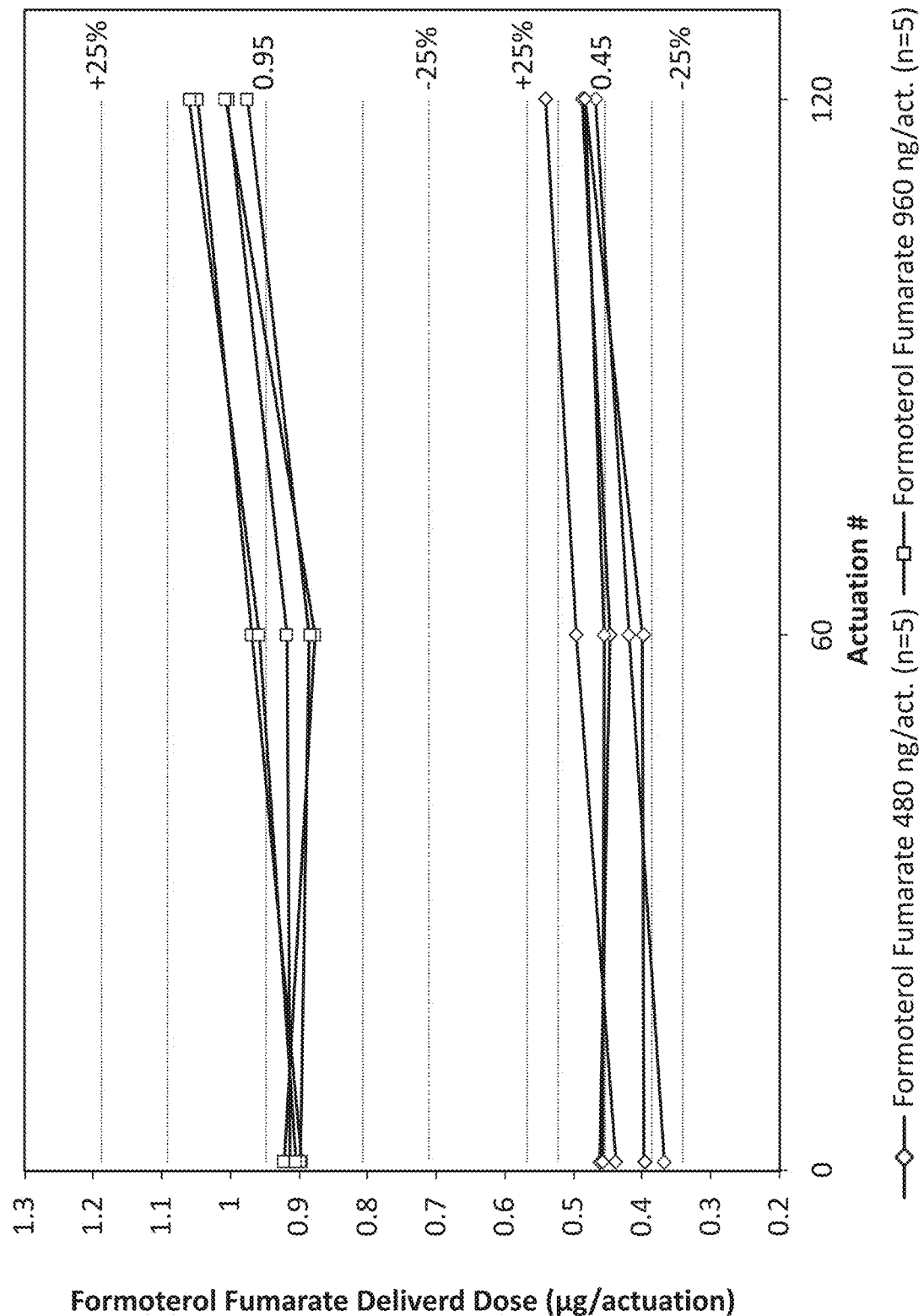
FIG. 29 provides a graph that depicts the delivered dose uniformity achieved by ultra low-dose formoterol fumarate co-suspension compositions prepared according to the present description.
Figure 30:
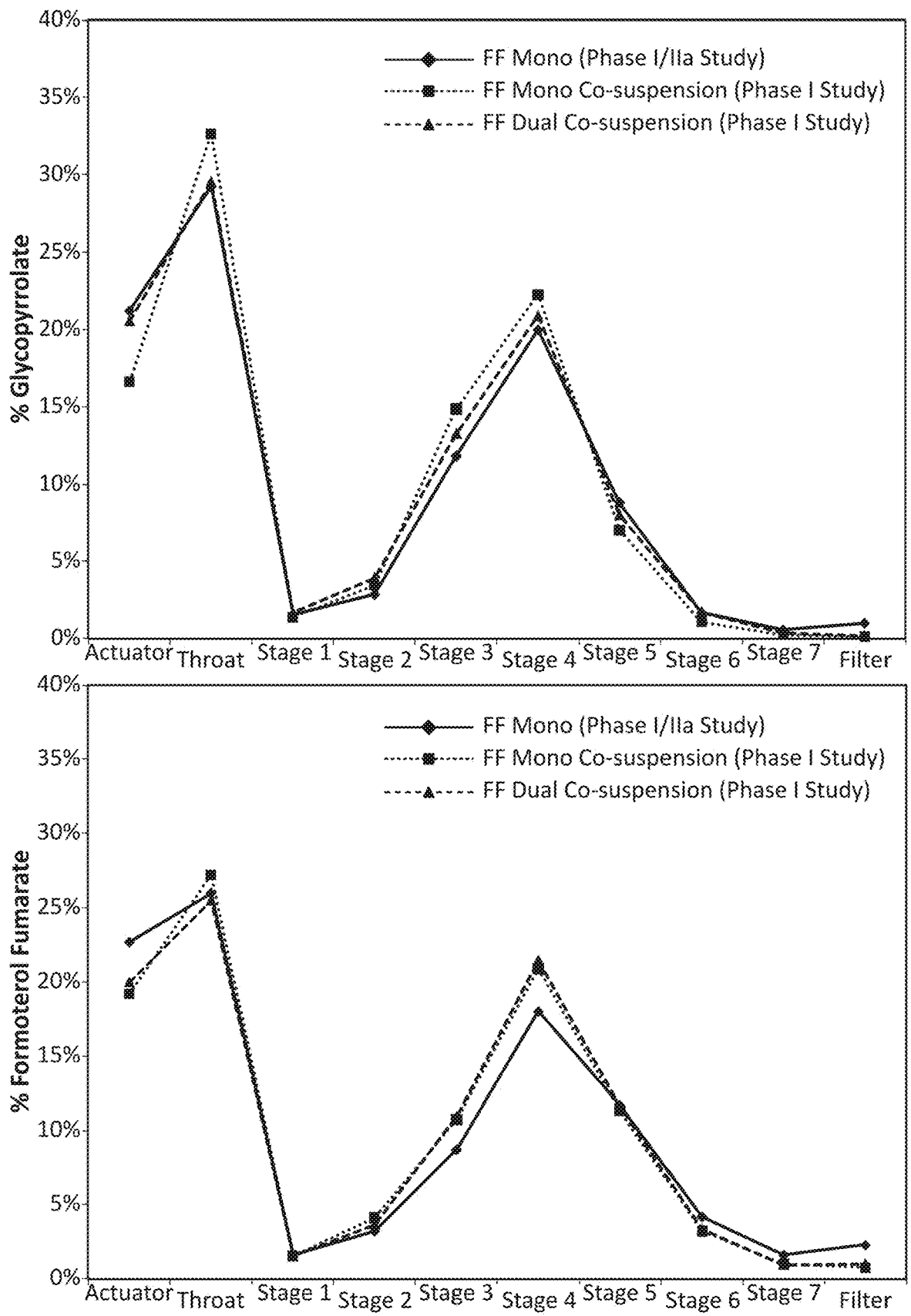
FIG. 30 provides graphs illustrating the particle size distribution of glycopyrrolate (top) and formoterol (bottom) achieved by an exemplary co-suspension compared to particle size distributions achieved by formulations including either glycopyrrolate or formoterol fumarate alone.

The delivered dose uniformity of the ultra low dose FF monotherapy MDIs was also measured as described in Example 1. The DDU for the FF MDI containing 0.5 µg per actuation and 1.0 µg per actuation are shown in FIG. 29. Desirable dose delivery uniformity is achieved demonstrating the utility of the present invention to consistently deliver ultra low doses. In order to evaluate whether the combination of GP and FF within a single formulation would result in the degradation of the aerosol properties relative to compositions including a single active agent, the aerosol properties of co-suspension compositions were assessed relative to suspension compositions including only a single active agent. As can be seen in FIG. 30, the aerosol performance of the combination co-suspension composition including both GP and FF active agent was no different than the aerosol performance achieved by suspension compositions including either GP or FF alone. Therefore, there were no combination effects observed.

Example 17

Micronized salmeterol xinafoate (4-hydroxy-α1-[[[6-(4-phenylbutoxy)hexyl]amino] methyl]-1,3-benzenedimethanol, 1-hydroxy-2-naphthalenecarboxylate) was received by the manufacturer (Inke SA, Germany) and used as active agent particles. The particle size distribution of the salmeterol xinafoate (SX) was determined by laser diffraction. 50% by volume of the micronized particles exhibited an optical diameter smaller than 2 µm, 90% by volume exhibited an optical diameter smaller than 3.9 µm.

Suspending particles were manufactured as follows: 150 mL of a fluorocarbon-in water emulsion of PFOB (perfluoroctyl bromide) stabilized by a phospholipid was prepared. 12.3 g of the phospholipid, DSPC (1,2-Distearoyl-sn-Glycero-3-Phosphocholine), and 1.2 g of calcium chloride were homogenized in 100 mL of hot water (70° C.) using a high shear mixer. 65 mL of PFOB were added slowly during homogenization. The resulting coarse emulsion was then further homogenized using a high pressure homogenizer (Model C3, Avestin, Ottawa, Calif.) at pressures of up to 140 MPa for 3 passes The emulsion was spray dried in nitrogen using the following spray drying conditions: Inlet temperature 90° C., outlet temperature 69° C., emulsion feed rate 2.4 mL/min, total gas flow 498 l/min. The particle size distribution of the suspending particles, VMD, was determined by laser diffraction. 50% by volume of the suspending particles were smaller than 2.7 µm, the Geometric Standard Deviation of the distribution was 2.0. Additionally, the aerodynamic particle size distribution of the suspending particles was determined with a time-of-flight particle sizer. 50% by volume of the suspending particles had an aerodynamic particle diameter smaller than 1.6 µm. The large difference between aerodynamic particle diameter and optical particle diameter indicates that the suspending particles had a low particle density <0.5 kg/L.

Metered dose inhalers were prepared by weighing 2 mg of SX active agent particles and 60 mg of suspending particles into fluorinated ethylene polymer (FEP) coated aluminum canisters (Presspart, Blackburn, UK) with 19 mL volume. The suspending particle to active particle ratio was 30. The target delivered dose assuming 20% actuator deposition was 10 μg. The canisters were crimp sealed with 63 μl valves (#BK 357, Bespak, King's Lynn, UK) and filled with 10 mL of HFA 134a (1,1,1,2-tetrafluoroethane) by overpressure through the valve stem. After injecting the propellant, the canisters were sonicated for 15 seconds and agitated on a wrist action shaker for 30 minutes. The canisters were fitted with polypropylene actuators with a 0.3 mm orifice (#BK 636, Bespak, King's Lynn, UK). Additional inhalers for visual observation of suspension quality were prepared using 15 mL glass vials including a comparator filled with micronized SX only. Aerosol performance was assessed as described in Example 1. The MMAD was 3.7 μm and the fine particle fraction was 48%. Because the SX crystals forming the active agent particles and the propellant were nearly density matched at 15° C.-20° C., the visual observation was conducted on glass vials that were heated up to 30° C.-35° C. in a water bath. Under these conditions the SX active agent particles formulated alone sedimented rapidly, but no SX crystals were visible at the bottom of the co-suspension vial.

Micronized salmeterol xinafoate active agent particles were co-suspended through association with suspending particles of low density that were formulated according to the disclosure provided herein. The association between salmeterol crystals and the suspending particles was strong enough to overcome buoyancy forces as it was observed that settling of the crystals is inhibited.

The invention claimed is:

1. A pharmaceutical composition deliverable from a metered dose inhaler, comprising:

- a suspension medium comprising a pharmaceutically acceptable propellant;
- a plurality of active agent particles comprising a long-acting muscarinic antagonist (LAMA) active agent or a long-acting $\beta_2$ adrenergic receptor agonist (LABA) active agent; and
- a plurality of respirable suspending particles, wherein the respirable suspending particles are formed separately from and are different particles than the active agent particles and are formed of a dry particulate phospholipid material that is substantially insoluble in the suspension medium;
- and wherein the ratio of the total mass of the respirable suspending particles to the total mass of the active agent particles is from greater than 1:1 up to 200:1.

2. The pharmaceutical composition according to claim 1, wherein the suspending particles comprise perforated microstructures.

3. The pharmaceutical composition according to claim 2, wherein the perforated microstructures are prepared using a spray drying process.

4. The pharmaceutical composition according to claim 3, wherein the perforated microstructures comprise a spray dried emulsion of perfluorooctyl bromide, DSPC, and calcium chloride in water.

5. The pharmaceutical composition according to claim 1, wherein the suspending particles exhibit an MMAD selected from the group consisting of between about 10 μm and about 500 nm, between about 5 μm and about 750 nm, and between about 1 μm and about 3 μm.

6. The pharmaceutical composition according to claim 1, wherein the suspending particles exhibit a volume median optical diameter selected from the group consisting of between about 0.2 μm and about 50 μm, between about 0.5 μm and about 15 μm, between about 1.5 μm and about 10 μm, and between about 2 μm and about 5 μm.

7. The pharmaceutical composition according to claim 1, wherein the propellant comprises a propellant selected from the group consisting of an HFA propellant, a PFC propellant, and combinations thereof.

8. The pharmaceutical composition according to claim 1, wherein a ratio of the total mass of the suspending particles to the total mass of the active agent particles is selected from the group consisting of above about 1.5, up to about 5, up to about 10, up to about 15, up to about 17, up to about 20, up to about 30, up to about 40, up to about 50, up to about 60, up to about 75, up to about 100, up to about 150, and up to about 200.

9. The pharmaceutical composition according to claim 1, wherein the active agent particles comprise crystalline active agent.

10. The pharmaceutical composition according to claim 1, wherein the active agent particles comprise micronized, crystalline active agent.

11. The pharmaceutical composition according to claim 1, wherein the active agent included in the active agent particles is a LAMA active agent selected from the group consisting of glycopyrrolate, dexpirronium, tiotropium, trospium, aclidinium, and darotropium, or a pharmaceutically acceptable salt thereof.

12. The pharmaceutical composition according to claim 11, wherein the active agent particles comprise glycopyrrolate, or a pharmaceutically acceptable salt thereof.

13. The pharmaceutical composition according to claim 12, wherein the active agent particles comprise crystalline glycopyrrolate, or a pharmaceutically acceptable salt thereof.

14. The pharmaceutical composition according to claim 12, wherein the active agent particles comprise micronized, crystalline glycopyrrolate, or a pharmaceutically acceptable salt thereof.

15. The pharmaceutical composition according to claim 12, wherein the glycopyrrolate active agent particles are included in the suspension medium at a concentration sufficient to provide a delivered dose of glycopyrrolate per actuation of the metered dose inhaler of no more than 10 μg.

16. The pharmaceutical composition of claim 15, wherein the glycopyrrolate active agent particles comprise a pharmaceutically acceptable salt of glycopyrrolate selected from the group consisting of fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenylacetate or triphenylacetate, o-hydroxybenzoate, p-hydroxybenzoate, 1-hydroxynaphthalene-2-carboxylate, 3-hydroxynaphthalene-2-carboxylate, methanesulfonate, and benzenesulfonate salts.

17. The pharmaceutical composition of claim 16, wherein the pharmaceutically acceptable salt of glycopyrrolate is selected from the group consisting of fluoride, chloride, bromide, and iodide salts.

18. The pharmaceutical composition of claim 17, wherein the pharmaceutically acceptable salt of glycopyrrolate is 3-[(cyclopentyl-hydroxyphenylacetyl)oxy]-1,1-dimethyl-pyrrolidinium bromide.

19. A pharmaceutical composition according to claim 1, wherein the active agent included in the active agent particles is a LABA active agent selected from the group consisting of bambuterol, clenbuterol, formoterol, salmeterol, carmoterol, milveterol, indacaterol, and saligenin- or indole-containing and adamantyl-derived β2 agonists, or a pharmaceutically acceptable salt thereof.

20. The pharmaceutical composition according to claim 19, wherein the active agent particles comprise formoterol, or a pharmaceutically acceptable salt thereof.

21. The pharmaceutical composition according to claim 19, wherein the active agent particles comprise crystalline formoterol, or a pharmaceutically acceptable salt thereof.

22. The pharmaceutical composition according to claim 19, wherein the active agent particles comprise micronized, crystalline formoterol, or a pharmaceutically acceptable salt thereof.

23. The pharmaceutical composition according to claim 19, wherein the formoterol active agent particles are included in the suspension medium at a concentration sufficient to provide a delivered dose of formoterol per actuation of the metered dose inhaler of no more than 5 μg.

24. The pharmaceutical composition according to claim 23, wherein the formoterol active agent particles comprise a pharmaceutically acceptable salt of formoterol selected from the group consisting of hydrochloric, hydrobromic, sulfuric, phosphoric, fumaric, maleic, acetic, lactic, citric, tartaric, ascorbic, succinic, glutaric, gluconic, tricarballylic, oleic, benzoic, p-methoxybenzoic, salicylic, o- and p-hydroxybenzoic, p-chlorobenzoic, methanesulfonic, p-toluenesulfonic, and 3-hydroxy-2-naphthalene carboxylic acid salts.

25. The pharmaceutical composition according to claim 24, wherein the pharmaceutically acceptable salt of formoterol is formoterol fumarate.

26. A method for treating a pulmonary disease or disorder in a patient, wherein the pulmonary disease or disorder is selected from at least one of the group consisting of asthma, COPD, allergic rhinitis, sinusitis, pulmonary vasoconstriction, inflammation, allergies, impeded respiration, respiratory distress syndrome, pulmonary hypertension, and pulmonary inflammation or obstruction resulting from cystic fibrosis, the method comprising administering a therapeutically effective amount of a pharmaceutical composition from a metered dose inhaler, the pharmaceutical composition comprising:
a suspension medium comprising a pharmaceutically acceptable propellant;
a plurality of active agent particles comprising a LAMA active agent or a LABA active agent; and
a plurality of respirable suspending particles, wherein the respirable suspending particles are formed separately from and are different particles than the active agent particles and are formed of a dry particulate phospholipid material that is substantially insoluble in the suspension medium;
and wherein the ratio of the total mass of the respirable suspending particles to the total mass of the active agent particles is from greater than 1:1 up to 200:1.

27. The method of claim 26, wherein the active agent particles comprise crystalline active agent.

28. The method of claim 26, wherein the active agent particles comprise micronized, crystalline active agent.

29. The method of claim 26, wherein the active agent comprises a LAMA active agent selected from the group consisting of glycopyrrolate, dexpirronium, tiotropium, trospium, aclidinium, and darotropium, or a pharmaceutically acceptable salt thereof.

30. The method of claim 26, wherein the active agent comprises a LABA active agent selected from the group consisting of bambuterol, clenbuterol, formoterol, salmeterol, carmoterol, milveterol, indacaterol, and saligenin- or indole-containing and adamantyl-derived $β_2$ agonists, or a pharmaceutically acceptable salt thereof.

31. The method of claim 29, wherein said administering the pharmaceutical composition comprises administering a delivered dose of glycopyrrolate, or a pharmaceutically acceptable salt thereof, of no more than 150 μg.

32. The method of claim 31, wherein the glycopyrrolate, or pharmaceutically acceptable salt thereof, comprises crystalline glycopyrrolate.

33. The method of claim 31, wherein the glycopyrrolate, or pharmaceutically acceptable salt thereof, comprises micronized, crystalline glycopyrrolate.

34. The method of claim 31, wherein the glycopyrrolate active agent particles comprise a pharmaceutically acceptable salt of glycopyrrolate and the pharmaceutically acceptable salt of glycopyrrolate is 3-[(cyclopentyl-hydroxyphenylacetyl)oxy]-1,1-dimethylpyrrolidinium bromide.

35. The method according to claim 31, wherein said administering results in a clinically significant increase in inspiratory capacity (IC) in the patient.

36. The method of claim 29, wherein said administering the pharmaceutical composition comprises administering a delivered dose of glycopyrrolate, or a pharmaceutically acceptable salt thereof, of no more than 80 μg, and said administering results in an increase in $FEV_1$ of at least 150 mL within 0.5 hours, or less.

37. The method according to claim 30, wherein said administering of the pharmaceutical composition comprises delivering a dose of 10 μg, or less, of formoterol, or a pharmaceutically acceptable salt thereof, per actuation of the metered dose inhaler.

38. The method of claim 37, wherein the formoterol, or pharmaceutically acceptable salt thereof, comprises crystalline formoterol.

39. The method of claim 37, wherein the formoterol, or pharmaceutically acceptable salt thereof, comprises micronized, crystalline formoterol.

40. The method of claim 37, wherein the active agent particles comprise a pharmaceutically acceptable salt of formoterol and the pharmaceutically acceptable salt of formoterol is formoterol fumarate.

41. The method according to claim 30, wherein said administering of the pharmaceutical composition comprises delivering a dose of 10 μg, or less, of formoterol, or a pharmaceutically acceptable salt thereof, per actuation of the metered dose inhaler, and said administering of the pharmaceutical composition results in a clinically significant increase in $FEV_1$ in the patient.

* * * * *

UNITED STATES PATENT AND TRADEMARK OFFICE
CERTIFICATE OF CORRECTION

| | |
|---|---|
| PATENT NO. | : 10,716,753 B2 |
| APPLICATION NO. | : 16/179712 |
| DATED | : July 21, 2020 |
| INVENTOR(S) | : Reinhard Vehring et al. |

It is certified that error appears in the above-identified patent and that said Letters Patent is hereby corrected as shown below:

On the Title Page

<u>Page 3, item [56]</u>:
"EP 1 504 760 B1 10/1996"
Should read:
--EP 0 504 760 B1 10/1996--

Signed and Sealed this
Seventeenth Day of November, 2020

Andrei Iancu
*Director of the United States Patent and Trademark Office*